US007989677B2

(12) United States Patent
Tanksley et al.

(10) Patent No.: US 7,989,677 B2
(45) Date of Patent: Aug. 2, 2011

(54) NUCLEIC ACIDS AND PROTEINS ASSOCIATED WITH SUCROSE ACCUMULATION IN COFFEE

(75) Inventors: Steven D. Tanksley, Dryden, NY (US); Chenwei Lin, Auburndale, MA (US); Isabelle Muguette Privat, Saint Pierre des Corps (FR); James Gérard McCarthy, Noizay (FR); Vincent Petiard, Tours (FR)

(73) Assignees: Nestec S. A., Vevey (CH); Cornell University, Ithaca, NY (US)

( * ) Notice: Subject to any disclaimer, the term of this patent is extended or adjusted under 35 U.S.C. 154(b) by 555 days.

(21) Appl. No.: 11/990,549

(22) PCT Filed: Aug. 16, 2006

(86) PCT No.: PCT/US2006/032062
§ 371 (c)(1),
(2), (4) Date: Feb. 15, 2008

(87) PCT Pub. No.: WO2007/022318
PCT Pub. Date: Feb. 22, 2007

(65) Prior Publication Data
US 2009/0055974 A1 Feb. 26, 2009

Related U.S. Application Data

(60) Provisional application No. 60/709,043, filed on Aug. 17, 2005.

(51) Int. Cl.
*C12N 15/82* (2006.01)
*C12N 15/63* (2006.01)
*C12N 15/11* (2006.01)
*C07H 21/04* (2006.01)
*A01H 5/00* (2006.01)

(52) U.S. Cl. ..... 800/284; 800/287; 800/295; 435/320.1; 435/468; 536/23.1; 536/23.2; 536/23.6

(58) Field of Classification Search .................. None
See application file for complete search history.

(56) References Cited

U.S. PATENT DOCUMENTS
5,976,869 A  11/1999 Sonnewald .............. 435/278

FOREIGN PATENT DOCUMENTS
WO   WO/00/12733   3/2000

OTHER PUBLICATIONS

Database EMBL [Online] Jun. 15, 2005, "Coffee Canephora Sus1 Gene for Sucrose Synthase," Exons 1-13, XP002427136, 1-7, 21-35, EMBL: AJ880768, Database Aaccession No. AJ880768, relevant to invention 1, the whole document.
Database Uniprot [Online], Jul. 19, 2005, "Sucrose Synthase (EC 1.3.1.13)." XP002427137 retrieved from EBI Accession No. UNIPROT: Q40ZT3, relevant to invention 1, the whole document.
Database EMBL [Online] Jul. 21, 2003 m "Coffea arabica Partial mRNA for Sucrose Synthase (Sus1) gene," XP002425053, retrieved from EBI Accession No. EMBL: AJ575256, Database Accession No. AJ575256, relevant to invention 1, the whole document.
Database Uniprot [Online} Jul. 5, 2004, "Sucrose Synthase (EC 2.4.1.13) (Fragment)," XP002425054, retrieved from EBI Accession No. UNIPROT:Q7KR0, relevant to invention 1, the whole document.
Fu, H. Et al., "Sink and Vascular Associated Sucrose Synthase Functions are Encoded by Different Gene Classes in Potato," *Plant Cell*, American Society of Plant Physiologists, Rockville, MD, US, Sep. 1995, pp. 1369-1385, XP002985138, ISSN: 1040-4651, relevant to invention 1, the whole document.
Database EMBL [Online] Aug. 19, 1993, "Lycopersicon Esculentum Fruit Sucrose Synthase mRNA, complete cds," XP002427138, retrieved from EBI Accession No. L19762, relevant to invention 1, the whole document.
Database UniProt [Online] Feb. 1, 1996, „Sucrose Synthase (EC 2.4.1.13) (Sucrose-UDP Glucosyltransferase), XP002427139, retrieved from EBI Accession No. UNIPROT:P49037, relevant to invention 1, the whole document.
Wang, Fei et al., "Isolation and Sequencing of Tomato Fruit Sucrose Synthase cDNA," *Plant Physiology* (Rockville), vol. 103(4), pp. 1463-1464, 1993, XP002427059, ISSN: 0032-0889, relevant to invention 1, the whole document.
Ky, C-L et al., Inheritance of Coffee Bean Sucrose Content in the Interspecific Cross Coffea Pseudozanquebariae X Coffea Liberica dewevrel; *Plant Breeding*, vol. 119(2), Apr. 2000, pp. 165-168, XP009080542, ISSN: 0179-9541, relevant to inventions 1 and 2, the whole document.
Nguyen-Quoc, Binh et al., "A Role for 'Futile Cycles' Involving Invertase and Sucrose Synthase in Sucrose Metabolism of Tomato Fruit," *Journal of Experimental Botany*, vol. 52(358) May 2001, pp. 881-889, XP002430552, ISSN: 0022-0957, cited in the application, relevant to inventions 1 and 2, the whole document.
Winter, H. et al., "Regulation of Sucrose Metabolism in Higher Plants: Localization and Regulation of Activity of Key Enzymes," *Critical Reviews in Plant Sciences*, CRC Press, Boca Raton, FL, US., vol. 19(1), Mar. 2000 pp. 31-67, XP001008648, ISSN: 0735-2689, relevant to inventions 1 and 2, the whole document.
Geromel, C. et al., "Sugar Metabolism During Coffee Fruit Development," ASIC 2004, 20th International Conference on Coffee Science, Bangalore, India, Oct. 11-15, 2004, pp. 651-655, 8 Ref. Publisher: Association Scientifique Internationale du Café (ASIC), Paris Price: Book Chapter: Conference Paper Meeting Info., ASI, 2005, pp. 651-655, XP009081448, relevant to invention 1, the whole document.

(Continued)

*Primary Examiner* — Brent T Page
(74) *Attorney, Agent, or Firm* — Potter Anderson & Corroon LLP

(57) ABSTRACT

Disclosed herein are nucleic acid molecules isolated from coffee (*Coffea* spp.) comprising sequences that encodes various sucrose metabolizing enzymes, along with their encoded proteins. Specifically, sucrose synthase, sucrose phosphate synthase and sucrose phosphatase enzymes and their encoding polynucleotides from coffee are disclosed. Also disclosed are methods for using these polynucleotides for gene regulation and manipulation of the sugar profile of coffee plants, to influence flavor, aroma, and other features of coffee beans.

14 Claims, 9 Drawing Sheets

OTHER PUBLICATIONS

Leroy, T. et al., "Construction and Characterization of a Coffea Canephora BAC Library to Study the Organization of Sucrose Biosynthesis Genes," *Theoretical and Applied Genetics, International Journal of Plant Breeding Research*, Springer-Verlag, BE, vol. 111(6) Dec. 1, 2005, pp. 1032-1041, XP019322047, ISSN: 1432-2242, relevant to invention 1, the whole document.

Chenwei, Lin et al., "Coffee and Tomato Share Common Gene Repertoires as Revealed by Deep Sequencing of Seed and Cherry Transcripts," *Theoretical and Applied Genetics International Journal of Plant Breeding Research*, Springer-Verlag, BE, vol. 112(1), Dec. 1, 2005, pp. 114-130, XP019322122, ISSN: 1432-2242, relevant to invention 1, the whole document.

Geromel, C. et al., "Biochemical and Genomic Analysis of Sucrose Metabolism During Coffee (Coffea Arabica) Fruit Development," *Journal of Experimental Botany*, vol. 57(12) Sep. 2006, pp. 3243-3258, XP003535505, ISSN: 0022-0957, relevant to inventions 1 and 2, the whole document.

Marraccini, P. et al., "Biochemical and Molecular characterization of Enzyme Controlling Sugar Metabolism During Coffee Bean Development [Abstract S19-14]," *7th International Congress of Plant Molecular Biology*, Jun. 23, 2003, pp. 250-260, XP001249370, Barcelona, relevant to invention 2, the whole document.

Nguyen-Quoc, B. et al., Overexpression of Sucrose Phosphate Synthase Increases Sucrose Unloading in Transformed Tomato Fruit, *Journal of Experimental Botany*, Oxford University Press, GB, vol. 50(335), Jun. 1999, pp. 785-791, XP008062136, ISSN: 0022-0957, relevant to invention 2, the whole document.

Huber, S.C. et al., "Role and Regulation of Sucrose-Phosphate Synthase in Higher Plants," *Annual Review of Plant Physiology and Plant Molecular Biology*, Annual Reviews Inc., xx, vol. 47, 1996, pp. 431-444, XP002298781, ISSN: 1040-2519, relevant to invention 2, the whole document.

Altschul, S. F. et al., "Gapped BLAST and PSI-Blast: A New Generation of Protein Database Search," *Nucleic Acids Res*.25:3389-3402, 1990.

Bäumlein, H. et al. "*Cis*-Analysis of a Seed Protein Gene Promoter: The Conservative RY Repeat CATGCATG Within The Legumin Box Is Essential For Tissue-Specific Expression Of A Legumin Gene," *Plant J*. 2:233-239, 1992.

Benamor, M. and Mc Carthy, J., "Modulation of Coffee Flavour Precursor Levels in Green Coffee Grains," European Patent Application No. 03394056.0, Nestec S.A., 2003.

Carlson, S.J. et al., "Gene Expression Studies on Developing Kernels of Maize Sucrose Synthase (Susy) Mutants Show Evidence for a Third Susy Gene," *Plant Mol Biol*. 49: 15-29, 2002.

Chahan, Y. et al., "From The Green Bean To The Cup Of Coffee: Investing Coffee Roasting By On-Line Monitoring Of Volatiles," *Eur Food Res Technol*. 214:92-104, 2002.

Chourey, P.S. et al., "Tissue Specific Expression and Anaerobically Induced Posttranscriptional Modulation of Sucrose Synthase Genes In *Sorghum bicolou*," *M. Plant Physiol*. 96:485-490, 1991.

Crouzillat, D. et al., "Theobroma *Cacao* L.: A Genetic Linkage Map And Quantitative Trait Loci Analysis," *Theor Appl Genet*. 93: 205-214, 1996.

Echeverria, E. et al., "Physical and Kinetic Evidence for an Association Between Sucrose-Phosphate Synthase and Sucrose-Phosphate Phosphatase," *Plant Physiol*. 115:223-227, 1997.

Foyer, C.H. and Ferrario, S. "Modulation Of Carbon And Nitrogen Metabolism in Transgenic Plants With A View To Improved Biomass Production. In: Lea PJ, Ed. Transgenic Plants and Plant Biochemistry," University of Lancaster: Society/Host Colloqium, vol. 22(4), pp. 909-915, 1994.

Fu, H. and Park, W.D. "Sink- And Vascular Associated Sucrose Synthase Functions Are Encoded By Different Gene Classes In Potato," *Plant Cell*. 7: 1369-1385, 1995.

Galtier, N., et al. "Effects Of Elevated Sucrose-Phosphate Synthase Activity On Photosynthesis, Assimilate Partitioning, And Growth in Tomato (*Lycopersicon esculentum* Var UC82B).," *Plant Physiol*. 101:535-543, 1993.

Holscher, W. and Steinhart, H. 1995, Aroma Compounds in Green Coffee,. Elsevier, 785-803.

Huang J.W. et al., "Complete Structures Of Three Rice Sucrose Synthase Isogenes And Differential Regulation Of Their Expressions.," *Biosci. Biotechnol. Biochem*. 60: 233-239, 1996.

Huber, S.C. and Huber, J.L. "Role and Regulation Of Sucrose-Phosphate Synthase in Higher Plants," *Annu. Rev. Plant Physiol. Plant Mol. Biol*. 47: 431-444, 1996.

Huber, S.C. et al., "Light Regulation Of Sucrose Synthsesis: Role Of Protein Phosphorylation And Possible Involvement Of Cytosolic $Ca^{2+}$. Carbon Partitioning And Source-Sink Interactions In Plants," ed. MA Madore, W Lucas, pp. 35-44. Rockville, MD: *Am. Soc. Plant Physiol.*, 1995.

Jones, T.L. and Ort, D.R. "Circadian Regulation Of Sucrose Phosphate Synthase Activity In Tomato By Protein Phosphatase Activity," *Plant Physiol*. 113:1167-1175, 1997.

Lafta, A.M. and Lorenzen, J.H. "Effect Of High Temperature On Plant Growth And Carbohydrate Metabolism In Potato," *Plant Physiol*. 109:637-643, 1995.

Laporte, M.M. et al.,"Sucrose-Phosphate Synthase Activity And Yield Analysis Of Tomato Plants Transformed With Maize Sucrose-Phosphate Synthase," *Planta*. 203: 253-259, 1997.

Locher, R., and Bucheli, P. "Comparison Of Soluble Sugar Degradation In Soybean Seed Under Simulated Tropical Storage Conditions," *Crop Sci*. 38. 1229-1235, 1998.

Lunn, J.E. and Macrae, E. 2003. "New Complexities in the Synthesis of Sucrose," Curr Opin Plant Biol. 6: 208-214, 2003.

Marraccini, P. et al., "Molecular Cloning Of The Complete 11S Seed Storage Protein Gene Of *Coffea arabica* and Promoter Analysis in the Transgenic Tobacco Plants," *Plant Physiol. Biochem*. 37:273-282, 1999.

Marraccini, P. et al., "Rubisco Small Subunit of *Coffea arabica*: CDNA Sequence, Gene Cloning And Promoter Analysis In Transgenic Tobacco Plants," *Plant Physiol. Biochem*. 41:17-25, 2003.

McMichael, R.W. et al., "Identification of the Major Regulatory Phosphorylation Site in Sucrose Phosphate Synthase," *Arch. Biochem. Biophys*. 321:71-75. 1993.

Micallef, B.J. et al., "Altered Photosynthesis, Flowering And Fruiting In Transgenic Tomato Plants That Have An Increased Capacity For Sucrose Synthesis," *Planta*. 196:327-334, 1995.

N'Tchobo, H. et al., "Starch Synthesis In Tomato Remains Constant Throughout Fruit Development And Is Dependent On Sucrose Supply And Sucrose Activity," *J. Exp. Bot*. 50. 1457-1463, 1999.

Nguyen-Quoc, B. et al., "Overexpression Of Sucrose-Phosphate Synthase Increases Sucrose Unloading In Transformed Tomato Fruit," *J. Exp. Bot*. 50: 785-791, 1999.

Nguyen-Quoc, B. and Foyer, C.H., "A Role for 'Futile Cycles' Involving Invertase And Sucrose Synthase In Sucrose Metabolism Of Tomato Fruit," *J. Exp. Bot*. 52:881-889, 2001.

Robinson, N. L. et al., "Sink Metabolism in Tomato Fruit," *Plant Physiol*,. vol. 87:727-730, 1988.

Rogers, W. J. et al., "Changes To The Content Of Sugars, Sugar Alcohols, Myo-Inositol, Carboxylic Acids And Inorganic Anions In Developing Grains From Different Varieties Of Robusta (*Coffea canephora*) And *arabica* (*C. arabica*) Coffees," *Plant Sc*. 149:115-123, 1999.

Russwurm, H., "Fractionation And Analysis Of Aroma Precursors In Green Coffee," ASIC 4: 103-107, 1969.

Sugden, C. et al., "Two SNF1-Related Protein Kinases From Spinach Leaf Phosphorylate And Inactivate 3-Hydroxy-3-Methylglutaryl-Coenzyme A Reductase, Nitrate Reductase, And Sucrose Phosphate Synthase In Vitro," *Plant Physiol* 120:257-274, 1999.

Sun, J. et al., :Sucrose Synthase In Wild Tomato, Lycopersicon Chmielewskii, And Tomato Fruit Sink Strength, *Plant Physiol*. 98: 1163-1169, 1992.

Toroser, D. and Huber, S.C. "Protein Phosphorylation As A Mechanism for Osmotic-Stress Activation Of Sucrose-Phosphate Synthase In Spinach Leaves," *Plant Physiol*. 114:947-955, 1997.

Trevanion, S.J. et al., "Regulation Of Sucrose-Phosphate Synthase in Wheat (*Triticum aestivum*) Leaves," *Functional Plant Biology*. 31:685-695, 2004.

Van Assche, C. et al., "Modification Of Sucrose Phosphate Synthase In Plants," United States Patent No. 5,981,852, 1999.

Wang, F. et al., "Sucrose Synthase Starch Accumulation And Tomato Fruit Sink Strength," *Plant Physiol* 101:321-327, 1993.

Wang, F. et al., "Temporal And Spatial Expression Pattern Of Sucrose Synthase During Tomato Fruit Development," *Plant Physiol* 104:535-540, 1994.

Worrell, A.C. et al., "Expression Of A Maize Sucrose Phosphate Synthase In Tomato Alters Leaf Carbohydrate Partitioning," *Plant Cell* 3:1121-1130, 1991.

Zrenner, R. et al., "Evidence Of Crucial Role Of Sucrose Synthase For Sink Strength Using Transgenic Potato Plants (*Solanum tuberosum* L.)," *Plant J.* 7:97-107, 1995.

FIG. 2A

```
CcSS2    SKFDEKYHFSCQFTADLIAMNHTDFIITSTFQEIAGSKDTVGQYESHMAFTMPGLYRVVHGIDVFDPKFNIVSPGADTNLYYPHTEKEKR  540
SuSyLE2  KKFDEKYHFSSQFTADLIAMNHTDFIITSTFQEIAGSKDTVGQYESHMAFTMPGLYRVVHGINVFDPKFNIVSPGADTNLYFPYSESEKR   540
SuSyST2  NKFDEKYHFSAQFTADLIAMNHTDFIITSTFQEIAGSKDTVGQYESHMAFTMPGLYRVVHGIDVFDPKFNIVSPGADVNLYFPYSEKEKR   540
SuSyST4  KKFDEKYHFSSQFTADLIAMNHTDFIITSTFQEIAGSKDTVGQYESHMAFTMPGLYRVVHGINVFDPKFNIVSPGADTNLYFSYSETEKR   540

CcSS2    LTSFHPEIEELLFSDVENEEHLCVLKDKKKPILFTMARLDRVKNLTGLVELYAKNPKLRELVNLVVVGGDRRKESKDLEEQAEMKKMYSL   630
SuSyLE2  LTAFHPEIDELLFSDVENDDHLCVLKDRTKPILFTMARLDRVKNLTGLVEWYAKNPRLRGLVNLVVVGGDRRKESKDLEEQAEMKKMYEL   630
SuSyST2  LTTFHPEIEDLLFSDVENEEHLCVLKDRRNKPITFTMARLDRVKNLTGLVEWYAKNPRLRELVNLVVVGGDRRKESKDLEEQAEMKKMYEL   630
SuSyST4  LTAFHPEIDELLFSDVENDEHLCVLKDRTKPILFTMARLDRVKNLTGLVEWYAKNPRLRGLVNLVVVGGDRRKESKDLEEQAEMKKMYEL   630

CcSS2    IETYNLNGQFRWISSQMNRVRNGELYRYIADTKGAFVQPAFYEAFGLTVVEAMTCGLPTFATNHGGPAEIIHGKSGFHIDPYHGEQVSE   720
SuSyLE2  IETHNLNGQFRWISSQMNRVRNGELYRYIADTKGAFVQPAFYEAFGLTVVEAMTCGLPTFATNHGGPAEIVHGKSGFHIDPYHGEQAAD   720
SuSyST2  IKTHNLNGQFRWISSQMNRVRNGELYRYIADTRGAFVQPAFYEAFGLTVVEAMSCGLPTFATNQGGPAEIVHGKSGFQIDPYHGEQAAD   720
SuSyST4  IETHNLNGQFRWISSQMNRVRNGELYRYIADTKGAFVQPAFYEAFGLTVVEAMTCGLPTFATNHGGPAEIVHGKSGFHIDPYHGEQAAD   720

CcSS2    LLANFFERCKKEPSYWDTIPAGGLKRIQEKYTWQIYSDRLLTLAGVYGFWKCVSKLDRQEIRRYLEMFYALKYRKLAEAVPLAVDQ.    807
SuSyLE2  LLADFFEKCKKEPSHWETISTGGGLKRIQEKYTWQIYSERLLTLAAVYGFWKHVSKLDREIRRYLEMFYALKYRKMAEAVPLAAE      805
SuSyST2  LLADFFEKCKVDPSHWEAISBGGLKRIQEKYTWQIYSERLLTLAAVYGFWKHVSKLDREIRRYLEMFYALKYRKLAQLVPLAVE       805
SuSyST4  LLADFFEKCKKEPSHWETISTGGGLKRIQEKYTWQIYSERLLTLAAVYGFWKHVSKLDREIRRYLEMFYALKYRKMAEAVPLAAD      805
```

```
CcSP1   MDRLADAAHLMIVSDLDHTMVDHHDPENMSLLRFNALWEANYRDNSLLVFSTGRSPTLYKELRKEKPMLTPDITIMSVGTEITYGNAMVP    90
SPAT1   MERLTSPPRLMIVSDLDHTMVDHHDPENLSLLRFNSLWEHAYRHDSLLVFSTGRSPTLYKELRKEKPLTPDITIMSVGTEITYGNSMVP    90
SPLE    MDRLTSAARLMIVSDLDHTMVDHHDSENLSLLRFNALWEANYRDNSLLVFSTGRSPTLYKELRKEKPMLTPDITIMSVGTEITYGNAMVP   90

CcSP1   DDGWVEFLNQKWDRKIVTEETSKFPELTLQSHTEQRPHKVSFYVQKDKAQDVIKALAARLEERGLDVKIIYSGGMDLDILPQGAGKGQAL  180
SPAT1   DHGWVEALNNKWDLGIVKQEASNFPELKLQAETEQRPHKVSFYVEKSKAQEVTKELSQRFLKRGLDVKIIYSGGMDLDILPQGAGKGQAL  180
SPLE    DDGWETFLNNKWDRKIVTEETSKFPELSLQSETEQRPHKVSFYVQKEKAQDIMKTLSKRLKERGLDVKIIYSGGMDLDILPQGAGKGQAL  180

CcSP1   AYLLKKFKAEGKSPNNTLVCGDSGNDAELFSIPEVYGVMVSNAQEELLQWHAANAKDNSKIIHATERCAAGIIQAIGHFNLGPSVSPRDV  270
SPAT1   AYLLKKEKTEGKLPVNTLACGDSGNDAELFSIPDVYGVMVSNAQEELLKWHAENAKDNPKVIHAKERCAGGIIQAIGHFKLGPNISPRDV  270
SPLE    AYLLKKEKSEGKLPSNTLACGDSGNDAELFSIPDVYGVMVANAQEELLQWHAANAKNNPKVIHASERCAAGIIQAIGHFNLGPSTSPRDV  270

CcSP1   TDLSDSKLEDFDPAYEVVKFNLFFERWRRAEVEKSELYLANMKAVCCPSGVLVHPSGIEKLLGDCVNAFRTCYGDQQGKSYRVWVDQVLP  360
SPAT1   SDFLEIKVENVNPGHEVVKFLFYERWRRGEVENSEAYTASLKASVHPGGVFVHPSGTEKSLRDTIDELRKYHGDKKQGKKFRVWADQVLA  360
SPLE    TDLSDCKMDNFVPAYEVVKFYLFFEKWRRGEIEHSEHYLSNLKAVCRPSGTFVHPSGVEKSLQECVTTFGTCHADKHGKQYRVWVDQVLP  360

CcSP1   TQVGSDSWLVKYKKWELSGEKQKGCLTTVLLSSKGVSVPEGLTWVHVHQTWLDGAGPTDDSSWFF                           425
SPAT1   TDTTPGTWIVKLDKWEQDGDERRCTTTVKFTSKE---GEGLVEHVQQTWSKETMVKDDSSWII                           422
SPLE    SQVGSDSWLVSFKKWELSGENRRCCITTVLLSSKNKTVADGLTWTHVHQTWLHDDASSDSASWFF                         425
```

FIG. 5

SEQUENCE LISTING

<160> NUMBER OF SEQ ID NOS: 46

<210> SEQ ID NO 1
<211> LENGTH: 3048
<212> TYPE: DNA
<213> ORGANISM: Coffea canephora

<400> SEQUENCE: 1

```
ccttaagagt ggaacaacgc agagtacgcg gggagagctg aattcattca tctctctttt      60
tcgtatactc tgttactctt ttttcttttt tctttcgttt ctctgtttct tgctctttat     120
ttcttaggag ggggctccat tgggctctct ctctctctct ctccacgt tcaatccagt       180 gctagctact ttttctcctg tgagttgaaa cctgtctgag atttcgttgg tcgatccatc     240
aactgccatg gccgaacgtg ttctgacccg tgttcacagc ctccgtgaac gccttgatgc    300
tactttggct gcccaccgca acgatgtttt gctgtttatg tcgaggcttg aaacccatgg    360
gaaagggatc ctgaaacccc accaactttt ggctgagttt gaagaaatta caaggatgg     420 taaacaaaaa attcatgatc atgcctttga agaagtcctg aagtccacac aggaagcaat    480
tgtgttgccc ccctgggttg cacttgctat tcgtctcaga cctggtgtct gggagtatgt    540
tcgagtcaat gtccatgcac tcgttgttga ggagttaacc gtgccagagt acctgcattt    600
caaggaagaa ctcgttgatg gaagcaaaaa tgggaatttt gttttggaac tggacttcga    660
accatttaca gcatcttttc ccaagccaac tctaactaag tacataggtg acggagttga    720
gttcctcaac aggcacctct ctgccaaaat gttccatgac aaggagagca tggcccctct    780
ccttgatttt ctccgtgttc accaatacaa gggcaagacg atgatgctta acgacaggat    840
caaggacctt aacactctcc aagcagttct gaggaaggca gaggagtacc taacaacact    900
ctctgcagat acaccatact ctgaattcga gcacaaattc caagaaattg gactggagag    960 aggttgggt gatactgctg agcgtgtctt ggaaatgatc tgcatgcttc tggatcttct    1020
ggaggctcct gactcgtgca cactagagaa attcctaggg agaatccota tggtattcaa   1080 tgttgttatt ctttccccccc atggatactt tgcccaggaa aacgtattgg gttatcctga   1140
taccggtggc caggttgttt acatattgga tcaagttcct gccttggagc gtgagatgct    1200
gaagaggata aaggaacaag gacttgatgt caagccacgc attctaatta taactaggct    1260
gctacctgat gcccctggaa ccacttgtgg tcaacggctt gagaaagtat acggatcaga    1320
gtactcccat atactcagag tccccttcag aactgagaag ggcgttgttc gcaaatggat    1380
ctctcgcttt gaagtttggc cctacatgga aacatttact gaggatgttg caaaagaagt    1440
cactgcagaa ttacaggcaa agccagattt ggttattggt aactacagtg agggtaacct   1500
tgttgcctcc ttgcttgctc acaagttagg tgtaacacag tgtaccattg ctcatgcttt    1560
ggaaaaaacc aagtatcctg attctgatat ttatttgagc aaatttgatg agaagtacca   1620
```

| | |
|---|---|
| cttctcatgc cagttcactg cggatcttat cgcaatgaac catacagatt tcattatcac | 1680 |
| tagcacttc caagaaatag ctggaagcaa ggacactgtt gggcaatatg aaagccatat | 1740 |
| ggccttcaca atgccaggat tatacagagt tgtgcatggc attgatgttt ttgatccaaa | 1800 |
| attcaacatt gtctcacctg agctgatac aaacctctac tacccacaca cagagaagga | 1860 |
| aaagagattg acatccttcc atcctgaaat tgaggagttg cttttcagcg atgtggagaa | 1920 |
| tgaggaacac ctatgtgtgc taaaagacaa aaagaagcct atcttattca ccatggcaag | 1980 |
| actggatcgc gtaaagaatt tgacagggct tgttgaattg tatgctaaga acccaaaact | 2040 |
| aagggaattg gttaatcttg tcgtggttgg tggagaccga aggaaggaat ccaaagattt | 2100 |
| ggaagaacaa gctgagatga agaaaatgta ttcattgata gagacttaca acttgaacgg | 2160 |
| ccaattcaga tggatttctt ctcagatgaa cagggttaga aatggtgaac tctatcggta | 2220 |
| cattgctgac accaagggag cattcgtgca acctgcattt tatgaggcat ttgggttgac | 2280 |
| tgtggtcgag gccatgacat gtggtttgcc aacgttgca accaaccatg gtggtcctgc | 2340 |
| tgagatcatt attcatggga aatctggttt ccacattgat ccataccacg gtgagcaggt | 2400 |
| cagcgagctc cttgccaatt tcttcgaaag gtgcaagaaa gagccttctt actgggacac | 2460 |
| cattccagcc ggtggcttga agcgtatcca ggaaaagtac acctggcaaa tttactcaga | 2520 |
| tcggttgctg acgctggctg gagtttatgg attctggaaa tgtgtttcca gcttgatcg | 2580 |
| ccaggagatc cgccgttatc tggaaatgtt ttatgctctc aagtatcgca gttggctga | 2640 |
| agctgttcca ttggctgttg atcagtaaga gtttgcggca gaaaagttg gaagcagcgg | 2700 |
| gagggagaca ataaaataa aagagcttga ggtcgtgtaa aagaagagg attgtgttt | 2760 |
| tgttacttct gccagtcttg cctttcttta ttgttggttg gttgtgtctt tttagtccct | 2820 |
| gttcaagtgt caattaggtc cttcttgtag gtcattttcg ttgggttgtt tgccatttcc | 2880 |
| tttctttc ctgcttttg gtagtgcgag gaattgggca tttccaaatg tcattttgta | 2940 |
| ataagatcaa tttaccttcc atttcgacat tattatttt ttattttggg gcaaaaaaaa | 3000 |
| aaaaaaaaaa aaaaaaaaaa aagtctctgc gtgttccgaa tcttaagg | 3048 |

<210> SEQ ID NO 2
<211> LENGTH: 3150
<212> TYPE: DNA
<213> ORGANISM: Coffea canephora

<400> SEQUENCE: 2

| | |
|---|---|
| atggcgggaa atgactggat aaacagttac ttggaggcga tattagatgt gggaccaggg | 60 |
| attgatgatg ccaagtcgtc actgctgctc agagaaagag ggaggttcag cccaactcgt | 120 |
| tacttcgtgg aggaggtcat taccggcttt gatgagaccg atctccaccg ctcttgggcc | 180 |
| cgcgcgcaag cgacccggag tccgcaagag aggaatacca ggcttgagaa tttgtgctgg | 240 |
| cgtatttgga atttggctcg ccagaaaaag cagcttgagg gagagcaagc tcagaggatg | 300 |
| gcgaaacgcc gtcttgaacg tgaaaggggc cgcagagaag cagttgctga tatgtctgaa | 360 |
| gacttatcag aggggggagga aggagataca gttggtgact ttttggcaca tggtgagagc | 420 |
| aatagggggtc gattgcccag aataagctct gttgaaacaa tggaagcatg gctagtcaa | 480 |
| cagaaggaaa agaagtggta tattgtattg ataagccttc atggactgat tcgtggcgaa | 540 |
| aacatggagc ttggacggga ttctgatact ggtggtcagg tgaagtatgt agtcgaactt | 600 |
| gcaagggctt taggttcaat gccaggtgta tatcgggttg atttacttac gaggcaggta | 660 |
| tcatcactgg aagtagattg gagttacggt gaacccactg agatgctgcc tcctagaaat | 720 |

```
tcagaaggtt taaatgagat gggggagagc agtgggcgtt atattattcg cattccttt    780
ggccctagag acaaatacat tcctaaggag cttctgtggc cttacctttc tgaatttgtt    840
gatggtgcac ttagccatat aatccagatg tccaaagttc ttggtgagca agttggtggt    900
ggacatcctg tctggcctgt tgctattcat ggacattatg cagatgctgg tgattctgca    960
gctcttctgt ctgggctct aaatgttccc atgcttttca ctggtcattc ccttggtcga   1020
gataagttgg agcaactttt gagacagggt agactgtcaa gggacgaaat aaattctacg   1080
tacaaaataa tgcgcaggat agaggcagag gagatatcac ttgatgcctc tgaaactgtc   1140
ataacaagca caagacagga gattgaggag caatggcgtt tatatgatgg ctttgatcca   1200
atcctgggaa ggaaattgcg ggctaggatc aggcgcaatg ttagctgtta tggcagattc   1260
atgcctcgaa tggctgtaat tcctcctggg atggagttcc atcacattgt cccacatgat   1320
ggtgacatgg atggtgagat ggaaggaaat gaggatggaa agtctccgga tccacatatt   1380
tggggagaga taatgcgcta cttcacaaat ccacgaaagc ctatgatact agcccttgcc   1440
aggccagatc ccaaaaagaa cctaatgaca ttggtcaaag catttggtga atgtcgtcca   1500
cttcaagaac ttgctaacct tacattgata atggggaacc gtgatgatgt tgatgaaatg   1560
tcaagcacta gtgcttctgt tctactttca atactaaagt tgatagacaa gtatgatctt   1620
tatggtcaag tggcatatcc aaaacatcac aagcagtccg atgttcctga catataccgt   1680
cttgcagcaa agacgaaggg tgttttatt aatccagctt tcatcgagcc ttttggactt   1740
actttaatag aggcagcagc tcacggtttg ccaattgttg caactagaaa tggtggtcct   1800
gtcgacatac acagggttct tgacaacggt cttcttgttg atccacataa tcagcagtcc   1860
attgctgatg ctcttttgaa gctggttgct gacaagcaac tttggtcaaa atgcagggca   1920
aatggattaa aaaacattca ccttttctca cggcctgaac attgtaaaac atatttaact   1980
aagatagcaa gttgcaaacc aaggcaacca agatggttga aaatgatga tgatgatgaa   2040
aattcagaat ctgattcacc taatgattcc ttaagagata tacaggatat atctttgaat   2100
ttgaagtttt cacttgatgg ggataaaaac gtgggtaagg aaaatggtga tgggtctttg   2160
gatcttgatg atcgaaaaag caagttagaa actgcagttt tgagttggtc caggggcgtg   2220
cagaagacta cccagaaatc tggttccaca gacaaaggtg accaaaactc tggtgctggt   2280
aagttcccag cactcaggag gaggaaatac atgtttgtaa ttgcagtgga ttgtggtgcc   2340
cttttcagaaa gtgtcaaaag gattttttgat gctttggaga aggaaaaggc agaaggctct   2400
ataggattta tattagccac atcttttaac ttgtcagaac tacattcttt tctggtttca   2460
gagcgtctga atccattga ttttgatgct tttatttgca acagtggtgg tgatctttat   2520
tattcatcac ttcactctga tgagaaccct ttcatagttg acttgtatta ccattcacat   2580
attgaatacc gctggggtgg tgaagggttg aggaagacat tggtgcggtg ggcggcctca   2640
attactgata agaagggcga tgacaaagaa cacattgtgg ttgaagatga aaagaactca   2700
gctgactact gctattcgtt taagttttgc aggccaggag tggttcctcc agtgagggaa   2760
ctcaggaaag taatgaggat tcaggctctt cgttgtcatg tgatttattg tcaaaacggg   2820
agtaagatta atgtcattcc agtgctagca gctcgttgcc aggcactcag gtacctgtat   2880
cttcgatggg gtatggattt tgtcaaaagtg gtggttttg ttggagaaag tggggacact   2940
gattatgaag gattacttgg tggtgtgcac aagtctgtga tactgaaagg agtttgcagt   3000
ggagaaagca gccaacttca tgccaacaga agctacccac ttaccgatgt ggtggcattt   3060
gacaatccga accttattca gacgagtgaa gactgcagca gtgctgagct gcgcgagtcg   3120
```
ttggaaaagc tagggggttct caaaagctag                                    3150

<210> SEQ ID NO 3
<211> LENGTH: 1648
<212> TYPE: DNA
<213> ORGANISM: Coffea canephora

<400> SEQUENCE: 3
gttatcctcc aggtggtgaa cgtctcatcc tcctcctgcg aactcatcct tcctccccta     60
tccgacccat cgcctccgcc gcgtcccttc ctccccctcc tactccgaac gaagttcaca    120
ttaaagtcac catggatcgg cttgctgacg ctgcacatct aatgatagtc tcagatcttg    180
accacacaat ggttgatcat cacgatcctg agaatatgtc tctgcttagg tttaatgcct    240
tgtgggaagc caactatcga gacaattctc tgctagtatt ctcaactggg aggtcaccta    300
cactgtacaa ggagttgcgg aaagagaagc ctatgctgac cccagatatt accatcatgt    360
ctgtagggac tgaaatcaca tacggcaatg ctatggtgcc tgatgatggc tgggttgaat    420
ttctaaacca gaaatgggat agaaagatag ttacagaaga gacgagcaag tttccagagc    480
ttactcttca gtcacacacg gagcaacgac cacacaaggt tagcttttat gttcagaagg    540
ataaagctca agatgtaatt aaagcacttg ctgcacggct ggaagaacgc gggttggatg    600
ttaaaataat ttacagtgga gggatggatt tggatatatt accacaaggt gcaggcaaag    660
ggcaagcact tgcttatttg cttaaaaaat tcaaggctga gggtaaatca cctaacaaca    720
cgcttgtttg tggagactct gggaatgacg ctgaactatt tagcataccct gaagtatatg    780
gcgtcatggt cagtaacgcc caggaagaat tgttgcaatg gcatgcggct aatgctaaag    840
ataattctaa gatcattcat gcaactgaga ggtgtgcagc gggtatcata caagccattg    900
gccatttttaa cctcggtccc agtgtatctc caagagatgt cacagacttg tccgattcta    960
agttggagga cttttgatcct gcttatgaag tagtgaaatt taacttgttc tttgaaagat   1020
ggagacgtgc agaagttgaa aagtctgagc tttatttggc aaacatgaaa gcagtctgtt   1080
gtccatctgg tgtgcttgtt catccatcag ggattgaaaa acttcttggt gactgtgtaa   1140
atgcatttag gacctgctat ggtgaccaac agggaaaaag ttatcgggtt tgggtggatc   1200
aggttttgcc aacacaggtt ggttcagact cttggctagt gaagtacaag aaatgggagt   1260
tatctggtga aaaacagaag ggttgcttga cgacagtttt attgagttca aagggtgtca   1320
gtgtcccaga agggcttact tgggtgcatg tccatcagac gtggttggat ggagctgggc   1380
caactgatga ttcatcctgg ttttttttaag ccgcgggcgt gcttagcctt attacaagaa   1440
cccgacagcc tacacgtctt tgttaaaaca aatttgaaat cccggtgata ggtgattttt   1500
tttttttaact gtcccctgaa gaattatgta ttgccattcc ctgagaatt tatgtattgc   1560
ctttggacgg tatgaagatg gctgactagc tgcttccgct taaaaaaaaa aaaaaaaaa    1620
aaaaaaaaaa aaaaaaaaa aaactcga                                      1648

<210> SEQ ID NO 4
<211> LENGTH: 1937
<212> TYPE: DNA
<213> ORGANISM: Coffea canephora

<400> SEQUENCE: 4
gattctgata cgggtggtca ggtatatttg gttataagat cctgtttatc atgtactaag     60
cctagtccca ttcattgaat gattgctaga cagcattttc tggtagtttt tgcgctctca    120
tagttgctca aggaatctta ggtaaggtac ttcattaaaa ttttgtttcg ttttttggtaa   180

```
cctagctgct tatccaaaag aagtgagtaa gacactggga tccatgcatt tcaggtgaag      240
tatgtagtcg aacttgcaag ggctttaggt tcaatgccag gtgtatatcg ggttgattta      300
cttacgaggc aggtatcatc actggaagta gattggagtt acggtgaacc cactgagatg      360
ctgcctccta gaaattcaga aggtttaaat gagatggggg agagcagtgg ggcttatatt      420
attcgcattc cttttggccc tagagacaaa tacattccta aggagcttct gtggccttac      480 cttctgaat ttgttgatgg tgcacttagc catataatcc agatgtccaa agttcttggt       540
gagcaagttg gtggtggaca tcctgtctgg cctgttgcta ttcatggaca ttatgcagat      600
gctggtgatt ctgcagctct tctgtctggg gctctaaatg ttcccatgct tttcactggt      660
cattcccttg gtcgagataa gttggagcaa cttttgagac agggtagact gtcaagggac      720
gaaataaatt ctacgtacaa aataatgcgc aggatagagg cagaggagat atcacttgat      780
gcctctgaaa ctgtcataac aagcacaaga caggagattg aggagcaatg gcgtttatat      840
gatggctttg atccaatcct gggaaggaaa ttgcgggcta ggatcaggcg caatgttagc      900
tgttatggca gattcatgcc tcgaatggct gtaagttttc attttgctt ggaactatac       960 tggctgatga agttacattt tatctgttta atgtttgtaa accacaaaat ctttgtttgt     1020
ttattcaatt attgtataat tttttactac gattgagatc aaatgttgag tttggtggaa     1080
gacactgctg gttttcttaa atttgctttt caactttgcc tatacatgtt aagttggata     1140 cttttctgc ttaagcgagt tgtacttgac taagctaagg ttgaaaagat gctatgcact       1200
tcgagtctag tatattcctt attttgtag aataatgtat atagactcct gttgctcctt      1260
gtcaagtata aatattttgt agcagcgtct gccttcgttg actccttgc tgattccttt       1320 tttttcttg ctgcttctgc aattgcattt cctgaatttg cttgatttat gaccctggtt       1380
gtaactatta gtcaccatat atcattttaa ttcttgagag atgaagcatg caacaaatta     1440
gaattgctca tggacttata agttatctca tgtattaagc tctcataatt ctttctgata     1500
ttggatcaaa ttttttgagag ttggttgatc agattggctc ctttctaaga tcagctggaa    1560
agtgaagtat caagtccttt atgtgatata catatttctt ttgcaggtaa ttcctcctgg     1620
gatggagttc catcacattg tcccacatga tggtgacatg gatggtgaga tggaaggaaa     1680
tgaggatgga aagtctccgg atccacatat ttggggagag gtcttaattt tcttgataat     1740
acctaatctg cagctgcatt cctcttaatt ttgttcattt atttctttct cctttttgctg    1800 ttatgcaagt tctcttttttg tggtgtcatg cagataatgc gctacttcac aaatccacga    1860
aagcctatga tactagcccct tgccaggcca gatcccaaaa agaacctaac gacattggtt    1920
aaagcttttg gtgaatg                                                   1937
```

<210> SEQ ID NO 5
<211> LENGTH: 1564
<212> TYPE: DNA
<213> ORGANISM: Coffea canephora

<400> SEQUENCE: 5

```
ggtgggacac gggtggccag gtaagatcag cattcaagaa aaactagaac tccttttacc       60
agtcaactct catcttattt ggcctgacct gctttcatga aaaatgcca gattaaatat        120 gttgttgagc ttgctaaggc acttgctaag atgccaggtt tttatcgggt tgatctgttc       180
accaggcaaa tctcctctcc agaagtagat tggagctatg gggagcccac agagacgcta      240
aatactggtc ccgaagatgg tgatggtgcc gatttgggaa aaagctgtgg ggcttacatt      300
ataaggatgc catttggtcc tcgtgacaag tacctaagga aagaattact gtggcctcat      360
```

-continued

```
cttcaagagt tgtagatgg ggcgctagct cacatcctta atatgtcgaa agttttaggt      420
gaacaaattg gaggtggaca tcctgtttgg ccttatgtaa ttcatgggca ttatgcagat      480 gcagggata gtgctgctct tctttcgggt gcttaaacg ttccgatggt tctgacaggg      540
cactcactcg gtagaaacaa gctagaacaa cttctgaaac aaggaaggca atcaaaagag      600
gacattaatt ctacatacaa aattatgcgt aggatagaag cagaagaact ttcacttgat      660
gctgcagaac ttgttattac aagcaccaag caggagattg atgaacagtg gggactatat      720
gatggatttg atgtaaagct tgagaaagtt ttgagggccc gtgcaagaag aggggtcaat      780
tgccatggtc gctacatgcc aaggatggcg gtaagcatat tgttgagaaa ttaaattgat      840
gtgctattgc tttagctgaa acttgtgcat tagtgttggt tcttaaaata agcaaagcaa      900
tttagatagt cattgcttct ttgtttttt gttcaactaa agtaattccc tggaatggta      960
agctactatg acaaggctca ttactccagt gcagtaatgg ttttaattg atagcatgcc     1020 tctttgagg aacttagaag atttcattag acatgtacct ttgttattc ctattaagca     1080 ctagtatggc agttggctgt tgtcagcgag actatgattt tcactgaggt tcttgaattc     1140
tgcagccagg agagcatcat gagaaagtct agacatctgc tcaagtgtat atacatttat     1200
gaaggttcta atatctgcta gttttagcta catttttcag ttatccctc ctgggatgga     1260 cttcagcaat gtcatagcac aagaagacac agccgaagtc gatggtgaac ttgtagcact     1320
aaccaatggt gatggtgctt cacctaaagc actccctcca atatggtcag aagtgagtag     1380
gtggttttca taactgattt tgctcttatc tgggaatgtt taccttgcat cgtagtaact     1440
gttttgacag gtaatgcggt ttctcacaaa tccccacaag ccaatgattc tagcattgtc     1500
aagaccagat ccaagaaaa atattaccac acttgttaaa gcttttgggg aatgtctcca     1560
aagg                                                                1564
```

```
<210> SEQ ID NO 6
<211> LENGTH: 8247
<212> TYPE: DNA
<213> ORGANISM: Coffea canephora
<220> FEATURE:
<221> NAME/KEY: 5'UTR
<222> LOCATION: (1)..(308)
<220> FEATURE:
<221> NAME/KEY: exon
<222> LOCATION: (309)..(491)
<223> OTHER INFORMATION: exon 1
<220> FEATURE:
<221> NAME/KEY: intron1
<222> LOCATION: (492)..(618)
<220> FEATURE:
<221> NAME/KEY: exon
<222> LOCATION: (619)..(708)
<223> OTHER INFORMATION: exon 2
<220> FEATURE:
<221> NAME/KEY: intron2
<222> LOCATION: (709)..(1723)
<220> FEATURE:
<221> NAME/KEY: misc_difference
<222> LOCATION: (1604)..(1604)
<223> OTHER INFORMATION: SNP 1R = A or G (silenced)
<220> FEATURE:
<221> NAME/KEY: exon
<222> LOCATION: (1724)..(1963)
<223> OTHER INFORMATION: exon 3
<220> FEATURE:
<221> NAME/KEY: misc_difference
<222> LOCATION: (1771)..(1771)
<223> OTHER INFORMATION: SNP 2Y = T or C (silenced)
<220> FEATURE:
<221> NAME/KEY: intron3
<222> LOCATION: (1964)..(2211)
```

```
<220> FEATURE:
<221> NAME/KEY: exon
<222> LOCATION: (2212)..(2277)
<223> OTHER INFORMATION: exon4
<220> FEATURE:
<221> NAME/KEY: misc_difference
<222> LOCATION: (2268)..(2268)
<223> OTHER INFORMATION: SNP 3K = T or G (silenced)
<220> FEATURE:
<221> NAME/KEY: intron4
<222> LOCATION: (2278)..(2490)
<220> FEATURE:
<221> NAME/KEY: misc_difference
<222> LOCATION: (2331)..(2331)
<223> OTHER INFORMATION: SNP 4Y = C or T (silenced)
<220> FEATURE:
<221> NAME/KEY: misc_difference
<222> LOCATION: (2369)..(2369)
<223> OTHER INFORMATION: SNP 5Y = T or C (silenced)
<220> FEATURE:
<221> NAME/KEY: misc_difference
<222> LOCATION: (2403)..(2403)
<223> OTHER INFORMATION: SNP 6R = A or G (silenced)
<220> FEATURE:
<221> NAME/KEY: misc_difference
<222> LOCATION: (2459)..(2459)
<223> OTHER INFORMATION: SNP 7R = A or G (silenced)
<220> FEATURE:
<221> NAME/KEY: misc_difference
<222> LOCATION: (2478)..(2478)
<223> OTHER INFORMATION: SNP 8Y = T or C (silenced)
<220> FEATURE:
<221> NAME/KEY: exon
<222> LOCATION: (2491)..(3189)
<223> OTHER INFORMATION: exon5
<220> FEATURE:
<221> NAME/KEY: intron5
<222> LOCATION: (3190)..(3865)
<220> FEATURE:
<221> NAME/KEY: exon
<222> LOCATION: (3866)..(3976)
<223> OTHER INFORMATION: exon6
<220> FEATURE:
<221> NAME/KEY: intron6
<222> LOCATION: (3977)..(4089)
<220> FEATURE:
<221> NAME/KEY: exon
<222> LOCATION: (4090)..(4221)
<223> OTHER INFORMATION: exon7
<220> FEATURE:
<221> NAME/KEY: misc_difference
<222> LOCATION: (4157)..(4157)
<223> OTHER INFORMATION: SNP 9R = A or G (silenced)
<220> FEATURE:
<221> NAME/KEY: misc_difference
<222> LOCATION: (4176)..(4176)
<223> OTHER INFORMATION: SNP 10Y = T or C (silenced)
<220> FEATURE:
<221> NAME/KEY: misc_difference
<222> LOCATION: (4182)..(4182)
<223> OTHER INFORMATION: SNP 11W = T or A (silenced)
<220> FEATURE:
<221> NAME/KEY: intron7
<222> LOCATION: (4222)..(4313)
<220> FEATURE:
<221> NAME/KEY: exon
<222> LOCATION: (4314)..(4490)
<223> OTHER INFORMATION: exon8
<220> FEATURE:
<221> NAME/KEY: intron8
<222> LOCATION: (4491)..(5186)
<220> FEATURE:
<221> NAME/KEY: exon
<222> LOCATION: (5187)..(5240)
<223> OTHER INFORMATION: exon9
<220> FEATURE:
<221> NAME/KEY: intron9
<222> LOCATION: (5241)..(5306)
<220> FEATURE:
<221> NAME/KEY: exon
```

```
<222> LOCATION: (5307)..(5372)
<223> OTHER INFORMATION: exon10
<220> FEATURE:
<221> NAME/KEY: intron10
<222> LOCATION: (5373)..(5482)
<220> FEATURE:
<221> NAME/KEY: exon
<222> LOCATION: (5483)..(6409)
<223> OTHER INFORMATION: exon11
<220> FEATURE:
<221> NAME/KEY: intron11
<222> LOCATION: (6410)..(7052)
<220> FEATURE:
<221> NAME/KEY: exon
<222> LOCATION: (7053)..(7178)
<223> OTHER INFORMATION: exon12
<220> FEATURE:
<221> NAME/KEY: intron12
<222> LOCATION: (7179)..(7610)
<220> FEATURE:
<221> NAME/KEY: exon
<222> LOCATION: (7611)..(7887)
<223> OTHER INFORMATION: exon13
<220> FEATURE:
<221> NAME/KEY: 3'UTR
<222> LOCATION: (7888)..(8247)

<400> SEQUENCE: 6
```

```
actatagggc acgcgtggtc gacggcccgg gctggtctcc tatatacgtg gcgtccattt      60
cttactccgc tgccaccgct ctctgttgtt tcattttct cccaaaaatc aatttaccag     120
tgactgtgtc cttgcatcgc gtctccactc tcccccattc ctattattca aaacccagaa    180
atttccagag ccccagccat ttttcttttc gtttgttttc tgcctgtaaa tagtgtatat    240
ctgaactcta ggagcgcggt ggtggtggtg gtggtggcga gcgtaactgg tgcgcggcgg    300 cagtggtg atg gcg gga aat gac tgg ata aac agt tac ttg gag gcg ata    350
         Met Ala Gly Asn Asp Trp Ile Asn Ser Tyr Leu Glu Ala Ile
         1               5                  10 tta gat gtg gga cca ggg att gat gat gcc aag tcg tca ctg ctg ctc    398
Leu Asp Val Gly Pro Gly Ile Asp Asp Ala Lys Ser Ser Leu Leu Leu
15              20                  25                  30 aga gaa aga ggg agg ttc agc cca act cgc tac ttc gtg gag gag gtc    446
Arg Glu Arg Gly Arg Phe Ser Pro Thr Arg Tyr Phe Val Glu Glu Val
                35                  40                  45 att acc ggc ttt gat gag acc gat ctc cac cgc tct tgg gcc cgc        491
Ile Thr Gly Phe Asp Glu Thr Asp Leu His Arg Ser Trp Ala Arg
            50                  55                  60 gtaagtgttc caccactact tctagtccgc taccctgttt ttctgaacta tatagaatga    551
cgaaaaagga agttggtgtt cgagtcgaga tttatgaatg gatgaatgat tttttaacgt    611 tggatag gcg caa gcg acc cgg agt ccg caa gag agg aat acc agg ctt    660
        Ala Gln Ala Thr Arg Ser Pro Gln Glu Arg Asn Thr Arg Leu
                65                  70                  75 gag aat ttg tgc tgg cgt att tgg aat ttg gct cgc cag aaa aag cag    708
Glu Asn Leu Cys Trp Arg Ile Trp Asn Leu Ala Arg Gln Lys Lys Gln
                80                  85                  90 gtcttctact ggcctatttg ttttttgttt tgttttttta attttagcg cgaaatctgt     768 ttaaaatata gttattatgg atatgcttga ttcaatttga tggaatttta gatttatgtg    828
catattggtg cgtttattc aacggtgata gctgaaataa acaaattcga gttgcatgga    888
tgatagggct caaaatttta agtgaccttg catgcttcat caagtactga gtgtgtcatg    948
tagaaaagaa caaacattgg tctgctattg ttatgagtat ttttattct ctttcttgtg   1008 gcgtcagttt ctatgacaac tcacaaaaag tacgaagtct gtacttctgt tactgcatgt   1068
attaaacatt ttttctttcc ctaaaacctt ttttcttgaa atgatttgc cataaagtca   1128
```

```
ttatatgttc cccatagagg ttgtcactgc ttttattaat cgattacact acgtcattac    1188 cctattttt gtttcttgta cttgaattca gagcaaaatc agtaaattat tgtgtagaag     1248
agtggagaac gaaaatgata ttagctttat atttgtgagt tctgcccaaa atttcgtgta    1308
ctggaataat gacatgtttt ttggttgagc aagctgagaa cttcagccat gaggccattc    1368
aagatgtcgt cagaatttat tgtcattatt gagcacttta ggatgcaaac atggtggtag    1428
actcattaaa gtgtgaaagt taattatttt tggaattcaa atgaataata gtaagttaaa    1488
ttctcgtgtt tttagaagaa actattctgg gaatccaaaa caggaagtta gtcattagtg    1548
cacgagggaa ttagtataac ttgcctttct tttccattat ggtctttaaa ggacgrttaa    1608
cacatgccat tttgttttc ttgtcaaaga aatgcataaa atatgtgatt tcttgattct     1668
catctgtgca tggtagcagt gtgagaagaa tggaattatt ggtctgtttt tgtag ctt     1726
                                                                Leu gag gga gag caa gct cag agg atg gcg aaa cgc cgt ctt gaa cgy gaa      1774
Glu Gly Glu Gln Ala Gln Arg Met Ala Lys Arg Arg Leu Glu Arg Glu
        95                  100                 105 agg ggc cgc aga gaa gca gtt gct gat atg tct gaa gac tta tca gag      1822
Arg Gly Arg Arg Glu Ala Val Ala Asp Met Ser Glu Asp Leu Ser Glu
    110                 115                 120 ggg gag aaa gga gat aca gtt ggt gac ttt ttg gca cat ggt gag agc      1870
Gly Glu Lys Gly Asp Thr Val Gly Asp Phe Leu Ala His Gly Glu Ser
125                 130                 135                 140 aat agg ggt cga ttg ccc aga ata agc tct gtt gaa aca acg gaa gca      1918
Asn Arg Gly Arg Leu Pro Arg Ile Ser Ser Val Glu Thr Thr Glu Ala
        145                 150                 155 tgg gct agt caa cag aag gaa aag aag tgg tat att gta ttg ata          1963
Trp Ala Ser Gln Gln Lys Glu Lys Lys Trp Tyr Ile Val Leu Ile
        160                 165                 170 aggtatagaa gttcacacat tacgggctca ttactttgta atgctgagag agggatgatc    2023
tcaaagggct cttctaacgt gatgttcata acgtcctctg cagtctttcc ctgtaaatca    2083
gtttaatgat aattgctggc aatgttttga gaatttggaa agatttgttc tgtttcatat    2143
gatgctgttt tgatatcttt gtctacgtga ttatcctcac tgttttcttt aacacataat    2203 attattgc agc ctt cat gga ctg att cgt ggc gaa aac atg gag ctt gga    2253
        Ser Leu His Gly Leu Ile Arg Gly Glu Asn Met Glu Leu Gly
            175                 180                 185 cgg gat tct gat ack ggt ggt cag gtatatttgg ttataagatc ctgtttatca    2307
Arg Asp Ser Asp Xaa Gly Gly Gln
                190 tgtactaagc ctagtcccat tcaytgaatg attgctagac agcatttct ggtagttttt    2367 gygctctcat agttgctcaa ggaatcttag gtaagrtact tcattaaaat tttgtttcgt    2427 ttttggtaac ctagctgctt atccaaaaga artgagtaag acactgggat ycatgcattt    2487 cag gtg aag tat gta gtc gaa ctt gca agg gct tta ggt tca atg cca     2535
Val Lys Tyr Val Val Glu Leu Ala Arg Ala Leu Gly Ser Met Pro
    195                 200                 205 ggt gta tat cgg gtt gat tta ctt acg agg cag gta tca tca ctg gaa     2583
Gly Val Tyr Arg Val Asp Leu Leu Thr Arg Gln Val Ser Ser Leu Glu
210                 215                 220 gta gat tgg agt tac ggt gaa ccc act gag atg ctg cct cct aga aat     2631
Val Asp Trp Ser Tyr Gly Glu Pro Thr Glu Met Leu Pro Pro Arg Asn
225                 230                 235                 240 tca gaa ggt tta aat gag atg ggg gag agc agt ggg gct tat att att     2679
Ser Glu Gly Leu Asn Glu Met Gly Glu Ser Ser Gly Ala Tyr Ile Ile
            245                 250                 255
```

```
cgc att cct ttt ggc cct aga gac aaa tac att cct aag gag ctt ctg        2727
Arg Ile Pro Phe Gly Pro Arg Asp Lys Tyr Ile Pro Lys Glu Leu Leu
            260                 265                 270 tgg cct tac ctt tct gaa ttt gtt gat ggt gca ctt agc cat ata atc        2775
Trp Pro Tyr Leu Ser Glu Phe Val Asp Gly Ala Leu Ser His Ile Ile
            275                 280                 285 cag atg tcc aaa gtt ctt ggt gag caa gtt ggt ggt gga cat cct gtc        2823
Gln Met Ser Lys Val Leu Gly Glu Gln Val Gly Gly Gly His Pro Val
            290                 295                 300 tgg cct gtt gct att cat gga cat tat gca gat gct ggt gat tct gca        2871
Trp Pro Val Ala Ile His Gly His Tyr Ala Asp Ala Gly Asp Ser Ala
305                 310                 315                 320 gct ctt ctg tct ggg gct cta aat gtt ccc atg ctt ttc act ggt cat        2919
Ala Leu Leu Ser Gly Ala Leu Asn Val Pro Met Leu Phe Thr Gly His
                325                 330                 335 tcc ctt ggt cga gat aag ttg gag caa ctt ttg aga cag ggt aga ctg        2967
Ser Leu Gly Arg Asp Lys Leu Glu Gln Leu Leu Arg Gln Gly Arg Leu
            340                 345                 350 tca agg gac gaa ata aat tct acg tac aaa ata atg cgc agg ata gag        3015
Ser Arg Asp Glu Ile Asn Ser Thr Tyr Lys Ile Met Arg Arg Ile Glu
            355                 360                 365 gca gag gag ata tca ctt gat gcc tct gaa act gtc ata aca agc aca        3063
Ala Glu Glu Ile Ser Leu Asp Ala Ser Glu Thr Val Ile Thr Ser Thr
370                 375                 380 aga cag gag att gag gag caa tgg cgt tta tat gat ggc ttt gat cca        3111
Arg Gln Glu Ile Glu Glu Gln Trp Arg Leu Tyr Asp Gly Phe Asp Pro
385                 390                 395                 400 atc ctg gga agg aaa ttg cgg gct agg atc agg cgc aat gtt agc tgt        3159
Ile Leu Gly Arg Lys Leu Arg Ala Arg Ile Arg Arg Asn Val Ser Cys
                405                 410                 415 tat ggc aga ttc atg cct cga atg gct gta agttttcatt tttgcttgga          3209
Tyr Gly Arg Phe Met Pro Arg Met Ala Val
            420                 425 actatactgg ctgatgaagt tacattttat ctgtttaatg tttgtaaacc acaaaatctt      3269
tgtttgttta ttcaattatt gtataatttt ttactacgat tgagatcaaa tgttgagttt      3329
ggtggaagac actgctggtt ttcttaaatt tgcttttcaa ctttgcctat acatgttaag      3389
ttggatactt tttctgctta agcgagttgt acttgactaa gctaaggttg aaaagatgct      3449
atgcacttcg agtctagtat attccttatt tttgtagaat aatgtatata gactcctgtt      3509
gctccttgtc aagtataaat attttgtagc agcgtctgcc ttcgttgact ccttttgctga     3569 ttccttttt tttcttgctg cttctgcaat tgcatttcct gaatttgctt gatttatgac       3629
cctggttgta actattagtc accatatatc attttaattc ttgagagatg aagcatgcaa      3689
caaattagaa ttgctcatgg acttataagt tatctcatgt attaagctct cataattctt      3749
tctgatattg gatcaaattt tgagagttg gttgatcaga ttggctcctt tctaagatca       3809
gctggaaagt gaagtatcaa gtcctttatg tgatatacat atttcttttg caggta att      3868
                                                                  Ile cct cct ggg atg gag ttc cat cac att gtc cca cat gat ggt gac atg        3916
Pro Pro Gly Met Glu Phe His His Ile Val Pro His Asp Gly Asp Met
            430                 435                 440 gat ggt gag atg gaa gga aat gag gat gga aag tct ccg gat cca cat        3964
Asp Gly Glu Met Glu Gly Asn Glu Asp Gly Lys Ser Pro Asp Pro His
445                 450                 455 att tgg gga gag gtcttaattt tcttgataat acctaatctg cagctgcatt            4016
Ile Trp Gly Glu
460 cctcttaatt ttgttcattt atttctttct ccttttgctg ttatgcaagt tctcttttg       4076
```

| | | |
|---|---|---|
| tggtgtcatg cag ata atg cgc tac ttc aca aat cca cga aag cct atg<br>                Ile Met Arg Tyr Phe Thr Asn Pro Arg Lys Pro Met<br>                465                470                475 | | 4125 |
| ata cta gcc ctt gcc agg cca gat ccc aaa arg aac cta acg aca ttg<br>Ile Leu Ala Leu Ala Arg Pro Asp Pro Lys Xaa Asn Leu Thr Thr Leu<br>                480                485                490 | | 4173 |
| gty aaa gcw ttt ggt gaa tgt cgt cca ctt caa gaa ctt gct aac ctt<br>Xaa Lys Ala Phe Gly Glu Cys Arg Pro Leu Gln Glu Leu Ala Asn Leu<br>            495                500                505 | | 4221 |
| gtgagttgga ttattagtgt gactcctttt tttttcctc ccctcaatat gggacaaaag | | 4281 |
| tagattgagc tgtttctctt tgtaatttgc ag aca ttg ata atg ggg aac cgt<br>                                            Thr Leu Ile Met Gly Asn Arg<br>                                                        510 | | 4334 |
| gat gat gtt gat gaa atg tca agc act agt gct tct gtt cta ctt tca<br>Asp Asp Val Asp Glu Met Ser Ser Thr Ser Ala Ser Val Leu Leu Ser<br>515                520                525                530 | | 4382 |
| ata cta aag ttg ata gac aag tat gat ctt tat ggt caa gtg gca tat<br>Ile Leu Lys Leu Ile Asp Lys Tyr Asp Leu Tyr Gly Gln Val Ala Tyr<br>                535                540                545 | | 4430 |
| cca aaa cat cac aag cag tcc gat gtt cct gac ata tac cgt ctt gca<br>Pro Lys His His Lys Gln Ser Asp Val Pro Asp Ile Tyr Arg Leu Ala<br>            550                555                560 | | 4478 |
| gca aag acg aag gtaatctgtt ttcttattct tctctcaatt taaatgttgc<br>Ala Lys Thr Lys<br>            565 | | 4530 |
| caaacttatc tctgtcctgc atggtgcatg aacatatgc tatttgtcac cgattctgac | | 4590 |
| tcagtgtgat tacagttcca cgtagttgag tttaatctgt cttttagtac atttggatgg | | 4650 |
| tgctgtgtga tgcgttcagg cattcttttt gtttgttgat cgcttataag atgaatagga | | 4710 |
| gagggtcatt gacagctgta tgctatgagt ggtttgagct ccctctttct tcttcacttg | | 4770 |
| atgggtacct ttcttttcct tgctgtcttt taccgttata gctaatgatg aatagtggtg | | 4830 |
| gttgtacatt gcctagtggt agatttatcc atctgttgag aagcaggttg gtatgcaatc | | 4890 |
| aagcaggttg gtaactgaat gattggacaa gaacaaatgt gaaaggcaac tataggcatg | | 4950 |
| ccatcaattg agaactcgtt gttatatagt gaaaagtagt aaacagcaca agtaatgtgt | | 5010 |
| tattgtagct tgcagattgt ctagatttca tgccaatttg tatgtcttct ataaacgttt | | 5070 |
| gctatcctta tgagtatgtc aatccaggag gccttgtaca tatttgcttg gagatatgca | | 5130 |
| ttcctggagg aaatgcatct ttagttatct aaccatattt agttatgttt tggcag ggt<br>                                                                                   Gly | | 5189 |
| gtt ttt att aat cca gct ttc atc gag cct ttt gga ctt act tta ata<br>Val Phe Ile Asn Pro Ala Phe Ile Glu Pro Phe Gly Leu Thr Leu Ile<br>            570                575                580 | | 5237 |
| gag gtaaccttct caggaaactg atctaagttt gtctatggcg ccaatgattt<br>Glu | | 5290 |
| atcttctatt caacag gca gca gct cac ggt tcg cca att gtt gca act aga<br>                      Ala Ala Ala His Gly Ser Pro Ile Val Ala Thr Arg<br>                          585                590                595 | | 5342 |
| aat ggt ggt cct gtc gac ata cac agg gta tgcaaatgtt tatgtttgca<br>Asn Gly Gly Pro Val Asp Ile His Arg Val<br>            600                605 | | 5392 |
| aatttaacta ccatgaagga tttacatgat attgtgaaa gttctctgga gacaagatct | | 5452 |
| gtcagagtaa tattctgtca ttgacaggtt ctt gac aac ggt ctt ctt gtt gat<br>                                              Leu Asp Asn Gly Leu Leu Val Asp<br>                                                            610 | | 5506 |
| cca cat aat cag cag tcc att gct gat gct ctt ttg aag ctg gtt gct | | 5554 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Pro | His | Asn | Gln | Gln | Ser | Ile | Ala | Asp | Ala | Leu | Leu | Lys | Leu | Val | Ala |      |
| 615 |     |     |     | 620 |     |     |     |     | 625 |     |     |     |     | 630 |     |      |
| gac | aag | caa | ctt | tgg | tca | aaa | tgc | agg | gca | aat | gga | tta | aaa | aac | att | 5602 |
| Asp | Lys | Gln | Leu | Trp | Ser | Lys | Cys | Arg | Ala | Asn | Gly | Leu | Lys | Asn | Ile |      |
|     |     |     |     | 635 |     |     |     |     | 640 |     |     |     |     | 645 |     |      |
| cac | ctt | ttc | tca | tgg | cct | gaa | cat | tgt | aaa | aca | tat | tta | act | aag | ata | 5650 |
| His | Leu | Phe | Ser | Trp | Pro | Glu | His | Cys | Lys | Thr | Tyr | Leu | Thr | Lys | Ile |      |
|     |     |     | 650 |     |     |     |     | 655 |     |     |     |     | 660 |     |     |      |
| gca | agt | tgc | aaa | cca | agg | caa | cca | aga | tgg | ttg | aga | aat | gat | gat | gac | 5698 |
| Ala | Ser | Cys | Lys | Pro | Arg | Gln | Pro | Arg | Trp | Leu | Arg | Asn | Asp | Asp | Asp |      |
|     |     | 665 |     |     |     |     | 670 |     |     |     |     | 675 |     |     |     |      |
| gat | gaa | aat | tca | gaa | tct | gat | tca | cct | aat | gat | tcc | tta | aga | gat | ata | 5746 |
| Asp | Glu | Asn | Ser | Glu | Ser | Asp | Ser | Pro | Asn | Asp | Ser | Leu | Arg | Asp | Ile |      |
|     | 680 |     |     |     |     | 685 |     |     |     |     | 690 |     |     |     |     |      |
| cag | gat | ata | tct | ttg | aat | ttg | aag | ttt | tca | ctt | gat | ggg | gat | aaa | aac | 5794 |
| Gln | Asp | Ile | Ser | Leu | Asn | Leu | Lys | Phe | Ser | Leu | Asp | Gly | Asp | Lys | Asn |      |
| 695 |     |     |     | 700 |     |     |     |     | 705 |     |     |     |     | 710 |     |      |
| gtg | ggt | aag | gaa | aat | ggt | gat | ggg | tct | ttg | gat | ctt | gat | gat | cga | aaa | 5842 |
| Val | Gly | Lys | Glu | Asn | Gly | Asp | Gly | Ser | Leu | Asp | Leu | Asp | Asp | Arg | Lys |      |
|     |     |     |     | 715 |     |     |     |     | 720 |     |     |     |     | 725 |     |      |
| agc | aag | tta | gaa | act | gca | gtt | ttg | agt | tgg | tcc | agg | ggc | gtg | cag | aag | 5890 |
| Ser | Lys | Leu | Glu | Thr | Ala | Val | Leu | Ser | Trp | Ser | Arg | Gly | Val | Gln | Lys |      |
|     |     |     | 730 |     |     |     |     | 735 |     |     |     |     | 740 |     |     |      |
| act | acc | cag | aaa | tct | ggt | tcc | aca | gac | aag | ggt | gac | caa | aac | tct | ggt | 5938 |
| Thr | Thr | Gln | Lys | Ser | Gly | Ser | Thr | Asp | Lys | Gly | Asp | Gln | Asn | Ser | Gly |      |
|     |     | 745 |     |     |     |     | 750 |     |     |     |     | 755 |     |     |     |      |
| gct | ggt | aag | ttc | cca | gca | ctc | agg | agg | agg | aaa | tac | atg | ttt | gta | att | 5986 |
| Ala | Gly | Lys | Phe | Pro | Ala | Leu | Arg | Arg | Arg | Lys | Tyr | Met | Phe | Val | Ile |      |
|     | 760 |     |     |     |     | 765 |     |     |     |     | 770 |     |     |     |     |      |
| gca | gtg | gat | tgt | ggt | gcc | ctt | tca | gaa | agt | gtc | aaa | agg | att | ttt | gat | 6034 |
| Ala | Val | Asp | Cys | Gly | Ala | Leu | Ser | Glu | Ser | Val | Lys | Arg | Ile | Phe | Asp |      |
| 775 |     |     |     | 780 |     |     |     |     | 785 |     |     |     |     | 790 |     |      |
| gct | ttg | gag | aag | gaa | aag | gca | gaa | ggc | tct | ata | gga | ttt | ata | tta | gcc | 6082 |
| Ala | Leu | Glu | Lys | Glu | Lys | Ala | Glu | Gly | Ser | Ile | Gly | Phe | Ile | Leu | Ala |      |
|     |     |     |     | 795 |     |     |     |     | 800 |     |     |     |     | 805 |     |      |
| aca | tct | ttt | aac | ttg | tca | gaa | cta | cat | tct | ttt | ctg | gtt | tca | gag | cgt | 6130 |
| Thr | Ser | Phe | Asn | Leu | Ser | Glu | Leu | His | Ser | Phe | Leu | Val | Ser | Glu | Arg |      |
|     |     |     | 810 |     |     |     |     | 815 |     |     |     |     | 820 |     |     |      |
| ctg | aat | cct | att | gat | ttt | gat | gct | ttt | att | tgc | aac | agt | ggt | ggt | gat | 6178 |
| Leu | Asn | Pro | Ile | Asp | Phe | Asp | Ala | Phe | Ile | Cys | Asn | Ser | Gly | Gly | Asp |      |
|     |     | 825 |     |     |     |     | 830 |     |     |     |     | 835 |     |     |     |      |
| ctt | tat | tat | tca | tca | ctt | cac | tct | gat | gag | aac | cct | ttc | ata | gtt | gac | 6226 |
| Leu | Tyr | Tyr | Ser | Ser | Leu | His | Ser | Asp | Glu | Asn | Pro | Phe | Ile | Val | Asp |      |
|     | 840 |     |     |     |     | 845 |     |     |     |     | 850 |     |     |     |     |      |
| ttg | tat | tac | cat | tca | cat | att | gaa | tac | cgc | tgg | ggt | ggt | gaa | ggg | ttg | 6274 |
| Leu | Tyr | Tyr | His | Ser | His | Ile | Glu | Tyr | Arg | Trp | Gly | Gly | Glu | Gly | Leu |      |
| 855 |     |     |     | 860 |     |     |     |     | 865 |     |     |     |     | 870 |     |      |
| agg | aag | aca | ttg | gtg | cgg | tgg | gcg | gcc | tca | att | act | gat | aag | aag | ggc | 6322 |
| Arg | Lys | Thr | Leu | Val | Arg | Trp | Ala | Ala | Ser | Ile | Thr | Asp | Lys | Lys | Gly |      |
|     |     |     |     | 875 |     |     |     |     | 880 |     |     |     |     | 885 |     |      |
| gat | gac | aaa | gaa | cac | att | gtg | gtt | gaa | gat | gaa | aag | aac | tca | gct | gac | 6370 |
| Asp | Asp | Lys | Glu | His | Ile | Val | Val | Glu | Asp | Glu | Lys | Asn | Ser | Ala | Asp |      |
|     |     |     | 890 |     |     |     |     | 895 |     |     |     |     | 900 |     |     |      |
| tac | tgc | tat | tcg | ttt | aaa | gtt | tgc | aag | cca | gga | gtg | gta |     |     |     | 6419 |
| Tyr | Cys | Tyr | Ser | Phe | Lys | Val | Cys | Lys | Pro | Gly | Val | Val | agtttccaaa |     |     |      |
|     |     | 905 |     |     |     |     | 910 |     |     |     |     | 915 |     |     |     |      | ttcctatctt cagcacctac tctctctctc tctctctctc tgagtggatt gtggaactta 6479 gttttgtgag ctctctgtgg ttgatgttgt tgaagtcatt gatgaacctc ataatcaaat 6539 tttgatgtag cattgttcaa gattattatt ttcttagttt cgaattctgg ctcaatgcaa 6599

```
ccacttttta ctagtagctt tcttttataa aattctctta acagtagcaa tttttcatac    6659
ttttgaatgt tcccttcatc aaggttctta cttcagtttt ctagctactt tattgcctac    6719
tgctgatttc atgcttctaa atttattaga tgtatggttt atgttcgta attcaaatcc     6779 tcctttctgg atagccacct taggtacttg tattcaatgt tcttagagat cttttgctta    6839
atcatagcac attctagaga acttggctct tttagtcct tttcatgctt atgcaagcgg     6899
tccgatatgt ttttttttct ttttagtcct ttgcatgaga tgtatatagc ctctaataac    6959
ttattgattt atttcagtga ctataaactc tgtgcatttt tctaggagag tatcaaacac    7019
attttttgaa aaataatttt gtctttacag gtt cct cca gtg agg gaa ctc agg     7073
                                  Pro Pro Val Arg Glu Leu Arg
                                                      920 aaa gta atg agg att cag gct ctt cgt tgt cat gtg att tat tgt caa      7121
Lys Val Met Arg Ile Gln Ala Leu Arg Cys His Val Ile Tyr Cys Gln
        925                 930                 935 aac ggg agt aag att aat gtc att cca gtg cta gca gct cgt tgc cag      7169
Asn Gly Ser Lys Ile Asn Val Ile Pro Val Leu Ala Ala Arg Cys Gln
940                 945                 950 gca ctc agg tttgtttctg atatactaat gaggatgacg ttttctttc                7218
Ala Leu Arg
955 agaactgtta gttctgtatt attttcctgt tgtttcctca agtcatcttg cttttagct      7278 ttgatacttg caatcaatgc actatcctcc taatactgaa agagaactct gagatcgtag     7338 ttcgtatagc ttttatcatt gacaactgag ctagtattac tggtcatgcc cataaatatt    7398 gattcttaga atataccaat ggaggaagta atcatgttga cagcctctac tgttctttcc    7458 tcttgctgct tgtgtgtcag gtcatatagt tggctatagc acatctgtac tggaaaatgt    7518 cttcttgaac atgagagaaa tcaagtacta ttttctctgt tatacttgaa agatttttg     7578 atcacatgtg attcttaaac atcttcttta gg tac ctg tat ctt cga tgg ggt      7631
                                     Tyr Leu Tyr Leu Arg Trp Gly
                                                         960 atg gat ttg tca aaa gtg gtg gtt ttt gtt gga gaa agt ggg gac act      7679
Met Asp Leu Ser Lys Val Val Val Phe Val Gly Glu Ser Gly Asp Thr
965                 970                 975                 980 gat tat gaa gga tta ctt ggt ggt gtg cac aag tct gtg ata ctg aaa      7727
Asp Tyr Glu Gly Leu Leu Gly Gly Val His Lys Ser Val Ile Leu Lys
                985                 990                 995 gga gtt tgc agt gga gaa agc agc caa ctt cat gcc aac aga agc          7772
Gly Val Cys Ser Gly Glu Ser Ser Gln Leu His Ala Asn Arg Ser
                1000            1005                1010 tac cca ctt acc gat gtg gtg gca ttt gac aat ccg aac ctt att          7817
Tyr Pro Leu Thr Asp Val Val Ala Phe Asp Asn Pro Asn Leu Ile
            1015                1020                1025 cag acg agt gaa gac tgc agc agt gct gag ctg cgc gag tcg ttg          7862
Gln Thr Ser Glu Asp Cys Ser Ser Ala Glu Leu Arg Glu Ser Leu
            1030                1035                1040 gaa aag cta ggg gtt ctc aaa agc t agaaatttgc acttccgcac               7907
Glu Lys Leu Gly Val Leu Lys Ser
            1045 atcacagaaa agtttgacat gaactatata tatcgtgtta ataattggcc tgtttctccg    7967 ttgctcgtag agttgccaag atcctcgaag caaaaagttt tgctaccttg ttatgatacc    8027 ctgataaaaa ccatcagtgt atgattctat tcgttaattt ggttcttgct ttgaaactgg    8087 cacggttggt gctttcgacc tgttgataaa tgggttaaac taaagtgcc aactaagtta     8147 tgccgtatag gtgttgtaaa ttcctttttg tatcgtagtt gagggagaca tcgttgtaat    8207
```

```
gctgaaagct ataggatcaa tgagttgttc ctttcacagt                    8247
```

<210> SEQ ID NO 7
<211> LENGTH: 732
<212> TYPE: DNA
<213> ORGANISM: Coffea canephora

<400> SEQUENCE: 7

```
gaggcaggta tcatcaccgg aagtagattg gagttacggt gaacccactg agatgctgcc     60
tcctagaaat tcggaaggtt taaatgagat gggggagagc agtggggctt atcttattcg    120
cattcctttt ggccctagag acaaatacat tcctaaggag cttctgtggc cttacctttc    180
tgaatttgtt gatggtgcac ttagccatat aatccagatg tccaaagttc ttggtgagca    240
agttggtggt ggacatcctg tctggcctgt tgctattcat ggacattatg cagatgctgg    300
tgattctgca gctcttctat ctggggcttt aaatgttccc atgcttttca ctggtcattc    360
ccttggtcga gataagttgg agcaactttt gagacagggt agactgtcaa gggatgaaat    420
aaattctaca tacaaaataa tgcgcaggat agaggcagag gagatatcac ttgatgcctc    480
tgaaactgtc ataacaagca caagacagga gattgaggag caatggcgtt tatatgatgg    540
ctttgatcca atcctgggaa ggaaattgcg ggctaggatc aggcgcaatg ttagctgtta    600
tggcagattc atgcctcgaa tggctgtcat tcctcctggg atggagttcc atcacattgt    660
cccacatgat ggtgacatgg atggtgaaac ggaaggaaat gaagatggaa agtctccgga    720
tccacatatt tg                                                        732
```

<210> SEQ ID NO 8
<211> LENGTH: 806
<212> TYPE: PRT
<213> ORGANISM: Coffea canephora

<400> SEQUENCE: 8

```
Met Ala Glu Arg Val Leu Thr Arg Val His Ser Leu Arg Glu Arg Leu
1               5                   10                  15

Asp Ala Thr Leu Ala Ala His Arg Asn Asp Val Leu Leu Phe Met Ser
            20                  25                  30

Arg Leu Glu Thr His Gly Lys Gly Ile Leu Lys Pro His Gln Leu Leu
        35                  40                  45

Ala Glu Phe Glu Glu Ile Asn Lys Asp Gly Lys Gln Lys Ile His Asp
    50                  55                  60

His Ala Phe Glu Glu Val Leu Lys Ser Thr Gln Glu Ala Ile Val Leu
65                  70                  75                  80

Pro Pro Trp Val Ala Leu Ala Ile Arg Leu Arg Pro Gly Val Trp Glu
                85                  90                  95

Tyr Val Arg Val Asn Val His Ala Leu Val Val Glu Glu Leu Thr Val
            100                 105                 110

Pro Glu Tyr Leu His Phe Lys Glu Glu Leu Val Asp Gly Ser Lys Asn
        115                 120                 125

Gly Asn Phe Val Leu Glu Leu Asp Phe Glu Pro Phe Thr Ala Ser Phe
    130                 135                 140

Pro Lys Pro Thr Leu Thr Lys Tyr Ile Gly Asp Gly Val Glu Phe Leu
145                 150                 155                 160

Asn Arg His Leu Ser Ala Lys Met Phe His Asp Lys Glu Ser Met Ala
                165                 170                 175

Pro Leu Leu Asp Phe Leu Arg Val His Gln Tyr Lys Gly Lys Thr Met
            180                 185                 190
```

```
Met Leu Asn Asp Arg Ile Lys Asp Leu Asn Thr Leu Gln Ala Val Leu
        195                 200                 205
Arg Lys Ala Glu Glu Tyr Leu Thr Thr Leu Ser Ala Asp Thr Pro Tyr
    210                 215                 220
Ser Glu Phe Glu His Lys Phe Gln Glu Ile Gly Leu Glu Arg Gly Trp
225                 230                 235                 240
Gly Asp Thr Ala Glu Arg Val Leu Glu Met Ile Cys Met Leu Leu Asp
                245                 250                 255
Leu Leu Glu Ala Pro Asp Ser Cys Thr Leu Glu Lys Phe Leu Gly Arg
            260                 265                 270
Ile Pro Met Val Phe Asn Val Ile Leu Ser Pro His Gly Tyr Phe
        275                 280                 285
Ala Gln Glu Asn Val Leu Gly Tyr Pro Asp Thr Gly Gly Gln Val Val
    290                 295                 300
Tyr Ile Leu Asp Gln Val Pro Ala Leu Glu Arg Glu Met Leu Lys Arg
305                 310                 315                 320
Ile Lys Glu Gln Gly Leu Asp Val Lys Pro Arg Ile Leu Ile Ile Thr
                325                 330                 335
Arg Leu Leu Pro Asp Ala Pro Gly Thr Thr Cys Gly Gln Arg Leu Glu
            340                 345                 350
Lys Val Tyr Gly Ser Glu Tyr Ser His Ile Leu Arg Val Pro Phe Arg
        355                 360                 365
Thr Glu Lys Gly Val Val Arg Lys Trp Ile Ser Arg Phe Glu Val Trp
    370                 375                 380
Pro Tyr Met Glu Thr Phe Thr Glu Asp Val Ala Lys Glu Val Thr Ala
385                 390                 395                 400
Glu Leu Gln Ala Lys Pro Asp Leu Val Ile Gly Asn Tyr Ser Glu Gly
                405                 410                 415
Asn Leu Val Ala Ser Leu Leu Ala His Lys Leu Gly Val Thr Gln Cys
            420                 425                 430
Thr Ile Ala His Ala Leu Glu Lys Thr Lys Tyr Pro Asp Ser Asp Ile
        435                 440                 445
Tyr Leu Ser Lys Phe Asp Glu Lys Tyr His Phe Ser Cys Gln Phe Thr
    450                 455                 460
Ala Asp Leu Ile Ala Met Asn His Thr Asp Phe Ile Ile Thr Ser Thr
465                 470                 475                 480
Phe Gln Glu Ile Ala Gly Ser Lys Asp Thr Val Gly Gln Tyr Glu Ser
                485                 490                 495
His Met Ala Phe Thr Met Pro Gly Leu Tyr Arg Val Val His Gly Ile
            500                 505                 510
Asp Val Phe Asp Pro Lys Phe Asn Ile Val Ser Pro Gly Ala Asp Thr
        515                 520                 525
Asn Leu Tyr Tyr Pro His Thr Glu Lys Glu Lys Arg Leu Thr Ser Phe
    530                 535                 540
His Pro Glu Ile Glu Glu Leu Leu Phe Ser Asp Val Glu Asn Glu Glu
545                 550                 555                 560
His Leu Cys Val Leu Lys Asp Lys Lys Pro Ile Leu Phe Thr Met
                565                 570                 575
Ala Arg Leu Asp Arg Val Lys Asn Leu Thr Gly Leu Val Glu Leu Tyr
            580                 585                 590
Ala Lys Asn Pro Lys Leu Arg Glu Leu Val Asn Leu Val Val Val Gly
        595                 600                 605
Gly Asp Arg Arg Lys Glu Ser Lys Asp Leu Glu Glu Gln Ala Glu Met
```

-continued

```
                610                 615                 620
Lys Lys Met Tyr Ser Leu Ile Glu Thr Tyr Asn Leu Asn Gly Gln Phe
625                 630                 635                 640

Arg Trp Ile Ser Ser Gln Met Asn Arg Val Arg Asn Gly Glu Leu Tyr
                645                 650                 655

Arg Tyr Ile Ala Asp Thr Lys Gly Ala Phe Val Gln Pro Ala Phe Tyr
                660                 665                 670

Glu Ala Phe Gly Leu Thr Val Val Glu Ala Met Thr Cys Gly Leu Pro
                675                 680                 685

Thr Phe Ala Thr Asn His Gly Gly Pro Ala Glu Ile Ile His Gly
                690                 695                 700

Lys Ser Gly Phe His Ile Asp Pro Tyr His Gly Glu Gln Val Ser Glu
705                 710                 715                 720

Leu Leu Ala Asn Phe Phe Glu Arg Cys Lys Lys Glu Pro Ser Tyr Trp
                725                 730                 735

Asp Thr Ile Pro Ala Gly Gly Leu Lys Arg Ile Gln Glu Lys Tyr Thr
                740                 745                 750

Trp Gln Ile Tyr Ser Asp Arg Leu Leu Thr Leu Ala Gly Val Tyr Gly
                755                 760                 765

Phe Trp Lys Cys Val Ser Lys Leu Asp Arg Gln Glu Ile Arg Arg Tyr
770                 775                 780

Leu Glu Met Phe Tyr Ala Leu Lys Tyr Arg Lys Leu Ala Glu Ala Val
785                 790                 795                 800

Pro Leu Ala Val Asp Gln
                805
```

<210> SEQ ID NO 9
<211> LENGTH: 1049
<212> TYPE: PRT
<213> ORGANISM: Coffea canephora
<220> FEATURE:
<221> NAME/KEY: MISC_FEATURE
<222> LOCATION: (486)..(486)
<223> OTHER INFORMATION: Unknown amino acid (X)

<400> SEQUENCE: 9

```
Met Ala Gly Asn Asp Trp Ile Asn Ser Tyr Leu Glu Ala Ile Leu Asp
1               5                   10                  15

Val Gly Pro Gly Ile Asp Asp Ala Lys Ser Ser Leu Leu Leu Arg Glu
                20                  25                  30

Arg Gly Arg Phe Ser Pro Thr Arg Tyr Phe Val Glu Glu Val Ile Thr
                35                  40                  45

Gly Phe Asp Glu Thr Asp Leu His Arg Ser Trp Ala Arg Ala Gln Ala
                50                  55                  60

Thr Arg Ser Pro Gln Glu Arg Asn Thr Arg Leu Glu Asn Leu Cys Trp
65                  70                  75                  80

Arg Ile Trp Asn Leu Ala Arg Gln Lys Lys Gln Leu Glu Gly Glu Gln
                85                  90                  95

Ala Gln Arg Met Ala Lys Arg Leu Glu Arg Glu Arg Gly Arg Arg
                100                 105                 110

Glu Ala Val Ala Asp Met Ser Glu Asp Leu Ser Glu Gly Lys Gly
                115                 120                 125

Asp Thr Val Gly Asp Phe Leu Ala His Gly Glu Ser Asn Arg Gly Arg
                130                 135                 140

Leu Pro Arg Ile Ser Ser Val Glu Thr Thr Glu Ala Trp Ala Ser Gln
145                 150                 155                 160
```

-continued

```
Gln Lys Glu Lys Lys Trp Tyr Ile Val Leu Ile Ser Leu His Gly Leu
                165                 170                 175
Ile Arg Gly Glu Asn Met Glu Leu Gly Arg Asp Ser Asp Thr Gly Gly
            180                 185                 190
Gln Val Lys Tyr Val Val Glu Leu Ala Arg Ala Leu Gly Ser Met Pro
        195                 200                 205
Gly Val Tyr Arg Val Asp Leu Leu Thr Arg Gln Val Ser Ser Leu Glu
    210                 215                 220
Val Asp Trp Ser Tyr Gly Glu Pro Thr Glu Met Leu Pro Pro Arg Asn
225                 230                 235                 240
Ser Glu Gly Leu Asn Glu Met Gly Glu Ser Ser Gly Ala Tyr Ile Ile
                245                 250                 255
Arg Ile Pro Phe Gly Pro Arg Asp Lys Tyr Ile Pro Lys Glu Leu Leu
            260                 265                 270
Trp Pro Tyr Leu Ser Glu Phe Val Asp Gly Ala Leu Ser His Ile Ile
        275                 280                 285
Gln Met Ser Lys Val Leu Gly Glu Gln Val Gly Gly His Pro Val
    290                 295                 300
Trp Pro Val Ala Ile His Gly His Tyr Ala Asp Ala Gly Asp Ser Ala
305                 310                 315                 320
Ala Leu Leu Ser Gly Ala Leu Asn Val Pro Met Leu Phe Thr Gly His
                325                 330                 335
Ser Leu Gly Arg Asp Lys Leu Glu Gln Leu Leu Arg Gln Gly Arg Leu
            340                 345                 350
Ser Arg Asp Glu Ile Asn Ser Thr Tyr Lys Ile Met Arg Arg Ile Glu
        355                 360                 365
Ala Glu Glu Ile Ser Leu Asp Ala Ser Glu Thr Val Ile Thr Ser Thr
    370                 375                 380
Arg Gln Glu Ile Glu Glu Gln Trp Arg Leu Tyr Asp Gly Phe Asp Pro
385                 390                 395                 400
Ile Leu Gly Arg Lys Leu Arg Ala Arg Ile Arg Arg Asn Val Ser Cys
                405                 410                 415
Tyr Gly Arg Phe Met Pro Arg Met Ala Val Ile Pro Pro Gly Met Glu
            420                 425                 430
Phe His His Ile Val Pro His Asp Gly Asp Met Asp Gly Glu Met Glu
        435                 440                 445
Gly Asn Glu Asp Gly Lys Ser Pro Asp Pro His Ile Trp Gly Glu Ile
    450                 455                 460
Met Arg Tyr Phe Thr Asn Pro Arg Lys Pro Met Ile Leu Ala Leu Ala
465                 470                 475                 480
Arg Pro Asp Pro Lys Xaa Asn Leu Thr Thr Leu Val Lys Ala Phe Gly
                485                 490                 495
Glu Cys Arg Pro Leu Gln Glu Leu Ala Asn Leu Thr Leu Ile Met Gly
            500                 505                 510
Asn Arg Asp Asp Val Asp Glu Met Ser Ser Thr Ser Ala Ser Val Leu
        515                 520                 525
Leu Ser Ile Leu Lys Leu Ile Asp Lys Tyr Asp Leu Tyr Gly Gln Val
    530                 535                 540
Ala Tyr Pro Lys His His Lys Gln Ser Asp Val Pro Asp Ile Tyr Arg
545                 550                 555                 560
Leu Ala Ala Lys Thr Lys Gly Val Phe Ile Asn Pro Ala Phe Ile Glu
                565                 570                 575
Pro Phe Gly Leu Thr Leu Ile Glu Ala Ala Ala His Gly Ser Pro Ile
            580                 585                 590
```

```
Val Ala Thr Arg Asn Gly Gly Pro Val Asp Ile His Arg Val Leu Asp
            595                 600                 605

Asn Gly Leu Leu Val Asp Pro His Asn Gln Gln Ser Ile Ala Asp Ala
    610                 615                 620

Leu Leu Lys Leu Val Ala Asp Lys Gln Leu Trp Ser Lys Cys Arg Ala
625                 630                 635                 640

Asn Gly Leu Lys Asn Ile His Leu Phe Ser Trp Pro Glu His Cys Lys
                645                 650                 655

Thr Tyr Leu Thr Lys Ile Ala Ser Cys Lys Pro Arg Gln Pro Arg Trp
            660                 665                 670

Leu Arg Asn Asp Asp Asp Glu Asn Ser Glu Ser Asp Ser Pro Asn
    675                 680                 685

Asp Ser Leu Arg Asp Ile Gln Asp Ile Ser Leu Asn Leu Lys Phe Ser
        690                 695                 700

Leu Asp Gly Asp Lys Asn Val Gly Lys Glu Asn Gly Asp Gly Ser Leu
705                 710                 715                 720

Asp Leu Asp Asp Arg Lys Ser Lys Leu Glu Thr Ala Val Leu Ser Trp
                725                 730                 735

Ser Arg Gly Val Gln Lys Thr Thr Gln Lys Ser Gly Ser Thr Asp Lys
            740                 745                 750

Gly Asp Gln Asn Ser Gly Ala Gly Lys Phe Pro Ala Leu Arg Arg Arg
        755                 760                 765

Lys Tyr Met Phe Val Ile Ala Val Asp Cys Gly Ala Leu Ser Glu Ser
770                 775                 780

Val Lys Arg Ile Phe Asp Ala Leu Glu Lys Glu Lys Ala Glu Gly Ser
785                 790                 795                 800

Ile Gly Phe Ile Leu Ala Thr Ser Phe Asn Leu Ser Glu Leu His Ser
                805                 810                 815

Phe Leu Val Ser Glu Arg Leu Asn Pro Ile Asp Phe Asp Ala Phe Ile
            820                 825                 830

Cys Asn Ser Gly Gly Asp Leu Tyr Tyr Ser Ser Leu His Ser Asp Glu
        835                 840                 845

Asn Pro Phe Ile Val Asp Leu Tyr Tyr His Ser His Ile Glu Tyr Arg
    850                 855                 860

Trp Gly Glu Gly Leu Arg Lys Thr Leu Val Arg Trp Ala Ala Ser
865                 870                 875                 880

Ile Thr Asp Lys Lys Gly Asp Asp Lys Glu His Ile Val Val Glu Asp
                885                 890                 895

Glu Lys Asn Ser Ala Asp Tyr Cys Tyr Ser Phe Lys Val Cys Lys Pro
            900                 905                 910

Gly Val Val Pro Pro Val Arg Glu Leu Arg Lys Val Met Arg Ile Gln
        915                 920                 925

Ala Leu Arg Cys His Val Ile Tyr Cys Gln Asn Gly Ser Lys Ile Asn
930                 935                 940

Val Ile Pro Val Leu Ala Ala Arg Cys Gln Ala Leu Arg Tyr Leu Tyr
945                 950                 955                 960

Leu Arg Trp Gly Met Asp Leu Ser Lys Val Val Phe Val Gly Glu
                965                 970                 975

Ser Gly Asp Thr Asp Tyr Glu Leu Leu Gly Val His Lys Ser
            980                 985                 990

Val Ile Leu Lys Gly Val Cys Ser  Gly Glu Ser Ser Gln  Leu His Ala
        995                 1000                 1005

Asn Arg  Ser Tyr Pro Leu Thr  Asp Val Val Ala Phe  Asp Asn Pro
```

```
               1010                1015                1020
Asn Leu Ile Gln Thr Ser Glu Asp Cys Ser Ser Ala Glu Leu Arg
        1025                1030                1035

Glu Ser Leu Glu Lys Leu Gly Val Leu Lys Ser
        1040                1045

<210> SEQ ID NO 10
<211> LENGTH: 425
<212> TYPE: PRT
<213> ORGANISM: Coffea canephora

<400> SEQUENCE: 10

Met Asp Arg Leu Ala Asp Ala His Leu Met Ile Val Ser Asp Leu
1               5                   10                  15

Asp His Thr Met Val Asp His His Asp Pro Glu Asn Met Ser Leu Leu
            20                  25                  30

Arg Phe Asn Ala Leu Trp Glu Ala Asn Tyr Arg Asp Asn Ser Leu Leu
        35                  40                  45

Val Phe Ser Thr Gly Arg Ser Pro Thr Leu Tyr Lys Glu Leu Arg Lys
    50                  55                  60

Glu Lys Pro Met Leu Thr Pro Asp Ile Thr Ile Met Ser Val Gly Thr
65                  70                  75                  80

Glu Ile Thr Tyr Gly Asn Ala Met Val Pro Asp Asp Gly Trp Val Glu
                85                  90                  95

Phe Leu Asn Gln Lys Trp Asp Arg Lys Ile Val Thr Glu Glu Thr Ser
            100                 105                 110

Lys Phe Pro Glu Leu Thr Leu Gln Ser His Thr Glu Gln Arg Pro His
        115                 120                 125

Lys Val Ser Phe Tyr Val Gln Lys Asp Lys Ala Gln Asp Val Ile Lys
    130                 135                 140

Ala Leu Ala Ala Arg Leu Glu Glu Arg Gly Leu Asp Val Lys Ile Ile
145                 150                 155                 160

Tyr Ser Gly Gly Met Asp Leu Asp Ile Leu Pro Gln Gly Ala Gly Lys
                165                 170                 175

Gly Gln Ala Leu Ala Tyr Leu Leu Lys Lys Phe Lys Ala Glu Gly Lys
            180                 185                 190

Ser Pro Asn Asn Thr Leu Val Cys Gly Asp Ser Gly Asn Asp Ala Glu
        195                 200                 205

Leu Phe Ser Ile Pro Glu Val Tyr Gly Val Met Val Ser Asn Ala Gln
    210                 215                 220

Glu Glu Leu Leu Gln Trp His Ala Ala Asn Ala Lys Asp Asn Ser Lys
225                 230                 235                 240

Ile Ile His Ala Thr Glu Arg Cys Ala Ala Gly Ile Ile Gln Ala Ile
                245                 250                 255

Gly His Phe Asn Leu Gly Pro Ser Val Ser Pro Arg Asp Val Thr Asp
            260                 265                 270

Leu Ser Asp Ser Lys Leu Glu Asp Phe Asp Pro Ala Tyr Glu Val Val
        275                 280                 285

Lys Phe Asn Leu Phe Phe Glu Arg Trp Arg Arg Ala Glu Val Glu Lys
    290                 295                 300

Ser Glu Leu Tyr Leu Ala Asn Met Lys Ala Val Cys Cys Pro Ser Gly
305                 310                 315                 320

Val Leu Val His Pro Ser Gly Ile Glu Lys Leu Leu Gly Asp Cys Val
                325                 330                 335

Asn Ala Phe Arg Thr Cys Tyr Gly Asp Gln Gln Gly Lys Ser Tyr Arg
```

```
                       340                 345                 350
Val Trp Val Asp Gln Val Leu Pro Thr Gln Val Gly Ser Asp Ser Trp
                355                 360                 365

Leu Val Lys Tyr Lys Lys Trp Glu Leu Ser Gly Glu Lys Gln Lys Gly
        370                 375                 380

Cys Leu Thr Thr Val Leu Leu Ser Ser Lys Gly Val Ser Val Pro Glu
385                 390                 395                 400

Gly Leu Thr Trp Val His Val His Gln Thr Trp Leu Asp Gly Ala Gly
                405                 410                 415

Pro Thr Asp Asp Ser Ser Trp Phe Phe
                420                 425

<210> SEQ ID NO 11
<211> LENGTH: 805
<212> TYPE: PRT
<213> ORGANISM: Solanum tuberosum

<400> SEQUENCE: 11

Met Ala Glu Arg Val Leu Thr Arg Val His Ser Leu Arg Glu Arg Leu
1               5                   10                  15

Asp Ala Thr Leu Ala Ala His Arg Asn Glu Ile Leu Leu Phe Leu Ser
            20                  25                  30

Arg Ile Glu Ser His Gly Lys Gly Ile Leu Lys Pro His Gln Leu Leu
        35                  40                  45

Ala Glu Phe Glu Ser Ile His Lys Glu Asp Lys Asp Lys Leu Asn Asp
    50                  55                  60

His Ala Phe Glu Glu Val Leu Lys Ser Thr Gln Glu Ala Ile Val Leu
65                  70                  75                  80

Pro Pro Trp Val Ala Leu Ala Ile Arg Leu Arg Pro Gly Val Trp Glu
                85                  90                  95

Tyr Val Arg Val Asn Val Asn Ala Leu Ile Val Glu Glu Leu Thr Val
            100                 105                 110

Pro Glu Phe Leu Gln Phe Lys Glu Glu Leu Val Asn Gly Thr Ser Asn
        115                 120                 125

Asp Asn Phe Val Leu Glu Leu Asp Phe Glu Pro Phe Thr Ala Ser Phe
    130                 135                 140

Pro Lys Pro Thr Leu Thr Lys Ser Ile Gly Asn Gly Val Glu Phe Leu
145                 150                 155                 160

Asn Arg His Leu Ser Ala Lys Met Phe His Asp Lys Glu Ser Met Thr
                165                 170                 175

Pro Leu Leu Glu Phe Leu Arg Val His His Tyr Lys Gly Lys Thr Met
            180                 185                 190

Met Leu Asn Asp Arg Ile Gln Asn Leu Tyr Thr Leu Gln Lys Val Leu
        195                 200                 205

Arg Lys Ala Glu Glu Tyr Leu Thr Thr Leu Ser Pro Glu Thr Ser Tyr
    210                 215                 220

Ser Ala Phe Glu His Lys Phe Gln Glu Ile Gly Leu Glu Arg Gly Trp
225                 230                 235                 240

Gly Asp Thr Ala Glu Arg Val Leu Glu Met Ile Cys Met Leu Leu Asp
                245                 250                 255

Leu Leu Glu Ala Pro Asp Ser Cys Thr Leu Glu Lys Phe Leu Ser Arg
            260                 265                 270

Ile Pro Met Val Phe Asn Val Val Ile Leu Ser Pro His Gly Tyr Phe
        275                 280                 285

Ala Gln Glu Asn Val Leu Gly Tyr Pro Asp Thr Gly Gly Gln Val Val
```

-continued

```
                290                 295                 300
Tyr Ile Leu Asp Gln Val Pro Ala Leu Glu Arg Glu Met Leu Lys Arg
305                 310                 315                 320

Ile Lys Glu Gln Gly Leu Asp Ile Lys Pro Arg Ile Leu Ile Val Thr
                325                 330                 335

Arg Leu Leu Pro Asp Ala Val Gly Thr Thr Cys Gly Gln Arg Leu Glu
                340                 345                 350

Lys Val Phe Gly Thr Glu His Ser His Ile Leu Arg Val Pro Phe Arg
                355                 360                 365

Thr Glu Lys Gly Ile Val Arg Lys Trp Ile Ser Arg Phe Glu Val Trp
370                 375                 380

Pro Tyr Met Glu Thr Phe Ile Glu Asp Val Gly Lys Glu Ile Thr Ala
385                 390                 395                 400

Glu Leu Gln Ala Lys Pro Asp Leu Ile Ile Gly Asn Tyr Ser Glu Gly
                405                 410                 415

Asn Leu Ala Ala Ser Leu Leu Ala His Lys Leu Gly Val Thr Gln Cys
                420                 425                 430

Thr Ile Ala His Ala Leu Glu Lys Thr Lys Tyr Pro Asp Ser Asp Ile
                435                 440                 445

Tyr Leu Asn Lys Phe Asp Glu Lys Tyr His Phe Ser Ala Gln Phe Thr
450                 455                 460

Ala Asp Leu Ile Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
                485                 490                 495

His Met Ala Phe Thr Met Pro Gly Leu Tyr Arg Val Val His Gly Ile
                500                 505                 510

Asp Val Phe Asp Pro Lys Phe Asn Ile Val Ser Pro Gly Ala Asp Val
                515                 520                 525

Asn Leu Tyr Phe Pro Tyr Ser Glu Lys Glu Lys Arg Leu Thr Thr Phe
                530                 535                 540

His Pro Glu Ile Glu Asp Leu Leu Phe Ser Asp Val Glu Asn Glu Glu
545                 550                 555                 560

His Leu Cys Val Leu Lys Asp Arg Asn Lys Pro Ile Ile Phe Thr Met
                565                 570                 575

Ala Arg Leu Asp Arg Val Lys Asn Leu Thr Gly Leu Val Glu Trp Tyr
                580                 585                 590

Ala Lys Asn Pro Arg Leu Arg Glu Leu Val Asn Leu Val Val Val Gly
                595                 600                 605

Gly Asp Arg Arg Lys Glu Ser Lys Asp Leu Glu Glu Gln Ala Glu Met
610                 615                 620

Lys Lys Met Tyr Glu Leu Ile Lys Thr His Asn Leu Asn Gly Gln Phe
625                 630                 635                 640

Arg Trp Ile Ser Ser Gln Met Asn Arg Val Arg Asn Gly Glu Leu Tyr
                645                 650                 655

Arg Tyr Ile Ala Asp Thr Arg Gly Ala Phe Val Gln Pro Ala Phe Tyr
                660                 665                 670

Glu Ala Phe Gly Leu Thr Val Val Glu Ala Met Ser Cys Gly Leu Pro
                675                 680                 685

Thr Phe Ala Thr Asn Gln Gly Gly Pro Ala Glu Ile Ile Val His Gly
                690                 695                 700

Lys Ser Gly Phe Gln Ile Asp Pro Tyr His Gly Glu Gln Ala Ala Asp
705                 710                 715                 720
```

-continued

```
Leu Leu Ala Asp Phe Phe Glu Lys Cys Lys Val Asp Pro Ser His Trp
                725                 730                 735

Glu Ala Ile Ser Glu Gly Gly Leu Lys Arg Ile Gln Glu Lys Tyr Thr
            740                 745                 750

Trp Gln Ile Tyr Ser Asp Arg Leu Leu Thr Leu Ala Ala Val Tyr Gly
        755                 760                 765

Phe Trp Lys His Val Ser Lys Leu Asp Arg Leu Glu Ile Arg Arg Tyr
    770                 775                 780

Leu Glu Met Phe Tyr Ala Leu Lys Phe Arg Lys Leu Ala Gln Leu Val
785                 790                 795                 800

Pro Leu Ala Val Glu
                805

<210> SEQ ID NO 12
<211> LENGTH: 805
<212> TYPE: PRT
<213> ORGANISM: Solanum tuberosum

<400> SEQUENCE: 12

Met Ala Glu Arg Val Leu Thr Arg Val His Ser Leu Arg Glu Arg Val
1               5                   10                  15

Asp Ala Thr Leu Ala Ala His Arg Asn Glu Ile Leu Leu Phe Leu Ser
            20                  25                  30

Arg Ile Glu Ser His Gly Lys Gly Ile Leu Lys Pro His Glu Leu Leu
        35                  40                  45

Ala Glu Phe Asp Ala Ile Arg Gln Asp Lys Asn Lys Leu Asn Glu
    50                  55                  60

His Ala Phe Glu Glu Leu Leu Lys Ser Thr Gln Glu Ala Ile Val Leu
65                  70                  75                  80

Pro Pro Trp Val Ala Leu Ala Ile Arg Leu Arg Pro Gly Val Trp Glu
                85                  90                  95

Tyr Ile Arg Val Asn Val Asn Ala Leu Val Val Glu Glu Leu Ser Val
            100                 105                 110

Pro Glu Tyr Leu Gln Phe Lys Glu Glu Leu Val Asp Gly Ala Ser Asn
        115                 120                 125

Gly Asn Phe Val Leu Glu Leu Asp Phe Glu Pro Phe Thr Ala Ser Phe
    130                 135                 140

Pro Lys Pro Thr Leu Thr Lys Ser Ile Gly Asn Gly Val Glu Phe Leu
145                 150                 155                 160

Asn Arg His Leu Ser Ala Lys Met Phe His Asp Lys Glu Ser Met Thr
                165                 170                 175

Pro Leu Leu Glu Phe Leu Arg Ala His His Tyr Lys Gly Lys Thr Met
            180                 185                 190

Met Leu Asn Asp Arg Ile Gln Asn Ser Asn Thr Leu Gln Asn Val Leu
        195                 200                 205

Arg Lys Ala Glu Glu Tyr Leu Ile Met Leu Ser Pro Asp Thr Pro Tyr
    210                 215                 220

Phe Glu Phe Glu His Lys Phe Gln Glu Ile Gly Leu Glu Lys Gly Trp
225                 230                 235                 240

Gly Asp Thr Ala Glu Arg Val Leu Glu Met Val Cys Met Leu Leu Asp
                245                 250                 255

Leu Leu Glu Ala Pro Asp Ser Cys Thr Leu Glu Lys Phe Leu Gly Arg
            260                 265                 270

Ile Pro Met Val Phe Asn Val Val Ile Leu Ser Pro His Gly Tyr Phe
        275                 280                 285
```

```
Ala Gln Glu Asn Val Leu Gly Tyr Pro Asp Thr Gly Gly Gln Val Val
            290                 295                 300

Tyr Ile Leu Asp Gln Val Pro Ala Leu Glu Arg Glu Met Leu Lys Arg
305                 310                 315                 320

Ile Lys Glu Gln Gly Leu Asp Ile Ile Pro Arg Ile Leu Ile Val Thr
                325                 330                 335

Arg Leu Leu Pro Asp Ala Val Gly Thr Thr Cys Gly Gln Arg Ile Glu
            340                 345                 350

Lys Val Tyr Gly Ala Glu His Ser His Ile Leu Arg Val Pro Phe Arg
                355                 360                 365

Thr Glu Lys Gly Ile Val Arg Lys Trp Ile Ser Arg Phe Glu Val Trp
370                 375                 380

Pro Tyr Met Glu Thr Phe Ile Glu Asp Val Ala Lys Glu Ile Ser Ala
385                 390                 395                 400

Glu Leu Gln Ala Lys Pro Asp Leu Ile Ile Gly Asn Tyr Ser Glu Gly
                405                 410                 415

Asn Leu Ala Ala Ser Leu Leu Ala His Lys Leu Gly Val Thr Gln Cys
                420                 425                 430

Thr Ile Ala His Ala Leu Glu Lys Thr Lys Tyr Pro Asp Ser Asp Ile
            435                 440                 445

Tyr Trp Lys Lys Phe Asp Glu Lys Tyr His Phe Ser Ser Gln Phe Thr
450                 455                 460

Ala Asp Leu Ile Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
                485                 490                 495

His Met Ala Phe Thr Met Pro Gly Leu Tyr Arg Val Val His Gly Ile
                500                 505                 510

Asn Val Phe Asp Pro Lys Phe Asn Ile Val Ser Pro Gly Ala Asp Ile
            515                 520                 525

Asn Leu Tyr Phe Ser Tyr Ser Glu Thr Glu Lys Arg Leu Thr Ala Phe
            530                 535                 540

His Pro Glu Ile Asp Glu Leu Leu Tyr Ser Asp Val Glu Asn Asp Glu
545                 550                 555                 560

His Leu Cys Val Leu Lys Asp Arg Thr Lys Pro Ile Leu Phe Thr Met
                565                 570                 575

Ala Arg Leu Asp Arg Val Lys Asn Leu Thr Gly Leu Val Glu Trp Tyr
            580                 585                 590

Ala Lys Asn Pro Arg Leu Arg Gly Leu Val Asn Leu Val Val Val Gly
                595                 600                 605

Gly Asp Arg Arg Lys Glu Ser Lys Asp Leu Glu Glu Gln Ala Glu Met
            610                 615                 620

Lys Lys Met Tyr Glu Leu Ile Glu Thr His Asn Leu Asn Gly Gln Phe
625                 630                 635                 640

Arg Trp Ile Ser Ser Gln Met Asn Arg Val Arg Asn Gly Glu Leu Tyr
                645                 650                 655

Arg Tyr Ile Ala Asp Thr Lys Gly Ala Phe Val Gln Pro Ala Phe Tyr
                660                 665                 670

Glu Ala Phe Gly Leu Thr Val Val Glu Ala Met Thr Cys Gly Leu Pro
                675                 680                 685

Thr Phe Ala Thr Asn His Gly Gly Pro Ala Glu Ile Ile Val His Gly
            690                 695                 700

Lys Ser Gly Phe His Ile Asp Pro Tyr His Gly Glu Gln Ala Ala Asp
705                 710                 715                 720
```

```
Leu Leu Ala Asp Phe Phe Glu Lys Cys Lys Glu Pro Ser His Trp
                725                 730                 735

Glu Thr Ile Ser Thr Gly Gly Leu Lys Arg Ile Gln Glu Lys Tyr Thr
            740                 745                 750

Trp Gln Ile Tyr Ser Glu Arg Leu Leu Thr Leu Ala Ala Val Tyr Gly
                755                 760                 765

Phe Trp Lys His Val Ser Lys Leu Asp Arg Leu Glu Ile Arg Arg Tyr
770                 775                 780

Leu Glu Met Phe Tyr Ala Leu Lys Tyr Arg Lys Met Ala Glu Ala Val
785                 790                 795                 800

Pro Leu Ala Ala Glu
                805

<210> SEQ ID NO 13
<211> LENGTH: 805
<212> TYPE: PRT
<213> ORGANISM: Lycopersicon esculentum

<400> SEQUENCE: 13

Met Ala Glu Arg Val Leu Thr Arg Val His Arg Leu Arg Glu Arg Val
1               5                   10                  15

Asp Ala Thr Leu Ala Ala His Arg Asn Glu Ile Leu Leu Phe Leu Ser
            20                  25                  30

Arg Ile Glu Ser His Gly Lys Gly Ile Leu Lys Pro His Glu Leu Leu
        35                  40                  45

Ala Glu Phe Asp Ala Ile Arg Gln Asp Lys Asp Lys Leu Asn Glu
    50                  55                  60

His Ala Phe Glu Glu Leu Leu Lys Ser Thr Gln Glu Ala Ile Val Leu
65                  70                  75                  80

Pro Pro Trp Val Ala Leu Ala Ile Arg Leu Arg Pro Gly Val Trp Glu
                85                  90                  95

Tyr Val Arg Val Asn Val Asn Ala Leu Val Val Glu Glu Leu Ser Val
            100                 105                 110

Pro Glu Tyr Leu Gln Phe Lys Glu Glu Leu Val Asp Gly Ala Ser Asn
        115                 120                 125

Gly Asn Phe Val Leu Glu Leu Asp Phe Glu Pro Phe Thr Ala Ser Phe
    130                 135                 140

Pro Lys Pro Thr Leu Thr Lys Ser Ile Gly Asn Gly Val Glu Phe Leu
145                 150                 155                 160

Asn Arg His Leu Ser Ala Lys Met Phe His Asp Lys Glu Ser Met Ala
                165                 170                 175

Pro Leu Leu Glu Phe Leu Arg Ala His His Tyr Lys Gly Lys Thr Met
            180                 185                 190

Met Leu Asn Asp Arg Ile His Asn Ser Asn Thr Leu Gln Asn Val Leu
        195                 200                 205

Arg Lys Ala Glu Glu Tyr Leu Ile Met Leu Pro Pro Glu Thr Pro Phe
    210                 215                 220

Phe Glu Phe Glu His Lys Phe Gln Glu Ile Gly Leu Gly Lys Gly Trp
225                 230                 235                 240

Gly Asp Thr Ala Glu Arg Val Leu Glu Met Val Cys Met Leu Leu Asp
                245                 250                 255

Leu Leu Glu Ala Pro Asp Ser Cys Thr Leu Glu Lys Phe Leu Gly Arg
            260                 265                 270

Ile Pro Met Val Phe Asn Val Val Ile Leu Ser Pro His Gly Tyr Leu
        275                 280                 285
```

```
Ala Gln Glu Asn Val Leu Gly Tyr Pro Asp Thr Gly Gly Gln Val Val
    290                 295                 300

Tyr Ile Leu Asp Gln Val Pro Ala Leu Glu Arg Glu Met Leu Lys Arg
305                 310                 315                 320

Ile Lys Glu Gln Gly Leu Asp Ile Ile Pro Arg Ile Leu Ile Val Thr
                325                 330                 335

Arg Leu Leu Pro Asp Ala Val Gly Thr Thr Cys Gly Gln Arg Leu Glu
            340                 345                 350

Lys Val Tyr Gly Thr Glu His Ser His Ile Leu Arg Val Pro Phe Arg
        355                 360                 365

Thr Glu Lys Gly Ile Val Arg Lys Trp Ile Ser Arg Phe Glu Val Trp
    370                 375                 380

Pro Tyr Met Glu Thr Phe Ile Glu Asp Val Ala Lys Glu Ile Ser Ala
385                 390                 395                 400

Glu Leu Gln Ala Lys Pro Asp Leu Ile Ile Gly Asn Tyr Ser Glu Gly
                405                 410                 415

Asn Leu Ala Ala Ser Leu Leu Ala His Lys Leu Gly Val Thr Gln Cys
            420                 425                 430

Thr Ile Ala His Ala Leu Glu Lys Thr Lys Tyr Pro Asp Ser Asp Ile
        435                 440                 445

Tyr Trp Lys Lys Phe Asp Glu Lys Tyr His Phe Ser Ser Gln Phe Thr
    450                 455                 460

Ala Asp Leu Ile Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
                485                 490                 495

His Met Ala Phe Thr Met Pro Gly Leu Tyr Arg Val Val His Gly Ile
            500                 505                 510

Asn Val Phe Asp Pro Lys Phe Asn Ile Val Ser Pro Gly Ala Asp Ile
        515                 520                 525

Asn Leu Tyr Phe Pro Tyr Ser Glu Ser Glu Lys Arg Leu Thr Ala Phe
    530                 535                 540

His Pro Glu Ile Asp Glu Leu Leu Tyr Ser Asp Val Glu Asn Asp Asp
545                 550                 555                 560

His Leu Cys Val Leu Lys Asp Arg Thr Lys Pro Ile Leu Phe Thr Met
                565                 570                 575

Ala Arg Leu Asp Arg Val Lys Asn Leu Thr Gly Leu Val Glu Trp Tyr
            580                 585                 590

Ala Lys Asn Pro Arg Leu Arg Gly Leu Val Asn Leu Val Val Val Gly
        595                 600                 605

Gly Asp Arg Arg Lys Glu Ser Lys Asp Leu Glu Glu Gln Ala Glu Met
    610                 615                 620

Lys Lys Met Tyr Glu Leu Ile Glu Thr His Asn Leu Asn Gly Gln Phe
625                 630                 635                 640

Arg Trp Ile Ser Ser Gln Met Asn Arg Val Arg Asn Gly Glu Leu Tyr
                645                 650                 655

Arg Tyr Ile Ala Asp Thr Lys Gly Ala Phe Val Gln Pro Ala Phe Tyr
            660                 665                 670

Glu Ala Phe Gly Leu Thr Val Val Glu Ala Met Thr Cys Gly Leu Pro
        675                 680                 685

Thr Phe Ala Thr Asn His Gly Gly Pro Ala Glu Ile Ile Val His Gly
    690                 695                 700

Lys Ser Gly Phe His Ile Asp Pro Tyr His Gly Glu Gln Ala Ala Asp
```

```
                     705                 710                 715                 720
Leu Leu Ala Asp Phe Phe Glu Lys Cys Lys Lys Glu Pro Ser His Trp
                    725                 730                 735

Glu Thr Ile Ser Thr Gly Gly Leu Lys Arg Ile Gln Glu Lys Tyr Thr
                740                 745                 750

Trp Gln Ile Tyr Ser Glu Arg Leu Leu Thr Leu Ala Ala Val Tyr Gly
            755                 760                 765

Phe Trp Lys His Val Ser Lys Leu Asp Arg Leu Glu Ile Arg Arg Tyr
        770                 775                 780

Leu Glu Met Phe Tyr Ala Leu Lys Tyr Arg Lys Met Ala Glu Ala Val
785                 790                 795                 800

Pro Leu Ala Ala Glu
                805

<210> SEQ ID NO 14
<211> LENGTH: 1050
<212> TYPE: PRT
<213> ORGANISM: Lycopersicon esculentum

<400> SEQUENCE: 14

Met Ala Gly Asn Asp Trp Ile Asn Ser Tyr Leu Glu Ala Ile Leu Asp
1               5                   10                  15

Val Gly Pro Gly Leu Asp Asp Lys Lys Ser Ser Leu Leu Leu Arg Glu
            20                  25                  30

Arg Gly Arg Phe Ser Pro Thr Arg Tyr Phe Val Glu Glu Val Ile Thr
        35                  40                  45

Gly Phe Asp Glu Thr Asp Leu Arg Arg Ser Trp Ile Arg Ala Gln Ala
    50                  55                  60

Thr Arg Ser Pro Gln Arg Arg Asn Thr Arg Leu Glu Asn Met Cys Trp
65                  70                  75                  80

Arg Ile Trp Asn Leu Ala Arg Gln Lys Lys Gln Leu Glu Gly Glu Gln
                85                  90                  95

Ala Arg Trp Met Ala Lys Arg Gln Glu Arg Glu Arg Gly Arg Arg
            100                 105                 110

Glu Ala Val Ala Asp Met Ser Glu Asp Leu Ser Glu Gly Glu Lys Gly
        115                 120                 125

Asp Ile Val Thr Asp Met Ser Ser His Gly Glu Ser Thr Arg Gly Arg
    130                 135                 140

Leu Pro Arg Ile Ser Cys Val Glu Thr Met Glu Ala Trp Val Ser Gln
145                 150                 155                 160

Gln Arg Gly Lys Lys Leu Tyr Ile Val Leu Ile Ser Leu His Gly Leu
                165                 170                 175

Ile Arg Gly Glu Asn Met Glu Leu Gly Arg Asp Ser Asp Thr Gly Gly
            180                 185                 190

Gln Val Lys Tyr Val Val Glu Leu Ala Arg Leu Gly Ser Met Pro Gly
        195                 200                 205

Val Tyr Arg Val Asp Leu Leu Thr Arg Gln Val Ser Ser Pro Glu Val
    210                 215                 220

Asp Trp Ser Tyr Gly Glu Pro Thr Glu Ile Val Thr Pro Ile Ser Thr
225                 230                 235                 240

Asp Gly Leu Met Ser Glu Met Gly Glu Ser Ser Gly Ala Tyr Ile Ile
                245                 250                 255

Arg Ile Pro Phe Gly Pro Arg Glu Lys Tyr Ile Pro Lys Glu Gln Leu
            260                 265                 270

Trp Pro Tyr Ile Pro Glu Phe Val Asp Gly Ala Leu Thr His Ile Ile
```

```
                       275                 280                 285
        Gln Met Ser Lys Val Leu Gly Glu Glu Ile Gly Asn Gly His Pro Val
            290                 295                 300

Trp Pro Val Ala Ile His Gly His Tyr Ala Asp Ala Gly Asp Ser Thr
        305                 310                 315                 320

Arg Leu Leu Ser Gly Ala Ser Asn Val Pro Met Leu Phe Thr Gly His
                        325                 330                 335

Ser Leu Arg Arg Asp Lys Leu Glu Gln Leu Leu Arg Gln Gly Arg Phe
                    340                 345                 350

Val Lys Asp Glu Val Asn Ser Thr Tyr Arg Tyr Thr Arg Ile Glu Ala
                355                 360                 365

Glu Asn Thr Leu Asp Arg Ser Glu Ile Val Ile Thr Ser Thr Arg His
            370                 375                 380

Glu Ile Asp Glu Gln Trp Arg Leu Tyr Asp Gly Phe Asp Pro Ile Leu
        385                 390                 395                 400

Glu Arg Lys Leu Arg Ala Arg Ile Lys Arg Asn Val Ser Cys Tyr Gly
                        405                 410                 415

Arg Phe Met Pro Arg Met Ala Val Ile Pro Pro Gly Met Glu Phe His
                    420                 425                 430

His Ile Val Pro His Glu Gly Asp Met Asp Gly Asp Thr Glu Gly Ser
                435                 440                 445

Glu Asp Gly Lys Ile Pro Asp Pro Pro Ile Trp Ala Glu Ile Met Arg
            450                 455                 460

Phe Phe Ser Asn Pro Arg Lys Pro Met Ile Leu Ala Leu Ala Arg Pro
        465                 470                 475                 480

Asp Pro Lys Lys Asn Leu Thr Thr Leu Val Lys Ala Phe Gly Glu Cys
                        485                 490                 495

Arg Pro Leu Arg Glu Leu Ala Asn Leu Thr Leu Ile Met Gly Asn Arg
                    500                 505                 510

Asp Asn Ile Asp Glu Met Ser Ser Thr Asn Ser Ala Leu Leu Leu Ser
                515                 520                 525

Ile Leu Lys Met Ile Asp Lys Tyr Asp Leu Tyr Gly Gln Val Ala Tyr
            530                 535                 540

Pro Lys His His Lys Gln Ser Asp Val Pro Asp Ile Tyr Arg Leu Ala
        545                 550                 555                 560

Gly Lys Thr Lys Gly Val Phe Ile Asn Pro Ala Phe Ile Glu Pro Phe
                        565                 570                 575

Gly Leu Thr Leu Ile Glu Ala Ala Ala Tyr Gly Leu Pro Met Val Ala
                    580                 585                 590

Thr Lys Asn Gly Gly Pro Val Asp Ile His Arg Val Leu Asp Asn Gly
                595                 600                 605

Leu Leu Val Asp Pro His Asp Gln Gln Ala Ile Ala Asp Ala Leu Leu
            610                 615                 620

Lys Leu Val Ala Asp Lys Gln Leu Trp Thr Lys Cys Arg Ala Asn Gly
        625                 630                 635                 640

Leu Lys Asn Ile His Leu Phe Ser Trp Pro Glu His Cys Lys Thr Tyr
                        645                 650                 655

Leu Ser Arg Ile Ala Ser Cys Lys Pro Arg Gln Pro Arg Trp Leu Arg
                    660                 665                 670

Pro Asp Asp Asp Asp Glu Asn Ser Glu Thr Asp Ser Pro Ser Asp
                675                 680                 685

Ser Leu Arg Asp Ile His Asp Ile Ser Leu Asn Leu Arg Phe Ser Leu
            690                 695                 700
```

```
Asp Gly Glu Lys Asn Asp Asn Lys Glu Asn Ala Asp Ser Thr Leu Asp
705                 710                 715                 720

Pro Glu Val Arg Lys Ser Lys Leu Glu Asn Ala Val Leu Ser Leu Ser
            725                 730                 735

Lys Gly Ala Pro Lys Ser Thr Ser Lys Ser Trp Ser Ser Asp Lys Ala
        740                 745                 750

Asp Gln Arg Ser Gly Ala Gly Lys Phe Pro Ala Ile Arg Arg His
    755                 760                 765

Ile Phe Val Ile Ala Val Asp Cys Asp Ala Ser Ser Gly Leu Ser Gly
770                 775                 780

Ser Val Lys Lys Ile Phe Glu Ala Val Glu Lys Glu Arg Ser Glu Gly
785                 790                 795                 800

Ser Ile Gly Phe Ile Leu Ala Ser Ser Phe Asn Ile Ser Glu Val Gln
                805                 810                 815

Ser Phe Leu Val Ser Glu Gly Met Ser Pro Thr Asp Phe Asp Ala Tyr
            820                 825                 830

Ile Cys Asn Ser Gly Gly Asp Leu Tyr Tyr Ser Ser Phe His Ser Glu
        835                 840                 845

Gln Asn Pro Phe Val Val Asp Leu Tyr Tyr His Ser His Ile Glu Tyr
    850                 855                 860

Arg Trp Gly Gly Glu Gly Leu Arg Lys Thr Leu Val Arg Trp Ala Ala
865                 870                 875                 880

Ser Ile Thr Asp Lys Asn Gly Glu Asn Gly Glu His Ile Val Val Glu
                885                 890                 895

Asp Glu Asp Asn Ser Ala Asp Tyr Cys Tyr Thr Phe Lys Val Cys Lys
            900                 905                 910

Pro Gly Lys Val Pro Pro Ala Lys Glu Leu Arg Lys Val Met Arg Ile
        915                 920                 925

Gln Ala Leu Arg Cys His Ala Val Tyr Cys Gln Asn Gly Gly Arg Ile
    930                 935                 940

Asn Met Ile Pro Val Leu Ala Ser Arg Ser Gln Ala Leu Arg Tyr Leu
945                 950                 955                 960

Tyr Leu Arg Trp Gly Met Asp Leu Ser Lys Leu Val Phe Val Gly
                965                 970                 975

Glu Ser Gly Asp Thr Asp Tyr Glu Gly Leu Ile Gly Gly Leu Arg Lys
            980                 985                 990

Ala Val Ile Met Lys Gly Leu Cys Thr Asn Ala Ser Ser Leu Ile His
        995                 1000                1005

Gly Asn Arg Asn Tyr Pro Leu Ser Asp Val Leu Pro Phe Asp Ser
        1010                1015                1020

Pro Asn Val Ile Gln Ala Asp Glu Glu Cys Ser Ser Thr Glu Ile
        1025                1030                1035

Arg Ser Leu Leu Glu Lys Leu Ala Val Leu Lys Gly
        1040                1045                1050

<210> SEQ ID NO 15
<211> LENGTH: 1053
<212> TYPE: PRT
<213> ORGANISM: Solanum tuberosum

<400> SEQUENCE: 15

Met Ala Gly Asn Asp Trp Ile Asn Ser Tyr Leu Glu Ala Ile Leu Asp
1               5                   10                  15

Val Gly Pro Gly Leu Asp Asp Lys Ser Ser Leu Leu Arg Glu
            20                  25                  30
```

```
Arg Gly Arg Phe Ser Pro Thr Arg Tyr Phe Val Glu Val Ile Thr
            35                  40                  45
Gly Phe Asp Glu Thr Asp Leu His Arg Ser Trp Ile Arg Ala Gln Ala
 50                  55                  60
Thr Arg Ser Pro Gln Arg Arg Asn Thr Arg Leu Glu Asn Met Cys Trp
 65                  70                  75                  80
Arg Ile Trp Asn Leu Ala Arg Gln Lys Lys Gln Leu Glu Gly Glu Gln
                 85                  90                  95
Ala Gln Trp Met Ala Lys Arg Arg Gln Glu Arg Glu Arg Gly Arg Arg
                100                 105                 110
Glu Ala Val Ala Asp Met Ser Glu Asp Leu Ser Glu Gly Glu Lys Gly
            115                 120                 125
Asp Ile Val Ala Asp Met Ser Ser His Gly Glu Ser Thr Arg Gly Arg
130                 135                 140
Leu Pro Arg Ile Ser Ser Val Glu Thr Met Glu Ala Trp Val Ser Gln
145                 150                 155                 160
Gln Arg Gly Lys Lys Leu Tyr Ile Val Leu Ile Ser Leu His Gly Leu
                165                 170                 175
Ile Arg Gly Glu Asn Met Glu Leu Gly Arg Asp Ser Asp Thr Gly Gly
                180                 185                 190
Gln Val Lys Tyr Val Val Glu Leu Ala Arg Ala Leu Gly Ser Met Pro
            195                 200                 205
Gly Val Tyr Arg Val Asp Leu Leu Thr Arg Gln Val Ser Ser Pro Glu
210                 215                 220
Val Asp Trp Ser Tyr Gly Glu Pro Thr Glu Leu Ala Pro Ile Ser Thr
225                 230                 235                 240
Asp Gly Leu Met Thr Glu Met Gly Glu Ser Ser Gly Ala Tyr Ile Ile
                245                 250                 255
Arg Ile Pro Phe Gly Pro Arg Glu Lys Tyr Ile Pro Lys Glu Gln Leu
                260                 265                 270
Trp Pro Tyr Ile Pro Glu Phe Val Asp Gly Ala Leu Asn His Ile Ile
            275                 280                 285
Gln Met Ser Lys Val Leu Gly Glu Gln Ile Gly Ser Gly Tyr Pro Val
290                 295                 300
Trp Pro Val Ala Ile His Gly His Tyr Ala Asp Ala Gly Asp Ser Ala
305                 310                 315                 320
Ala Leu Leu Ser Gly Ala Leu Asn Val Pro Met Leu Phe Thr Gly His
                325                 330                 335
Ser Leu Gly Arg Asp Lys Leu Glu Gln Leu Leu Ala Gln Gly Arg Lys
                340                 345                 350
Ser Lys Asp Glu Ile Asn Ser Thr Tyr Lys Ile Met Arg Arg Ile Glu
            355                 360                 365
Ala Glu Glu Leu Thr Leu Asp Ala Ser Glu Ile Val Ile Thr Ser Thr
370                 375                 380
Arg Gln Glu Ile Asp Glu Gln Trp Arg Leu Tyr Asp Gly Phe Asp Pro
385                 390                 395                 400
Ile Leu Glu Arg Lys Leu Arg Ala Arg Ile Lys Arg Asn Val Ser Cys
                405                 410                 415
Tyr Gly Arg Phe Met Pro Arg Met Ala Val Ile Pro Pro Gly Met Glu
            420                 425                 430
Phe His His Ile Val Pro His Glu Gly Asp Met Asp Gly Glu Thr Glu
435                 440                 445
Gly Ser Glu Asp Gly Lys Thr Pro Asp Pro Pro Ile Trp Ala Glu Ile
450                 455                 460
```

```
Met Arg Phe Phe Ser Asn Pro Arg Lys Pro Met Ile Leu Ala Leu Ala
465                 470                 475                 480

Arg Pro Asp Pro Lys Lys Asn Leu Thr Thr Leu Val Lys Ala Phe Gly
            485                 490                 495

Glu Cys Arg Pro Leu Arg Asp Leu Ala Asn Leu Thr Leu Ile Met Gly
            500                 505                 510

Asn Arg Asp Asn Ile Asp Glu Met Ser Ser Thr Asn Ser Ala Leu Leu
            515                 520                 525

Leu Ser Ile Leu Lys Met Ile Asp Lys Tyr Asp Leu Tyr Gly Gln Val
530                 535                 540

Ala Tyr Pro Lys His His Lys Gln Ser Asp Val Pro Asp Ile Tyr Arg
545                 550                 555                 560

Leu Ala Ala Lys Thr Lys Gly Val Phe Ile Asn Pro Ala Phe Ile Glu
                565                 570                 575

Pro Phe Gly Leu Thr Leu Ile Glu Ala Ala Tyr Gly Leu Pro Met
            580                 585                 590

Val Ala Thr Lys Asn Gly Gly Pro Val Asp Ile His Arg Val Leu Asp
            595                 600                 605

Asn Gly Leu Leu Val Asp Pro His Asp Gln Gln Ala Ile Ala Asp Ala
610                 615                 620

Leu Leu Lys Leu Val Ala Asp Lys Gln Leu Trp Ala Lys Cys Arg Ala
625                 630                 635                 640

Asn Gly Leu Lys Asn Ile His Leu Phe Ser Trp Pro Glu His Cys Lys
                645                 650                 655

Thr Tyr Leu Ser Arg Ile Ala Ser Cys Lys Pro Arg Gln Pro Arg Trp
            660                 665                 670

Leu Arg Ser Ile Asp Asp Asp Glu Asn Ser Glu Thr Asp Ser Pro
            675                 680                 685

Ser Asp Ser Leu Arg Asp Ile His Asp Ile Ser Leu Asn Leu Arg Phe
690                 695                 700

Ser Leu Asp Gly Glu Lys Asn Asp Asn Lys Glu Asn Ala Asp Asn Thr
705                 710                 715                 720

Leu Asp Pro Glu Val Arg Arg Ser Lys Leu Glu Asn Ala Val Leu Ser
                725                 730                 735

Leu Ser Lys Gly Ala Leu Lys Ser Thr Ser Lys Ser Trp Ser Ser Asp
            740                 745                 750

Lys Ala Asp Gln Asn Pro Gly Ala Gly Lys Phe Pro Ala Ile Arg Arg
            755                 760                 765

Arg Arg His Ile Phe Val Ile Ala Val Asp Cys Asp Ala Ser Ser Gly
            770                 775                 780

Leu Ser Gly Ser Val Lys Lys Ile Phe Glu Ala Val Glu Lys Glu Arg
785                 790                 795                 800

Ala Glu Gly Ser Ile Gly Phe Ile Leu Ala Thr Ser Phe Asn Ile Ser
                805                 810                 815

Glu Val Gln Ser Phe Leu Leu Ser Glu Gly Met Asn Pro Thr Asp Phe
            820                 825                 830

Asp Ala Tyr Ile Cys Asn Ser Gly Gly Asp Leu Tyr Tyr Ser Ser Phe
            835                 840                 845

His Ser Glu Gln Asn Pro Phe Val Val Asp Leu Tyr Tyr His Ser His
            850                 855                 860

Ile Glu Tyr Arg Trp Gly Gly Glu Gly Leu Arg Lys Thr Leu Val Arg
865                 870                 875                 880

Trp Ala Ala Ser Ile Ile Asp Lys Asn Gly Glu Asn Gly Asp His Ile
```

885                 890                 895
Val Val Glu Asp Glu Asp Asn Ser Ala Asp Tyr Cys Tyr Thr Phe Lys
                900                 905                 910

Val Cys Lys Pro Gly Thr Val Pro Pro Ser Lys Glu Leu Arg Lys Val
            915                 920                 925

Met Arg Ile Gln Ala Leu Arg Cys His Ala Val Tyr Cys Gln Asn Gly
        930                 935                 940

Ser Arg Ile Asn Val Ile Pro Val Leu Ala Ser Arg Ser Gln Ala Leu
945                 950                 955                 960

Arg Tyr Leu Tyr Leu Arg Trp Gly Met Asp Leu Ser Lys Leu Val Val
                965                 970                 975

Phe Val Gly Glu Ser Gly Asp Thr Asp Tyr Glu Gly Leu Ile Gly Gly
            980                 985                 990

Leu Arg Lys Ala Val Ile Met Lys Gly Leu Cys Thr Asn Ala Ser Ser
        995                 1000                1005

Leu Ile His Gly Asn Arg Asn Tyr Pro Leu Ser Asp Val Leu Pro
        1010                1015                1020

Phe Asp Ser Pro Asn Val Ile Gln Ala Asp Glu Glu Cys Ser Ser
        1025                1030                1035

Thr Glu Ile Arg Cys Leu Leu Glu Lys Leu Ala Val Leu Lys Gly
        1040                1045                1050

<210> SEQ ID NO 16
<211> LENGTH: 1054
<212> TYPE: PRT
<213> ORGANISM: Nicotiana tabacum

<400> SEQUENCE: 16

Met Ala Gly Asn Asp Trp Ile Asn Ser Tyr Leu Glu Ala Ile Leu Asp
1               5                   10                  15

Val Gly Pro Gly Ile Glu Asp Lys Lys Ser Ser Leu Leu Leu Arg Glu
            20                  25                  30

Arg Gly Arg Phe Ser Pro Thr Arg Tyr Phe Val Glu Glu Val Ile Thr
        35                  40                  45

Gly Phe Asp Glu Thr Asp Leu His Arg Ser Trp Val Arg Ala Gln Ala
    50                  55                  60

Thr Arg Ser Pro Gln Glu Arg Asn Thr Arg Leu Glu Asn Met Cys Trp
65                  70                  75                  80

Arg Ile Trp Asn Leu Ala Arg Gln Lys Lys Gln Leu Glu Gly Glu Gln
                85                  90                  95

Ala Gln Trp Met Ala Lys Arg Arg Gln Glu Arg Glu Lys Gly Arg Arg
            100                 105                 110

Glu Ala Val Ala Asp Met Ser Glu Asp Leu Ser Glu Gly Glu Lys Gly
        115                 120                 125

Asp Val Val Ser Asp Ile Pro Ser His Gly Glu Ser Thr Lys Gly Arg
    130                 135                 140

Leu Pro Arg Ile Ser Ser Val Glu Thr Met Glu Ala Trp Val Asn Gln
145                 150                 155                 160

Gln Arg Gly Lys Lys Leu Tyr Ile Val Leu Ile Ser Leu His Gly Leu
                165                 170                 175

Ile Arg Gly Glu Asn Met Glu Leu Gly Arg Asp Ser Asp Thr Gly Gly
            180                 185                 190

Gln Val Lys Tyr Val Val Glu Leu Ala Arg Ala Leu Gly Ser Met Pro
        195                 200                 205

Gly Val Tyr Arg Val Asp Leu Leu Thr Arg Gln Val Ser Ser Pro Glu

```
            210                 215                 220
Val Asp Trp Ser Tyr Gly Glu Pro Thr Glu Met Leu Pro Pro Arg Ser
225                 230                 235                 240

Thr Glu Gly Leu Met Thr Glu Met Gly Glu Ser Ser Gly Ala Tyr Ile
                245                 250                 255

Ile Arg Ile Pro Phe Gly Pro Arg Glu Lys Tyr Ile Pro Lys Glu Gln
                260                 265                 270

Leu Trp Pro Tyr Ile Pro Glu Phe Val Asp Gly Ala Leu Asn His Ile
            275                 280                 285

Ile Gln Met Ser Lys Val Leu Gly Glu Gln Ile Gly Asn Gly Tyr Pro
        290                 295                 300

Val Trp Pro Val Ala Ile His Gly His Tyr Ala Asp Ala Gly Asp Ser
305                 310                 315                 320

Ala Ala Leu Leu Ser Gly Ala Leu Asn Val Pro Met Leu Phe Thr Gly
                325                 330                 335

His Ser Leu Gly Arg Asp Lys Leu Asp Gln Leu Leu Arg Gln Gly Arg
                340                 345                 350

Leu Ser Lys Asp Glu Ile Asn Ser Thr Tyr Lys Ile Met Arg Arg Ile
            355                 360                 365

Glu Ala Glu Glu Leu Thr Leu Asp Ala Ser Glu Ile Val Ile Thr Ser
        370                 375                 380

Thr Arg Gln Glu Ile Asp Glu Gln Trp Arg Leu Tyr Asp Gly Phe Asp
385                 390                 395                 400

Pro Ile Leu Glu Arg Lys Leu Arg Ala Arg Ile Lys Arg Asn Val Ser
                405                 410                 415

Cys Tyr Gly Arg Phe Met Pro Arg Met Ala Val Ile Pro Pro Gly Met
                420                 425                 430

Glu Phe His His Ile Val Pro His Glu Gly Asp Met Asp Gly Glu Thr
            435                 440                 445

Glu Gly Thr Glu Asp Gly Lys Ala Pro Asp Pro Ile Trp Thr Glu
        450                 455                 460

Ile Met Arg Phe Phe Ser Asn Pro Arg Lys Pro Met Ile Leu Ala Leu
465                 470                 475                 480

Ala Arg Pro Asp Pro Lys Lys Asn Leu Thr Thr Leu Val Lys Ala Phe
                485                 490                 495

Gly Glu Cys Arg Pro Leu Arg Glu Leu Ala Asn Leu Met Leu Ile Met
                500                 505                 510

Gly Asn Arg Asp Asn Ile Asp Glu Met Ser Ser Thr Asn Ser Ser Val
            515                 520                 525

Leu Leu Ser Ile Leu Lys Met Ile Asp Lys Tyr Asp Leu Tyr Gly Gln
        530                 535                 540

Val Ala Tyr Pro Lys His His Lys Gln Ala Asp Val Pro Asp Ile Tyr
545                 550                 555                 560

Arg Leu Ala Ala Lys Thr Lys Gly Val Phe Ile Asn Pro Ala Phe Ile
                565                 570                 575

Glu Pro Phe Gly Leu Thr Leu Ile Glu Ala Ala Tyr Gly Leu Pro
                580                 585                 590

Met Val Ala Thr Lys Asn Gly Gly Pro Val Asp Ile His Arg Val Leu
            595                 600                 605

Asp Asn Gly Leu Leu Val Asp Pro His Asp Gln Gln Ala Ile Ala Asp
        610                 615                 620

Ala Leu Leu Lys Leu Val Ala Asp Lys His Leu Trp Ala Lys Cys Arg
625                 630                 635                 640
```

-continued

```
Ala Asn Gly Leu Lys Asn Ile His Leu Phe Ser Trp Pro Glu His Cys
            645                 650                 655

Lys Thr Tyr Leu Ser Arg Ile Ala Ser Cys Lys Pro Arg Gln Pro Arg
            660                 665                 670

Trp Leu Arg Asn Asp Asp Asp Glu Asn Ser Glu Thr Asp Ser
            675                 680                 685

Pro Ser Asp Ser Leu Arg Asp Ile His Asp Ile Ser Leu Asn Leu Arg
            690                 695                 700

Phe Ser Leu Asp Gly Glu Lys Asn Asp Asn Lys Glu Asn Ala Asp Asn
705                 710                 715                 720

Thr Leu Asp Pro Glu Val Arg Lys Ser Lys Leu Glu Asn Ala Val Leu
                    725                 730                 735

Ser Trp Ser Lys Gly Val Leu Lys Ser Thr Pro Lys Ala Trp Ser Ser
                    740                 745                 750

Asp Lys Gly Asp Gln Asn Ser Gly Pro Gly Lys Phe Pro Ala Ile Arg
            755                 760                 765

Arg Arg Arg His Ile Phe Val Ile Ala Val Asp Cys Asp Ala Ser Ser
            770                 775                 780

Gly Leu Ser Glu Ser Val Arg Lys Ile Phe Glu Ala Val Glu Lys Glu
785                 790                 795                 800

Arg Ala Glu Gly Ser Ile Gly Phe Ile Leu Ala Ser Ser Phe Asn Ile
                    805                 810                 815

Ser Gln Val Gln Ser Phe Leu Val Ser Glu Gly Met Lys Pro Thr Asp
                    820                 825                 830

Phe Asp Ala Tyr Ile Cys Asn Ser Gly Gly Asp Leu Tyr Tyr Ser Ser
            835                 840                 845

Phe His Ser Glu Gln Asn Pro Phe Val Val Asp Leu Tyr Tyr His Ser
            850                 855                 860

His Ile Glu Tyr Arg Trp Gly Gly Glu Gly Leu Arg Lys Thr Leu Val
865                 870                 875                 880

Arg Trp Ala Ala Ser Ile Ile Asp Lys Lys Gly Glu Asn Glu Asp His
                    885                 890                 895

Ile Val Val Glu Asp Glu Asp Asn Ser Ala Asp Tyr Cys Tyr Thr Phe
                    900                 905                 910

Lys Val Arg Lys Leu Gly Thr Val Pro Pro Ala Lys Glu Leu Arg Lys
            915                 920                 925

Leu Met Arg Ile Gln Ala Leu Arg Cys His Ala Val Tyr Cys Gln Asn
930                 935                 940

Gly Ser Arg Ile Asn Val Ile Pro Val Leu Ala Ser Arg Ser Gln Ala
945                 950                 955                 960

Leu Arg Tyr Leu Tyr Leu Arg Trp Gly Met Asp Leu Ser Lys Leu Val
                    965                 970                 975

Val Phe Val Gly Glu Ser Gly Asp Thr Asp Tyr Glu Gly Leu Ile Gly
                    980                 985                 990

Gly Leu Arg Lys Ala Val Ile Met Lys Gly Leu Cys Ala Ser Ala Ser
            995                 1000                1005

Ser Leu Ile His Gly Asn Ser Asn Tyr Pro Leu Ser Asp Val Leu
            1010                1015                1020

Pro Phe Asp Ser Pro Asn Val Val Gln Ser Ala Glu Glu Cys Ser
            1025                1030                1035

Ser Thr Glu Ile Arg Ser Ser Leu Glu Lys Leu Gly Val Leu Lys
            1040                1045                1050

Gly
```

```
<210> SEQ ID NO 17
<211> LENGTH: 1054
<212> TYPE: PRT
<213> ORGANISM: Lycopersicon esculentum

<400> SEQUENCE: 17

Met Ala Gly Asn Asp Trp Ile Asn Ser Tyr Leu Glu Ala Ile Leu Asp
1               5                   10                  15

Val Gly Pro Gly Leu Asp Asp Lys Lys Ser Ser Leu Leu Leu Arg Glu
            20                  25                  30

Arg Gly Arg Phe Ser Pro Thr Arg Tyr Phe Val Glu Glu Val Ile Thr
        35                  40                  45

Gly Phe Asp Glu Thr Asp Leu His Arg Ser Trp Ile Arg Ala Gln Ala
    50                  55                  60

Thr Arg Ser Pro Gln Glu Arg Asn Thr Arg Leu Glu Asn Met Cys Trp
65                  70                  75                  80

Arg Ile Trp Asn Leu Ala Arg Arg Lys Lys Gln Leu Glu Gly Glu Gln
                85                  90                  95

Ala Arg Trp Met Ala Lys Arg Arg Gln Glu Arg Glu Arg Gly Arg Arg
            100                 105                 110

Glu Ala Val Ala Asp Met Ser Glu Asp Leu Ser Arg Gly Glu Lys Gly
        115                 120                 125

Asp Ile Val Thr Asp Met Ser Ser Asn Gly Glu Ser Thr Arg Gly Arg
    130                 135                 140

Leu Pro Arg Ile Ser Ser Val Glu Thr Met Glu Ala Trp Val Ser Gln
145                 150                 155                 160

Gln Arg Gly Lys Lys Leu Tyr Ile Val Leu Ile Ser Leu Thr Gly Leu
                165                 170                 175

Ile Arg Gly Glu Asp Met Glu Leu Gly Arg Asp Thr Asp Thr Gly Gly
            180                 185                 190

Gln Val Lys Tyr Val Val Glu Leu Ala Arg Ala Leu Gly Ser Met Pro
        195                 200                 205

Gly Val Tyr Arg Val Asp Leu Leu Thr Arg Gln Val Ser Ser Pro Glu
    210                 215                 220

Val Asp Trp Ser Tyr Gly Glu Pro Thr Glu Met Leu Thr Pro Ile Ser
225                 230                 235                 240

Thr Asp Gly Leu Met Ser Glu Met Gly Glu Ser Ser Gly Ala Tyr Ile
                245                 250                 255

Ile Arg Ile Pro Phe Gly Pro Arg Glu Lys Tyr Ile Pro Lys Glu Gln
            260                 265                 270

Leu Trp Pro Tyr Ile Pro Glu Phe Val Asp Gly Ala Leu Asn His Ile
        275                 280                 285

Ile Gln Met Ser Lys Val Leu Gly Glu Gln Ile Gly Asn Gly His Pro
    290                 295                 300

Val Trp Pro Gly Ala Ile His Gly His Tyr Ala Asp Ala Gly Asp Ser
305                 310                 315                 320

Ala Ala Leu Leu Ser Gly Ala Leu Asn Val Pro Met Leu Phe Thr Gly
                325                 330                 335

His Ser Leu Gly Arg Asp Lys Leu Glu Gln Leu Leu Arg Gln Gly Arg
            340                 345                 350

Leu Ser Lys Asp Glu Ile Asn Ser Thr Tyr Lys Ile Met Arg Arg Ile
        355                 360                 365

Glu Ala Glu Glu Leu Thr Leu Asp Ala Ser Glu Ile Val Ile Thr Ser
    370                 375                 380
```

```
Thr Arg Gln Glu Ile Asp Glu Gln Trp Arg Leu Tyr Asp Gly Phe Asp
385                 390                 395                 400

Pro Ile Leu Glu Arg Lys Leu Arg Ala Arg Ile Lys Arg Asn Val Ser
            405                 410                 415

Cys Tyr Gly Arg Phe Met Pro Arg Met Ala Val Ile Pro Pro Gly Met
        420                 425                 430

Glu Phe His His Ile Val Pro His Glu Gly Asp Met Asp Gly Asp Thr
        435                 440                 445

Glu Gly Ser Glu Asp Gly Lys Ile Pro Asp Pro Ile Trp Ala Glu
    450                 455                 460

Ile Met Arg Phe Phe Ser Asn Pro Arg Lys Pro Met Asn Leu Ala Leu
465                 470                 475                 480

Ala Arg Pro Asp Pro Lys Lys Asn Leu Thr Thr Leu Val Lys Ala Phe
            485                 490                 495

Gly Glu Cys Arg Pro Leu Arg Glu Leu Ala Asn Leu Thr Leu Ile Met
        500                 505                 510

Gly Asn Arg Asp Asn Ile Asp Glu Met Ser Ser Thr Asn Ser Ala Leu
        515                 520                 525

Leu Leu Ser Ile Leu Lys Met Ile Asp Lys Tyr Asp Leu Tyr Gly Gln
530                 535                 540

Val Ala Tyr Pro Lys His His Lys Gln Ser Asp Val Pro Asp Ile Tyr
545                 550                 555                 560

Arg Leu Ala Ala Lys Thr Lys Gly Val Phe Ile Asn Pro Ala Phe Ile
            565                 570                 575

Glu Pro Phe Gly Leu Thr Leu Ile Glu Ala Ala Tyr Gly Leu Pro
        580                 585                 590

Met Val Ala Thr Lys Asn Gly Gly Pro Val Asp Ile His Arg Val Leu
    595                 600                 605

Asp Asn Gly Leu Leu Val Asp Pro His Asp Gln Gln Ala Ile Ala Asp
    610                 615                 620

Ala Leu Leu Lys Leu Val Ala Asp Lys Gln Leu Trp Ala Lys Cys Arg
625                 630                 635                 640

Ala Asn Gly Leu Lys Asn Ile His Leu Phe Ser Trp Pro Glu His Cys
            645                 650                 655

Lys Thr Tyr Leu Ser Arg Ile Ala Ser Cys Lys Pro Arg Gln Pro Arg
        660                 665                 670

Trp Leu Arg Pro Gly Asp Asp Asp Glu Asn Ser Glu Thr Asp Ser
    675                 680                 685

Pro Ser Asp Ser Leu Arg Asp Ile His Asp Ile Ser Leu Asn Leu Arg
        690                 695                 700

Phe Ser Leu Asp Gly Glu Lys Asn Asp Asn Lys Glu Asn Ala Asp Ser
705                 710                 715                 720

Thr Leu Asp Pro Glu Val Arg Lys Ser Lys Leu Glu Asn Ala Val Leu
            725                 730                 735

Ser Leu Ser Lys Gly Ala Pro Lys Ser Thr Ser Lys Ser Trp Ser Ser
        740                 745                 750

Asp Lys Ala Asp Gln Asn Pro Gly Ala Gly Lys Phe Pro Ala Ile Arg
        755                 760                 765

Arg Arg Arg His Ile Phe Val Ile Ala Val Asp Cys Asp Ala Ser Ser
770                 775                 780

Gly Leu Ser Gly Ser Val Lys Lys Ile Phe Glu Ala Val Glu Lys Glu
785                 790                 795                 800

Arg Ser Glu Gly Ser Ile Gly Phe Ile Leu Ala Ser Ser Phe Asn Ile
            805                 810                 815
```

```
Ser Glu Val Gln Ser Phe Leu Val Ser Glu Gly Met Ser Pro Thr Asp
            820                 825                 830

Phe Asp Ala Tyr Ile Cys Asn Ser Gly Gly Asp Leu Tyr Tyr Ser Ser
            835                 840                 845

Phe His Ser Glu Gln Asn Pro Phe Val Val Asp Leu Tyr His Ser
    850                 855                 860

His Ile Glu Tyr Arg Trp Gly Gly Gly Leu Arg Lys Thr Leu Val
865                 870                 875                 880

Arg Trp Ala Ala Ser Ile Thr Asp Lys Asn Gly Glu Asn Gly Glu His
                885                 890                 895

Ile Val Val Glu Asp Glu Asp Asn Ser Ala Asp Tyr Cys Tyr Thr Phe
            900                 905                 910

Lys Val Cys Lys Pro Gly Lys Val Pro Pro Ala Lys Glu Leu Arg Lys
            915                 920                 925

Val Met Arg Ile Gln Ala Leu Arg Cys His Ala Val Tyr Cys Gln Asn
            930                 935                 940

Gly Ser Arg Ile Asn Met Ile Pro Val Leu Ala Ser Arg Ser Gln Ala
945                 950                 955                 960

Leu Arg Tyr Leu Tyr Leu Arg Trp Gly Met Asp Leu Ser Lys Leu Val
                965                 970                 975

Val Phe Val Gly Glu Ser Gly Asp Thr Asp Tyr Glu Gly Leu Ile Gly
            980                 985                 990

Gly Leu Arg Lys Ala Val Ile Met Lys Gly Leu Cys Thr Asn Ala Ser
        995                 1000                1005

Ser Leu Ile His Gly Asn Arg Asn Tyr Pro Leu Ser Asp Val Leu
    1010                1015                1020

Pro Phe Asp Ser Pro Asn Val Ile Gln Ala Asp Glu Glu Cys Ser
    1025                1030                1035

Ser Thr Glu Ile Arg Ser Leu Leu Glu Lys Leu Ala Val Leu Lys
    1040                1045                1050

Gly

<210> SEQ ID NO 18
<211> LENGTH: 422
<212> TYPE: PRT
<213> ORGANISM: Arabidopsis thaliana

<400> SEQUENCE: 18

Met Glu Arg Leu Thr Ser Pro Pro Arg Leu Met Ile Val Ser Asp Leu
1               5                   10                  15

Asp His Thr Met Val Asp His His Asp Pro Glu Asn Leu Ser Leu Leu
            20                  25                  30

Arg Phe Asn Ser Leu Trp Glu His Ala Tyr Arg His Asp Ser Leu Leu
        35                  40                  45

Val Phe Ser Thr Gly Arg Ser Pro Thr Leu Tyr Lys Glu Leu Arg Lys
    50                  55                  60

Glu Lys Pro Leu Leu Thr Pro Asp Ile Thr Ile Met Ser Val Gly Thr
65                  70                  75                  80

Glu Ile Thr Tyr Gly Asn Ser Met Val Pro Asp His Gly Trp Val Glu
                85                  90                  95

Ala Leu Asn Asn Lys Trp Asp Leu Gly Ile Val Lys Gln Glu Ala Ser
            100                 105                 110

Asn Phe Pro Glu Leu Lys Leu Gln Ala Glu Thr Glu Gln Arg Pro His
        115                 120                 125
```

```
Lys Val Ser Phe Tyr Val Glu Lys Ser Lys Ala Gln Glu Val Thr Lys
            130                 135                 140

Glu Leu Ser Gln Arg Phe Leu Lys Arg Gly Leu Asp Val Lys Ile Ile
145                 150                 155                 160

Tyr Ser Gly Gly Met Asp Leu Asp Ile Leu Pro Gln Gly Ala Gly Lys
                165                 170                 175

Gly Gln Ala Leu Ala Tyr Leu Leu Lys Lys Leu Lys Thr Glu Gly Lys
                180                 185                 190

Leu Pro Val Asn Thr Leu Ala Cys Gly Asp Ser Gly Asn Asp Ala Glu
            195                 200                 205

Leu Phe Ser Ile Pro Asp Val Tyr Gly Val Met Val Ser Asn Ala Gln
            210                 215                 220

Glu Glu Leu Leu Lys Trp His Ala Glu Asn Ala Lys Asp Asn Pro Lys
225                 230                 235                 240

Val Ile His Ala Lys Glu Arg Cys Ala Gly Gly Ile Ile Gln Ala Ile
                245                 250                 255

Gly His Phe Lys Leu Gly Pro Asn Leu Ser Pro Arg Asp Val Ser Asp
                260                 265                 270

Phe Leu Glu Ile Lys Val Glu Asn Val Asn Pro Gly His Glu Val Val
            275                 280                 285

Lys Phe Phe Leu Phe Tyr Glu Arg Trp Arg Arg Gly Glu Val Glu Asn
290                 295                 300

Ser Glu Ala Tyr Thr Ala Ser Leu Lys Ala Ser Val His Pro Gly Gly
305                 310                 315                 320

Val Phe Val His Pro Ser Gly Thr Glu Lys Ser Leu Arg Asp Thr Ile
                325                 330                 335

Asp Glu Leu Arg Lys Tyr His Gly Asp Lys Gln Gly Lys Lys Phe Arg
                340                 345                 350

Val Trp Ala Asp Gln Val Leu Ala Thr Asp Thr Pro Gly Thr Trp
            355                 360                 365

Ile Val Lys Leu Asp Lys Trp Glu Gln Asp Gly Asp Glu Arg Arg Cys
            370                 375                 380

Cys Thr Thr Thr Val Lys Phe Thr Ser Lys Glu Gly Glu Gly Leu Val
385                 390                 395                 400

Trp Glu His Val Gln Gln Thr Trp Ser Lys Thr Met Val Lys Asp
                405                 410                 415

Asp Ser Ser Trp Ile Ile
                420

<210> SEQ ID NO 19
<211> LENGTH: 425
<212> TYPE: PRT
<213> ORGANISM: Lycopersicon esculentum

<400> SEQUENCE: 19

Met Asp Arg Leu Thr Ser Ala Ala Arg Leu Met Ile Val Ser Asp Leu
1               5                   10                  15

Asp His Thr Met Val Asp His His Asp Ser Glu Asn Leu Ser Leu Leu
                20                  25                  30

Arg Phe Asn Ala Leu Trp Glu Ala Asn Tyr Arg Asp Asn Ser Leu Leu
            35                  40                  45

Val Phe Ser Thr Gly Arg Ser Pro Thr Leu Tyr Lys Glu Leu Arg Lys
        50                  55                  60

Glu Lys Pro Met Leu Thr Pro Asp Ile Thr Ile Met Ser Val Gly Thr
65                  70                  75                  80
```

```
Glu Ile Thr Tyr Gly Asn Ala Met Val Pro Asp Asp Gly Trp Glu Thr
                85                  90                  95

Phe Leu Asn Asn Lys Trp Asp Arg Lys Ile Val Thr Glu Glu Thr Ser
            100                 105                 110

Lys Phe Pro Glu Leu Ser Leu Gln Ser Glu Thr Glu Gln Arg Pro His
        115                 120                 125

Lys Val Ser Phe Tyr Val Gln Lys Glu Lys Ala Gln Asp Ile Met Lys
    130                 135                 140

Thr Leu Ser Lys Arg Leu Lys Glu Arg Gly Leu Asp Val Lys Ile Ile
145                 150                 155                 160

Tyr Ser Gly Gly Met Asp Leu Asp Ile Leu Pro Gln Gly Ala Gly Lys
                165                 170                 175

Gly Gln Ala Leu Ala Tyr Leu Leu Lys Lys Leu Lys Ser Glu Gly Lys
            180                 185                 190

Leu Pro Ser Asn Thr Leu Ala Cys Gly Asp Ser Gly Asn Asp Ala Glu
        195                 200                 205

Leu Phe Ser Ile Pro Asp Val Tyr Gly Val Met Val Ala Asn Ala Gln
    210                 215                 220

Glu Glu Leu Leu Gln Trp His Ala Ala Asn Ala Lys Asn Asn Pro Lys
225                 230                 235                 240

Val Ile His Ala Ser Glu Arg Cys Ala Ala Gly Ile Ile Gln Ala Ile
                245                 250                 255

Gly His Phe Asn Leu Gly Pro Ser Thr Ser Pro Arg Asp Val Thr Asp
            260                 265                 270

Leu Ser Asp Cys Lys Met Asp Asn Phe Val Pro Ala Tyr Glu Val Val
        275                 280                 285

Lys Phe Tyr Leu Phe Phe Glu Lys Trp Arg Arg Gly Glu Ile Glu His
    290                 295                 300

Ser Glu His Tyr Leu Ser Asn Leu Lys Ala Val Cys Arg Pro Ser Gly
305                 310                 315                 320

Thr Phe Val His Pro Ser Gly Val Glu Lys Ser Leu Gln Glu Cys Val
                325                 330                 335

Thr Thr Phe Gly Thr Cys His Ala Asp Lys His Gly Lys Gln Tyr Arg
            340                 345                 350

Val Trp Val Asp Gln Val Leu Pro Ser Gln Val Gly Ser Asp Ser Trp
        355                 360                 365

Leu Val Ser Phe Lys Lys Trp Glu Leu Ser Gly Glu Asn Arg Arg Cys
    370                 375                 380

Cys Ile Thr Thr Val Leu Leu Ser Ser Lys Asn Lys Thr Val Ala Asp
385                 390                 395                 400

Gly Leu Thr Trp Thr His Val His Gln Thr Trp Leu His Asp Asp Ala
                405                 410                 415

Ser Ser Asp Ser Ala Ser Trp Phe Phe
            420                 425

<210> SEQ ID NO 20
<211> LENGTH: 23
<212> TYPE: DNA
<213> ORGANISM: Artificial Sequence
<220> FEATURE:
<223> OTHER INFORMATION: Degenerate oligonucleotide SPS-3
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
```

```
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 20
ggncgngayt ctgayacngg tgg                                            23

<210> SEQ ID NO 21
<211> LENGTH: 27
<212> TYPE: DNA
<213> ORGANISM: Artificial Sequence
<220> FEATURE:
<223> OTHER INFORMATION: Degenerate oligonucleotide SPS-4
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 21
tggacgacay tcnccaaang cyttnac                                        27

<210> SEQ ID NO 22
<211> LENGTH: 20
<212> TYPE: DNA
<213> ORGANISM: Artificial Sequence
<220> FEATURE:
<223> OTHER INFORMATION: Primer cDNAC1-1

<400> SEQUENCE: 22
aacttgcaag ggctttaggt                                                20

<210> SEQ ID NO 23
<211> LENGTH: 20
<212> TYPE: DNA
<213> ORGANISM: Artificial Sequence
<220> FEATURE:
<223> OTHER INFORMATION: Primer cDNAC1-2

<400> SEQUENCE: 23
aagggctagt atcataggct                                                20

<210> SEQ ID NO 24
<211> LENGTH: 20
<212> TYPE: DNA
<213> ORGANISM: Artificial Sequence
<220> FEATURE:
<223> OTHER INFORMATION: Primer cDNAD1-1

<400> SEQUENCE: 24
agcttgctaa ggcacttgct                                                20

<210> SEQ ID NO 25
<211> LENGTH: 20
<212> TYPE: DNA
<213> ORGANISM: Artificial Sequence
<220> FEATURE:
<223> OTHER INFORMATION: Primer cDNAD1-2

<400> SEQUENCE: 25
```

-continued caatgctaga atcattggct                                                    20

<210> SEQ ID NO 26
<211> LENGTH: 22
<212> TYPE: DNA
<213> ORGANISM: Artificial Sequence
<220> FEATURE:
<223> OTHER INFORMATION: Primer AP1

<400> SEQUENCE: 26
gtaatacgac tcactatagg gc                                                 22

<210> SEQ ID NO 27
<211> LENGTH: 19
<212> TYPE: DNA
<213> ORGANISM: Artificial Sequence
<220> FEATURE:
<223> OTHER INFORMATION: Primer AP2

<400> SEQUENCE: 27
actatagggc acgcgtggt                                                     19

<210> SEQ ID NO 28
<211> LENGTH: 28
<212> TYPE: DNA
<213> ORGANISM: Artificial Sequence
<220> FEATURE:
<223> OTHER INFORMATION: Primer C1-GW1

<400> SEQUENCE: 28
tacttccagt gatgatacct gcctcgta                                           28

<210> SEQ ID NO 29
<211> LENGTH: 28
<212> TYPE: DNA
<213> ORGANISM: Artificial Sequence
<220> FEATURE:
<223> OTHER INFORMATION: Primer C1-GWN1

<400> SEQUENCE: 29
tctaggaggc agcatctcag tgggttca                                           28

<210> SEQ ID NO 30
<211> LENGTH: 28
<212> TYPE: DNA
<213> ORGANISM: Artificial Sequence
<220> FEATURE:
<223> OTHER INFORMATION: Primer C1-GW3

<400> SEQUENCE: 30
ccggatccac atatttgggg agaggtct                                           28

<210> SEQ ID NO 31
<211> LENGTH: 28
<212> TYPE: DNA
<213> ORGANISM: Artificial Sequence
<220> FEATURE:
<223> OTHER INFORMATION: Primer C1-GWN3

<400> SEQUENCE: 31
tggtgtcatg cagataatgc gctacttc                                           28

<210> SEQ ID NO 32
<211> LENGTH: 29
<212> TYPE: DNA
<213> ORGANISM: Artificial Sequence
<220> FEATURE:

```
<223> OTHER INFORMATION: Primer C1-GW6

<400> SEQUENCE: 32
gcaatcgacc cctattgctc tcaccatgt                                29

<210> SEQ ID NO 33
<211> LENGTH: 28
<212> TYPE: DNA
<213> ORGANISM: Artificial Sequence
<220> FEATURE:
<223> OTHER INFORMATION: Primer C1-GWN6

<400> SEQUENCE: 33
agtcttcaga catatcagca actgcttc                                 28

<210> SEQ ID NO 34
<211> LENGTH: 28
<212> TYPE: DNA
<213> ORGANISM: Artificial Sequence
<220> FEATURE:
<223> OTHER INFORMATION: Primer C1-GW7

<400> SEQUENCE: 34
gtgagctctc tgtggttgat gttgttga                                 28

<210> SEQ ID NO 35
<211> LENGTH: 29
<212> TYPE: DNA
<213> ORGANISM: Artificial Sequence
<220> FEATURE:
<223> OTHER INFORMATION: Primer C1-GWN7

<400> SEQUENCE: 35
gtttcgaatt ctggctcaat gcaaccact                                29

<210> SEQ ID NO 36
<211> LENGTH: 30
<212> TYPE: DNA
<213> ORGANISM: Artificial Sequence
<220> FEATURE:
<223> OTHER INFORMATION: Primer cDNAC1-am3

<400> SEQUENCE: 36
atggcgggaa atgactggat aaacagttac                               30

<210> SEQ ID NO 37
<211> LENGTH: 31
<212> TYPE: DNA
<213> ORGANISM: Artificial Sequence
<220> FEATURE:
<223> OTHER INFORMATION: Primer cDNAC1-am4

<400> SEQUENCE: 37
ctagcttttg agaaccccta gcttttccaa c                             31

<210> SEQ ID NO 38
<211> LENGTH: 21
<212> TYPE: DNA
<213> ORGANISM: Artificial Sequence
<220> FEATURE:
<223> OTHER INFORMATION: Primer/Probe rpl39-F1

<400> SEQUENCE: 38
gaacaggccc atcccttatt g                                        21

<210> SEQ ID NO 39
```

```
<211> LENGTH: 17
<212> TYPE: DNA
<213> ORGANISM: Artificial Sequence
<220> FEATURE:
<223> OTHER INFORMATION: Primer/Probe rpl39-R1

<400> SEQUENCE: 39
cggcgcttgg cattgta                                                        17

<210> SEQ ID NO 40
<211> LENGTH: 16
<212> TYPE: DNA
<213> ORGANISM: Artificial Sequence
<220> FEATURE:
<223> OTHER INFORMATION: Primer/Probe rpl39-MGB1

<400> SEQUENCE: 40
atgcgcactg acaaca                                                         16

<210> SEQ ID NO 41
<211> LENGTH: 19
<212> TYPE: DNA
<213> ORGANISM: Artificial Sequence
<220> FEATURE:
<223> OTHER INFORMATION: Primer/Probe CcSPS1-R1

<400> SEQUENCE: 41
cgcaatgtta gctgttatg                                                      19

<210> SEQ ID NO 42
<211> LENGTH: 20
<212> TYPE: DNA
<213> ORGANISM: Artificial Sequence
<220> FEATURE:
<223> OTHER INFORMATION: Primer/Probe CcSPS1-F1

<400> SEQUENCE: 42
gaaattgcgg gctaggatca                                                     20

<210> SEQ ID NO 43
<211> LENGTH: 20
<212> TYPE: DNA
<213> ORGANISM: Artificial Sequence
<220> FEATURE:
<223> OTHER INFORMATION: Primer/Probe CcSPS1-MGB1

<400> SEQUENCE: 43
gccattcgag gcatgaatct                                                     20

<210> SEQ ID NO 44
<211> LENGTH: 22
<212> TYPE: DNA
<213> ORGANISM: Artificial Sequence
<220> FEATURE:
<223> OTHER INFORMATION: Primer/Probe CcSS2-F1

<400> SEQUENCE: 44
ttctgccagt cttgcctttc tt                                                  22

<210> SEQ ID NO 45
<211> LENGTH: 26
<212> TYPE: DNA
<213> ORGANISM: Artificial Sequence
<220> FEATURE:
<223> OTHER INFORMATION: Primer/Probe CcSS2-R1

<400> SEQUENCE: 45
```

```
cctaattgac acttgaacag ggacta                                          26

<210> SEQ ID NO 46
<211> LENGTH: 19
<212> TYPE: DNA
<213> ORGANISM: Artificial Sequence
<220> FEATURE:
<223> OTHER INFORMATION: Primer/Probe CcSS2-MGB1

<400> SEQUENCE: 46
ttgttggttg gttgtgtct                                                  19
```

NUCLEIC ACIDS AND PROTEINS ASSOCIATED WITH SUCROSE ACCUMULATION IN COFFEE

This is a U.S. National Application of International Application No. PCT/US06/00337, filed Aug. 17, 2006, which claims benefit of U.S. Provisional Application No. 60/709,043, filed Aug. 17, 2005, the entire contents of each of which are incorporated by reference herein.

This claims benefit of U.S. Provisional Application No. 60/709,043 filed Aug. 17, 2005, the entire contents of which are incorporated by reference herein.

FIELD OF THE INVENTION

The present invention relates to the field of agricultural biotechnology. More particularly, the invention relates to enzymes participating in sucrose metabolism in plants, coffee in particular, and the genes and nucleic acid sequences that encodes these enzymes, along with regulatory mechanisms that regulate the sucrose metabolism via these enzymes.

BACKGROUND OF THE INVENTION

Various publications, including patents, published applications and scholarly articles, cited throughout the present specification are incorporated by reference herein, in their entireties. Citations not fully set forth within the specification may be found at the end of the specification.

Sucrose plays an important role in the ultimate aroma and flavor that is delivered by a coffee grain or bean. Sucrose is a major contributor to the total free reducing sugars in coffee, and reducing sugars are important flavor precursors in coffee. During the roasting of coffee grain, reducing sugars will react with amino group containing molecules in a Maillard type reaction, which generates a significant number of products with caramel, sweet and roast/burnt-type aromas and dark colors that are typically associated with coffee flavor (Russwurm, 1969; Holscher and Steinhart, 1995; Badoud, 2000). The highest quality Arabica grain (*Coffea Arabica*) have been found to have appreciably higher levels of sucrose (between 7.3 and 11.4%) than the lowest quality Robusta grain (*Coffea canephora*) (between 4 and 5%) (Russwurm, 1969; Illy and Viani, 1995; Chahan et al., 2002; Badoud, 2000). Despite being significantly degraded during roasting, sucrose still remains in the roasted grain at concentrations of 0.4-2.8% dry weight (DW); thereby, contributing directly to coffee sweetness. A clear correlation exists between the level of sucrose in the grain and coffee flavor. Therefore, identifying and isolating the major enzymes responsible for sucrose metabolism and the underlying genetic basis for variations in sucrose metabolism will enable advances in the art of improving coffee quality.

Currently, there are no published reports on the genes or enzymes involved in sucrose metabolism in coffee. However, sucrose metabolism has been studied in tomato *Lycopersicon esculentum* (a close relative of coffee, both are members of asterid I class), especially during tomato fruit development. An overview of the enzymes directly involved in sucrose metabolism in tomato is shown in FIG. 1 (Nguyen-Quoc et al., 2001). The key reactions in this pathway are (1) the continuous rapid degradation of sucrose in the cytosol by sucrose synthase (SuSy) and cytoplasmic invertase (I), (2) sucrose synthesis by SuSy or sucrose-phosphate synthase (SPS), (3) sucrose hydrolysis in the vacuole or in the apoplast (region external to the plasma membrane, including cell walls, xylem vessels, etc) by acid invertase (vacuolar or cell wall bound) and, (4) the rapid synthesis and breakdown of starch in the amyloplast.

As in other sink organs, the pattern of sucrose unloading is not constant during tomato fruit development. At the early stages of fruit development, sucrose is unloaded intact from the phloem by the symplast pathway (direct connections between cells) and is not degraded to its composite hexoses during unloading. Both the expression and enzyme activity of SuSy are highest at this stage and are directly correlated with sucrose unloading capacity from the phloem (phenomena also called sink strength; Sun, et al., 1992; Zrenner et al., 1995). Later in fruit development, the symplastic connections are lost. Under these conditions of unloading, sucrose is rapidly hydrolyzed outside the fruit cells by the cell wall bound invertase and then the glucose and fructose products are imported into the cells by hexose transporters. Sucrose is subsequently synthesized de novo in the cytoplasm by SuSy or SPS (FIG. 1). SPS catalyses an essentially irreversible reaction in vivo due to its close association with the enzyme sucrose phosphate phosphatase (Echeverria et al., 1997). In parallel to the loss of the symplastic connections, SuSy activity decreases, and eventually becomes undetectable in fruit at the onset of ripening (Robinson et al. 1998; Wang et al. 1993). Therefore, late in the development of tomato fruit, the SPS enzyme, in association with SP, appears as the major enzymes for sucrose synthesis.

During the past decade, evidence has increasingly indicated that SuSy is responsible for the cleavage of newly imported sucrose, thereby controlling the import capacity of the fruit (N'tchobo et al., 1999) and the rate of starch synthesis. At the same time, SPS is now considered a rate limiting enzyme in the pathway providing sucrose to plant storage organs (roots, tubers and seeds) commonly referred to as sink. Together, this growing body of data strongly indicates that SuSy and SPS enzymes are important regulators of sucrose metabolism during tomato fruit development.

Alterations in carbon partitioning in plants, and most particularly improvement of sucrose levels in sink organs, have already been successfully accomplished in several plants, the most extensive and most encouraging results being obtained in tomato (*Lycopersicon esculentum*). Worrell and coworkers have made a set of constructions to test the effects of increasing SPS levels. For the principle experiments, they used a maize SPS cDNA under the control of the SSU promoter (Rubisco small subunit promoter) (Worrell, et al., 1991; Galtier et al. 1993; Foyer and Ferrario, 1994; Micallef, et al., 1995; Van Assche et al., 1999; Nguyen-Quoc et al., 1999). The total SPS activity in the leaves of the transformed plants was six times greater than that of the controls, while the total SPS activity in the mature fruit from the transformed plants was only twice than that of untransformed controls. This observation suggests that, even with a strong constitutive promoter, the level of recombinant SPS was altered in a tissue specific manner. Interestingly, some results have also suggested that the maize SPS activity was not under circadian control when this enzyme was expressed in tomato (Galtier et al., 1993). It should also be noted that SPS enzyme activity is negatively regulated at the post-translational level by phosphorylation and the level of phosphorylation varies according to the level of light and thus the light and dark phases of photosynthesis (Sugden et al., 1999; Jones et Ort, 1997). Therefore, the latter result suggests that the increase of SPS activity in the transgenic plants was both due to an overexpression of the protein and to the unregulated activity of the transfected maize SPS enzyme (i.e., the regulation by phosphorylation was perturbed). The increase in SPS activity was accompanied by a significant increase (25%) in total overall SuSy activity in 20 day old tomato fruit. The SuSy activity was measured with an assay in the direction of sucrose breakdown (Nguyen-Quoc et al.; 1999). Fruit from these transgenic tomato lines showed higher sugar content (36% increase) compared to untransformed plants (Van Assche et al., 1999). Biochemical studies have also shown that the high levels of the corn SPS activity in the plants caused a modification of carbohydrate portioning in the tomato leaves with an increase of sucrose/starch ratios and also a strong improvement in photosynthetic capacity. The tomato plants appeared to tolerate the elevated levels of SPS as there were no apparent detrimental growing effects. Other plants transformed with the construct 35SCaMV-SPS (35 S Cauliflower Mosaïc Virus) have three to five times more total SPS activity in leaves than in wild-type plants but surprisingly tomato fruit obtained from these particular transformants did not show any increase in SPS activity (Laporte et al. 1997; Nguyen-Quoc et al. 1999). These results indicate that the promoter selected to drive transgene expression could play an important role.

There remains a need to determine the metabolism of sucrose in coffee and the enzymes involved in the metabolism. There is also a need to identify and isolate the genes that encode these enzymes in coffee, thereby providing genetic and biochemical tools for modifying sucrose production in coffee beans to manipulate the flavor and aroma of the coffee.

SUMMARY OF THE INVENTION

One aspect of the invention features a nucleic acid molecule isolated from coffee (*Coffea* spp.) comprising a coding sequence that encodes a sucrose synthase, sucrose phosphate synthase or sucrose phosphatase. In one embodiment, the coding sequence encodes a sucrose synthase having an amino acid sequence comprising at least one fragment of SEQ ID NO:8 comprising residues 7-554 or 565-727. In another embodiment, the sucrose synthase has an amino acid sequence greater than 89% identical to SEQ ID NO:8, and preferably comprises SEQ ID NO:8. In other embodiments, the polynucleotide encoding the sucrose synthase has 90% or greater identity to the coding sequence set forth in SEQ ID NO: 1, and preferably comprises SEQ ID NO:1.

In another embodiment, the coding sequence encodes a sucrose phosphate synthase having an amino acid sequence comprising at least one fragment of SEQ ID NO:9 comprising residues 168-439 or 467-644. In another embodiment, the sucrose phosphate synthase has an amino acid sequence greater than 83% identical to SEQ ID NO:9, and preferably comprises SEQ ID NO:9. In other embodiments, the nucleic acid molecule encoding sucrose phosphate synthase has a coding sequence greater than 79% identical to the coding sequence set forth in SEQ ID NO: 2, and preferably comprises SEQ ID NO:2.

In another embodiment, the coding sequence encodes a sucrose phosphatase having an amino acid sequence comprising residues 1-408 of SEQ ID NO:10. In another embodiment, the sucrose phosphatase has an amino acid sequence greater than 81% identical to SEQ ID NO:10, and preferably comprises SEQ ID NO:10. In another embodiment, the nucleic acid molecule comprises a coding sequence greater than 78% identical to the coding sequence set forth in SEQ ID NO:3, and preferably comprises SEQ ID NO:3.

In certain embodiments, the coding sequence of the nucleic acid molecule is an open reading frame of a gene. In other embodiments, it is a mRNA molecule produced by transcription of the gene, or a cDNA molecule produced by reverse transcription of the mRNA molecule.

Another aspect of the invention features an oligonucleotide between 8 and 100 bases in length, which is complementary to a segment of one of the aforementioned nucleic acid molecules.

Another aspect of the invention features a vector comprising the coding sequence of the nucleic acid molecule described above. In some embodiments, the vector is an expression vector selected from the group of vectors consisting of plasmid, phagemid, cosmid, baculovirus, bacmid, bacterial, yeast and viral vectors. In one embodiment, the coding sequence of the nucleic acid molecule is operably linked to a constitutive promoter. In another embodiment, the coding sequence of the nucleic acid molecule is operably linked to an inducible promoter. In another embodiment, the coding sequence of the nucleic acid molecule is operably linked to a tissue specific promoter, particularly a seed specific promoter, and more specifically a coffee seed specific promoter.

Another aspect of the invention features a host cell transformed with the vector described above. In various embodiments, the host cell is a plant cell, bacterial cell, fungal cell, insect cell or mammalian cell. In specific embodiments, the host cell is a plant cell from a plant such as coffee, tobacco, *Arabidopsis*, maize, wheat, rice, soybean barley, rye, oats, sorghum, alfalfa, clover, canola, safflower, sunflower, peanut, cacao, tomatillo, potato, pepper, eggplant, sugar beet, carrot, cucumber, lettuce, pea, aster, begonia, cluysanthemum, delphinium, zinnia, or turfgrasses.

In accordance with another aspect of the invention, a fertile plant produced from the aforementioned transformed plant cell is provided.

Yet another aspect of the invention provides a method of modulating flavor or aroma of coffee beans, comprising modulating production or activity of one or more sucrose metabolizing enzymes within coffee seeds. In one embodiment, the modulating comprises increasing production or activity of the one or more sucrose metabolizing enzymes. This may be accomplished increasing expression of one or more endogenous sucrose metabolizing enzyme-encoding genes within the coffee seeds, which, in certain embodiments, is achieved by introducing a sucrose metabolizing enzyme-encoding transgene into the plant. In one embodiment, the transgene encodes sucrose phosphate synthase. In a particular embodiment, the plant comprises more sucrose in its seeds than does an equivalent plant that does not contain the transgene. In another embodiment, the sucrose metabolizing enzyme is sucrose phosphate synthase and is modified by removal of one or more phosphorylation sites, thereby increasing activity of the enzyme.

In another embodiment, the method of modulation comprises decreasing production or activity of the one or more sucrose metabolizing enzymes. In certain embodiments, this may be accomplished by introducing a nucleic acid molecule into the coffee that inhibits the expression of one or more of the sucrose metabolizing enzyme-encoding genes.

Other features and advantages of the present invention will be understood by reference to the drawings, detailed description and examples that follow.

BRIEF DESCRIPTION OF THE DRAWINGS

FIG. 2. Protein sequence alignment of CcSS2 with other SuSy proteins sequences. CcSS2 protein is aligned with other sucrose synthase proteins available in the NCBI database was done using the CLUSTAL W program in the MegAlign software (Lasergene package, DNASTAR). Amino acids underlined in red are different from CcSS2 protein. GenBank accession numbers are AY205084 for potato SuSyST2 (*Solanum tuberosum*) (SEQ ID NO.:11), AJ537575 for potato SuSyST4 (SEQ ID NO.:12) and AJ011535 for tomato SuSyLE2 (*Lycopersicon esculentum*) (SEQ ID NO.:13).

FIG. 4. Protein sequence alignment of CcSPS1 with other SPS proteins. Alignment of protein encoded by the CcSPS1 cDNA with other SPS proteins available in the NCBI database was done using the CLUSTAL W program in the MegAlign software (Lasergene package, DNASTAR). Amino acids marked in red are different from the CcSPS1 protein. The other SPS proteins, with the associated accession number in parentheses, are as follows: SPSST (*Solanum tuberosum*, CAA51872) (SEQ ID NO.:15), SPSLE1 (*Lycopersicon esculentum*, AAC24872) (SEQ ID NO.:14), SPSNT (*Nicotiana tabacum*, AAF06792) (SEQ ID NO.:16), SPSLE2 (*Lycopersicon esculentum*, AAU29197) (SEQ ID NO.:17). The three sites for potential seryl phosphorylation of CcSPS1 protein are indicated by an asterisk (Ser150, Ser221 and Ser415). A highly conserved sequence surrounding each serine is also shown.

FIG. 5. Protein sequence alignment of CcSP1 with other SP proteins. Alignment of CcSP1 protein with other SP proteins available in the NCBI database was done using the CLUSTAL W program in the MegAlign software (Lasergene package, DNASTAR). Amino acids underlined in red are different from CcSP1 protein. GenBank accession numbers are NP_973609 for *Arabidopsis* SPAT1 (*Arabidopsis thaliana*) (SEQ ID NO.:18) and AAO33160 for tomato SPLE (*Lycopersicon esculentum*) (SEQ ID NO.:19).

DETAILED DESCRIPTION OF ILLUSTRATIVE EMBODIMENTS

Definitions

Figure 1:
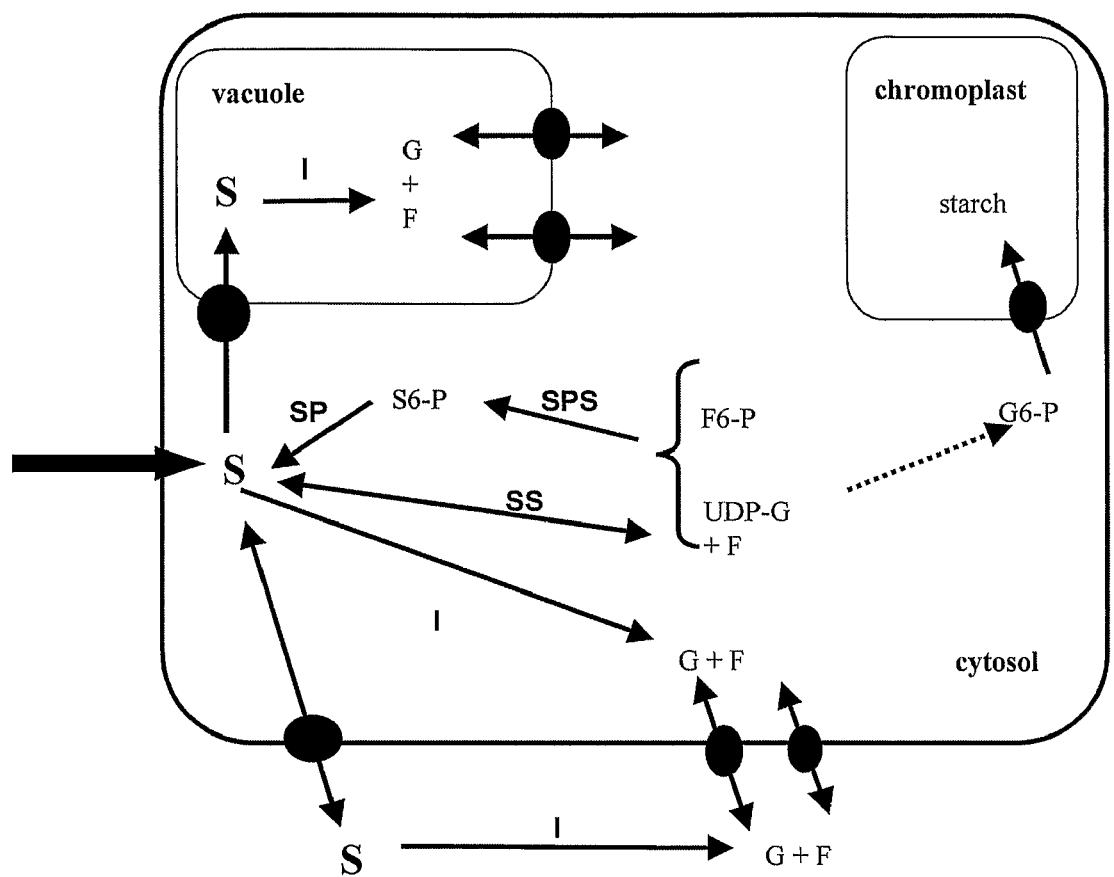
FIG. 1. Model for sucrose metabolism in tomato fruit. Sucrose (S) is imported from phloem by a symplastic pathway or is hydrolyzed by cell-wall invertase. Glucose and fructose are imported into the cytosol by specific Sugar Transporter Proteins. In cytosol, sucrose is degraded by sucrose synthase (SS) and its re-synthesis is catalysed by sucrose phosphate synthase (SPS) associated with sucrose phosphatase (SP) or SS. Sucrose can be exported in vacuole and hydrolysed by vacuolar invertase. UDP-glucose after modifications can be used for starch synthesis in chromoplast. Abbreviations: G, glucose; F, fructose; F6-P, fructose 6-phosphate; UDP-G, UDP-glucose; G6-P, glucose 6-phosphate; S6-P, sucrose 6-phosphate; I, invertase; SP, sucrose phosphatase; SPS sucrose phosphate synthase.

Various terms relating to the biological molecules and other aspects of the present invention are used through the specification and claims. The terms are presumed to have their customary meaning in the field of molecular biology and biochemistry unless they are specifically defined otherwise herein.

The term "sucrose metabolizing enzyme" refers to enzymes in plants that primarily function to accumulate sucrose or degrade sucrose within the plant and include, for example, sucrose synthase (SuSy), sucrose phosphate synthase (SPS) and sucrose phosphatase (SP). Together, the different sucrose metabolizing enzymes operate to control the metabolism of sucrose as needed by the plant for either storage or for energy needs.

"Isolated" means altered "by the hand of man" from the natural state. If a composition or substance occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated", as the term is employed herein.

"Polynucleotide", also referred to as "nucleic acid molecule", generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from natural posttranslational processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins—Structure and Molecular Properties, 2nd Ed., T. E. Creighton, W. H. Freeman and Company, New York, 1993 and Wold, F., Posttranslational Protein Modifications: Perspectives and Prospects, pgs. 1-12 in Posttranslational Covalent Modification of Proteins, B. C. Johnson, Ed., Academic Press, New York, 1983; Seifter et al., "Analysis for Protein Modifications and Nonprotein Cofactors", Meth Enzymol (1990) 182:626-646 and Rattan et al., "Protein Synthesis: Posttranslational Modifications and Aging", Ann NY Acad Sci (1992) 663:48-62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, or deletions in any combination. A substituted or inserted amino acid residue may or may not be one encoded by the genetic code. A variant of a polynucleotide or polypeptide may be naturally occurring, such as an allelic variant, or it may be a variant that is not known to occur naturally. Non-naturally occurring variants of polynucleotides and polypeptides may be made by mutagenesis techniques or by direct synthesis.

In reference to mutant plants, the terms "null mutant" or "loss-of-function mutant" are used to designate an organism or genomic DNA sequence with a mutation that causes a gene product to be non-functional or largely absent. Such mutations may occur in the coding and/or regulatory regions of the gene, and may be changes of individual residues, or insertions or deletions of regions of nucleic acids. These mutations may also occur in the coding and/or regulatory regions of other genes which may regulate or control a gene and/or encoded protein, so as to cause the protein to be non-functional or largely absent.

The term "substantially the same" refers to nucleic acid or amino acid sequences having sequence variations that do not materially affect the nature of the protein (i.e. the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "identity" or "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, J. Theor. Biol. 119:205). When referring to nucleic acid molecules, "percent identical" refers to the percent of the nucleotides of the subject nucleic acid sequence that have been matched to identical nucleotides by a sequence analysis program.

"Identity" and "similarity" can be readily calculated by known methods. Nucleic acid sequences and amino acid sequences can be compared using computer programs that align the similar sequences of the nucleic or amino acids and thus define the differences. In preferred methodologies, the BLAST programs (NCBI) and parameters used therein are employed, and the DNAstar system (Madison, Wis.) is used to align sequence fragments of genomic DNA sequences. However, equivalent alignments and similarity/identity assessments can be obtained through the use of any standard alignment software. For instance, the GCG Wisconsin Package version 9.1, available from the Genetics Computer Group in Madison, Wis., and the default parameters used (gap creation penalty=12, gap extension penalty=4) by that program may also be used to compare sequence identity and similarity.

"Antibodies" as used herein includes polyclonal and monoclonal antibodies, chimeric, single chain, and humanized antibodies, as well as antibody fragments (e.g., Fab, Fab', $F(ab')_2$ and $F_v$), including the products of a Fab or other immunoglobulin expression library. With respect to antibodies, the term, "immunologically specific" or "specific" refers to antibodies that bind to one or more epitopes of a protein of interest, but which do not substantially recognize and bind other molecules in a sample containing a mixed population of antigenic biological molecules. Screening assays to determine binding specificity of an antibody are well known and routinely practiced in the art. For a comprehensive discussion of such assays, see Harlow et al. (Eds.), ANTIBODIES A LABORATORY MAnnual; Cold Spring Harbor Laboratory; Cold Spring Harbor, N.Y. (1988), Chapter 6.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, the compound of interest. Purity is measured by methods appropriate for the compound of interest (e.g. chromatographic methods, agarose or polyacrylamide gel electrophoresis, HPLC analysis, and the like).

With respect to single-stranded nucleic acid molecules, the term "specifically hybridizing" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

A "coding sequence" or "coding region" refers to a nucleic acid molecule having sequence information necessary to produce a gene product, when the sequence is expressed. The coding sequence may comprise untranslated sequences (e.g., introns) within translated regions, or may lack such intervening untranslated sequences (e.g., as in cDNA).

"Intron" refers to polynucleotide sequences in a nucleic acid that do not code information related to protein synthesis. Such sequences are transcribed into mRNA, but are removed before translation of the mRNA into a protein.

The term "operably linked" or "operably inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences can be operably linked to promoters or regulatory sequences in a sense or antisense orientation. The term "operably linked" is sometimes applied to the arrangement of other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA" or "transgene". Such a nucleic acid construct may contain a coding sequence for a gene product of interest, along with a selectable marker gene and/or a reporter gene.

A "marker gene" or "selectable marker gene" is a gene whose encoded gene product confers a feature that enables a cell containing the gene to be selected from among cells not containing the gene. Vectors used for genetic engineering typically contain one or more selectable marker genes. Types of selectable marker genes include (1) antibiotic resistance genes, (2) herbicide tolerance or resistance genes, and (3) metabolic or auxotrophic marker genes that enable transformed cells to synthesize an essential component, usually an amino acid, which the cells cannot otherwise produce.

A "reporter gene" is also a type of marker gene. It typically encodes a gene product that is assayable or detectable by standard laboratory means (e.g., enzymatic activity, fluorescence).

The term "express," "expressed," or "expression" of a gene refers to the biosynthesis of a gene product. The process involves transcription of the gene into mRNA and then translation of the mRNA into one or more polypeptides, and encompasses all naturally occurring post-translational modifications.

"Endogenous" refers to any constituent, for example, a gene or nucleic acid, or polypeptide, that can be found naturally within the specified organism.

A "heterologous" region of a nucleic acid construct is an identifiable segment (or segments) of the nucleic acid molecule within a larger molecule that is not found in association with the larger molecule in nature. Thus, when the heterologous region comprises a gene, the gene will usually be flanked by DNA that does not flank the genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. The term "DNA construct", as defined above, is also used to refer to a heterologous region, particularly one constructed for use in transformation of a cell.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

"Grain," "seed," or "bean," refers to a flowering plant's unit of reproduction, capable of developing into another such plant. As used herein, especially with respect to coffee plants, the terms are used synonymously and interchangeably.

As used herein, the term "plant" includes reference to whole plants, plant organs (e.g., leaves, stems, shoots, roots), seeds, pollen, plant cells, plant cell organelles, and progeny thereof. Parts of transgenic plants are to be understood within the scope of the invention to comprise, for example, plant cells, protoplasts, tissues, callus, embryos as well as flowers, stems, seeds, pollen, fruits, leaves, or roots originating in transgenic plants or their progeny.

Description:

Sucrose is a major contributor of free reducing sugars involved in the Maillard reaction that occurs during the roasting of coffee grain. Therefore, it is widely believed to be an important flavor precursor molecule in the green coffee grain. Consistent with this idea, the highest quality Arabica grains have appreciably higher levels of sucrose (between 7.3 and 11.4%) than the lowest quality Robusta grains (between 4 and 5%). Also, sucrose, while being significantly degraded during roasting, can remain in the roasted grain at concentrations of 0.4-2.8% dry weight (DW) and so participates directly in coffee's sweetness. Because of the clear correlation between the level of sucrose in the grain and coffee flavor, the ability to understand and manipulate the underlying genetic basis for variations in sucrose metabolism and carbon partitioning in coffee grain is important.

Key enzymes involved in sucrose metabolism have been characterized in model organisms (e.g., tomato, potato, *Arabidopsis*). In accordance with the present invention, protein sequences of these enzymes have been used to perform similarity searches in *Coffea canephora* cDNA libraries and EST databases using the tBLASTn algorithm, as described in greater detail in the examples. cDNA encoding sucrose synthase (CcSS2) (SEQ ID NO:1), sucrose phosphate synthase (CcSPS1) (SEQ ID NO:2), sucrose phosphatase (CcSP1) (SEQ ID NO:3) were identified and characterized in *C. canephora*. A partial cDNA sequence of CcSPS1 has also been identified, and is referred to herein as SEQ ID NO:7.

Using degenerate primers, a partial genomic clone of a sucrose phosphate synthase CcSPS1-encoding gene (SEQ ID NO:4) has been isolated from *C. canephora*. A second gene was also isolated, and referred to herein as CcSPS2 (SEQ ID NO:5). Confirmation of expression was performed with CcSPS1 by sequencing the single PCR fragment obtained after RT-PCR. A complete genomic clone of a CcSPS1-encoding gene was identified and is referred to herein as SEQ ID NO:6.

Eleven single nucleotide polymorphisms (SNPs) have been identified in the CcSPS1 full length genomic clone. It is expected that these SNPs and other sequence markers will be useful for placing the CcSPS1 gene on a *C. canephora* genetic map.

The study of SuSy and SPS activity during grain development in a variety of Arabica (*C. Arabica* CCCA12) and Robusta (*C. canephora* FRT05) grain has shown that, although the Robusta variety was characterized by a stronger sink strength (correlated to higher SuSy activity), the Arabica variety accumulated 30% more sucrose in mature beans than did the Robusta variety. Additionally, while SPS activity fluctuated during the Robusta grain development, the SPS activity in Arabica rose rapidly and remained high up to grain maturity. It was found that CcSS2 and CcSPS1 mRNA accumulation was highly correlated with enzymatic activity. The data obtained in accordance with the invention described herein strongly indicate that SPS activity is the limiting step for re-synthesis of sucrose during final step of coffee grain maturation. In the perspective of improving the quality of Robusta and other coffee grain, selection of varieties with high SPS activity, or manipulation of plants to increase SPS production or activity, are expected to be an important route for increasing the final sucrose concentration in mature coffee bean.

Thus, one aspect of the present invention relates to nucleic acid molecules from coffee that encode a number of sucrose metabolizing enzymes, including sucrose synthase (SuSy), exemplified by SEQ ID NO:1, sucrose phosphate synthase (SPS), exemplified by SEQ ID NO:2 (and the partial sequence of SEQ ID NO:7), and the open reading frame of SEQ ID NO:6 (and by the partial open reading frames of SEQ ID NOS: 4 and 5 described herein), and, sucrose phosphatase (SP), exemplified by SEQ ID NO:3. Other aspects of the invention relate to the proteins produced by expression of these nucleic acid molecules and their uses. The deduced amino acid sequences of the proteins produced by expression of SEQ ID NOS: 1, 2 or 3 are set forth herein as SEQ NO:8 (SuSy), SEQ ID NO:9 (SPS) and SEQ ID NO:10 (SP). The predicted molecular masses of these proteins are 92.6 kDa (SuSy), 117 kDa (SPS) and 46.7 kDa (SP). Still other aspects of the invention relate to uses of the nucleic acid molecules and encoded polypeptides in plant breeding and in genetic manipulation of plants, and ultimately in the manipulation of coffee flavor, aroma and other qualities.

Although polynucleotides encoding sucrose metabolizing enzymes from *Coffea canephora* are described and exemplified herein, this invention is intended to encompass nucleic acids and encoded proteins from other *Coffea* species that are sufficiently similar to be used interchangeably with the *C. canephora* polynucleotides and proteins for the purposes described below. Accordingly, when the terms "sucrose synthase," "sucrose phosphate synthase," and "sucrose phosphatase" are used herein, they are intended to encompass all *Coffea* sucrose synthases, sucrose phosphate synthases, and sucrose phosphatases having the general physical, biochemical and functional features described herein, and polynucleotides encoding them.

Considered in terms of their sequences, sucrose metabolizing enzyme-encoding polynucleotides of the invention include allelic variants and natural mutants of any of SEQ ID NOS: 1-7, which are likely to be found in different varieties of *C. canephora*, and homologs of SEQ ID NOS: 1-7 likely to be found in different coffee species. Because such variants and homologs are expected to possess certain differences in nucleotide and amino acid sequence, this invention provides isolated sucrose metabolizing enzyme-encoding nucleic acid molecules that encode respective polypeptides having at least about 80% (and, with increasing order of preference, 81%, 82%, 83%, 84%, 85%, 86%, 87%, 88%, 89%, 90%, 91%, 92%, 93%, 94%, 95%, 96%, 97%, 98% and 99%) identity with the coding regions of any one of SEQ ID NOS: 8-10 and comprises a nucleotide sequence having equivalent ranges of identity to the pertinent portions of any one of SEQ ID NOS: 1-7, respectively. Because of the natural sequence variation likely to exist among sucrose metabolizing enzymes, and the genes encoding them in different coffee varieties and species, one skilled in the art would expect to find this level of variation, while still maintaining the unique properties of the polypeptides and polynucleotides of the present invention. Such an expectation is due in part to the degeneracy of the genetic code, as well as to the known evolutionary success of conservative amino acid sequence variations, which do not appreciably alter the nature of the encoded protein. Accordingly, such variants and homologs are considered substantially the same as one another and are included within the scope of the present invention.

The following sections set forth the general procedures involved in practicing the present invention. To the extent that specific materials are mentioned, it is merely for the purpose of illustration, and is not intended to limit the invention. Unless otherwise specified, general biochemical and molecular biological procedures, such as those set forth in Sambrook et al., Molecular Cloning, Cold Spring Harbor Laboratory (1989) or Ausubel et al. (eds), Current Protocols in Molecular Biology, John Wiley & Sons (2005) are used.

Nucleic Acid Molecules, Proteins and Antibodies:

Nucleic acid molecules of the invention may be prepared by two general methods: (1) they may be synthesized from appropriate nucleotide triphosphates, or (2) they may be isolated from biological sources. Both methods utilize protocols well known in the art.

The availability of nucleotide sequence information, such as the cDNA having SEQ ID NOS: 1, 2 or 3, (or the open reading frame of SEQ ID NO:6) enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

In accordance with the present invention, nucleic acids having the appropriate level sequence homology with part or all of the coding and/or regulatory regions of sucrose metabolizing enzyme-encoding polynucleotides may be identified by using hybridization and washing conditions of appropriate stringency. It will be appreciated by those skilled in the art that the aforementioned strategy, when applied to genomic sequences, will, in addition to enabling isolation of sucrose metabolizing enzyme-coding sequences, also enable isolation of promoters and other gene regulatory sequences associated with sucrose metabolizing enzyme genes, even though the regulatory sequences themselves may not share sufficient homology to enable suitable hybridization.

As a typical illustration, hybridizations may be performed, according to the method of Sambrook et al., using a hybridization solution comprising: 5×SSC, 5× Denhardt's reagent, 1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 2×SSC and 0.1% SDS; (4) 2 hours at 45-55° C. in 2×SSC and 0.1% SDS, changing the solution every 30 minutes.

One common formula for calculating the stringency conditions required to achieve hybridization between nucleic acid molecules of a specified sequence homology (Sambrook et al., 1989):

$$Tm=81.5° C.+16.6 \text{ Log } [Na+]+0.41(\% G+C)-0.63(\% \text{ formamide})-600/\#bp \text{ in duplex}$$

As an illustration of the above formula, using [Na+]=[0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C. In one embodiment, the hybridization is at 37° C. and the final wash is at 42° C.; in another embodiment the hybridization is at 42° C. and the final wash is at 50° C.; and in yet another embodiment the hybridization is at 42° C. and final wash is at 65° C., with the above hybridization and wash solutions. Conditions of high stringency include hybridization at 42° C. in the above hybridization solution and a final wash at 65° C. in 0.1×SSC and 0.1% SDS for 10 minutes.

Nucleic acids of the present invention may be maintained as DNA in any convenient cloning vector. In a preferred embodiment, clones are maintained in plasmid cloning/expression vector, such as pGEM-T (Promega Biotech, Madison, Wis.), pBluescript (Stratagene, La Jolla, Calif.), pCR4-TOPO (Invitrogen, Carlsbad, Calif.) or pET28a+ (Novagen, Madison, Wis.), all of which can be propagated in a suitable E. coli host cell.

Nucleic acid molecules of the invention include cDNA, genomic DNA, RNA, and fragments thereof which may be single-, double-, or even triple-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting sucrose metabolizing enzyme encoding genes or mRNA in test samples of plant tissue, e.g., by PCR amplification, or for the positive or negative regulation of expression of sucrose metabolizing enzyme-encoding genes at or before translation of the mRNA into proteins. Methods in which sucrose metabolizing enzyme-encoding oligonucleotides or polynucleotides may be utilized as probes for such assays include, but are not limited to: (1) in situ hybridization; (2) Southern hybridization (3) northern hybridization; and (4) assorted amplification reactions such as polymerase chain reactions (PCR, including RT-PCR) and ligase chain reaction (LCR).

Polypeptides encoded by nucleic acids of the invention may be prepared in a variety of ways, according to known methods. If produced in situ the polypeptides may be purified from appropriate sources, e.g., seeds, pericarps, or other plant parts.

Alternatively, the availability of isolated nucleic acid molecules encoding the SuSy, SPS or SP polypeptides enables production of the proteins using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis., BRL, Rockville, Md. or Invitrogen, Carlsbad, Calif.

According to a preferred embodiment, larger quantities of sucrose metabolizing enzymes may be produced by expression in a suitable procaryotic or eucaryotic system. For example, part or all of a DNA molecule, such as the cDNAs having SEQ ID NOS: 1, 2 or 3, may be inserted into a plasmid vector adapted for expression in a bacterial cell (such as *E. coli*) or a yeast cell (such as *Saccharomyces cerevisiae*), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The sucrose metabolizing enzymes produced by gene expression in a recombinant procaryotic or eucaryotic system may be purified according to methods known in the art. In a preferred embodiment, a commercially available expression/secretion system can be used, whereby the recombinant protein is expressed and thereafter secreted from the host cell, and, thereafter, purified from the surrounding medium. An alternative approach involves purifying the recombinant protein by affinity separation, e.g., via immunological interaction with antibodies that bind specifically to the recombinant protein.

The sucrose metabolizing enzymes of the invention, prepared by the aforementioned methods, may be analyzed according to standard procedures.

Sucrose metabolizing enzymes purified from coffee or recombinantly produced, may be used to generate polyclonal or monoclonal antibodies, antibody fragments or derivatives as defined herein, according to known methods. In addition to making antibodies to the entire recombinant protein, if analyses of the proteins or Southern and cloning analyses (see below) indicate that the cloned genes belongs to a multigene family, then member-specific antibodies made to synthetic peptides corresponding to nonconserved regions of the protein can be generated.

Kits comprising an antibody of the invention for any of the purposes described herein are also included within the scope of the invention. In general, such a kit includes a control antigen for which the antibody is immunospecific.

Vectors, Cells, Tissues and Plants:

Also featured in accordance with the present invention are vectors and kits for producing transgenic host cells that contain a sucrose metabolizing enzyme-encoding polynucleotide or oligonucleotide, or homolog, analog or variant thereof in a sense or antisense orientation, or reporter gene and other constructs under control of sucrose metabolizing enzyme-promoters and other regulatory sequences. Suitable host cells include, but are not limited to, plant cells, bacterial cells, yeast and other fungal cells, insect cells and mammalian cells. Vectors for transforming a wide variety of these host cells are well known to those of skill in the art. They include, but are not limited to, plasmids, cosmids, baculoviruses, bacmids, bacterial artificial chromosomes (BACs), yeast artificial chromosomes (YACs), as well as other bacterial, yeast and viral vectors. Typically, kits for producing transgenic host cells will contain one or more appropriate vectors and instructions for producing the transgenic cells using the vector. Kits may further include one or more additional components, such as culture media for culturing the cells, reagents for performing transformation of the cells and reagents for testing the transgenic cells for gene expression, to name a few.

The present invention includes transgenic plants comprising one or more copies of a sucrose metabolizing enzyme-encoding gene, or nucleic acid sequences that inhibit the production or function of a plant's endogenous sucrose metabolizing enzymes. This is accomplished by transforming plant cells with a transgene that comprises part of all of a sucrose metabolizing enzyme coding sequence, or mutant, antisense or variant thereof, including RNA, controlled by either native or recombinant regulatory sequences, as described below. Transgenic plants coffee species are preferred, including, without limitation, *C. abeokutae, C. arabica, C. arnoldiana, C. aruwemiensis, C. bengalensis, C. canephora, C. congensis C. dewevrei, C. excelsa, C. eugenioides*, and *C. heterocalyx, C. kapakata, C. khasiana, C. liberica, C. moloundou, C. rasemosa, C. salvatrix, C. sessiflora, C. stenophylla, C. travencorensis, C. wightiana* and *C. zanguebariae*. Plants of any species are also included in the invention; these include, but are not limited to, tobacco, *Arabidopsis* and other "laboratory-friendly" species, cereal crops such as maize, wheat, rice, soybean barley, rye, oats, sorghum, alfalfa, clover and the like, oil-producing plants such as canola, safflower, sunflower, peanut, cacao and the like, vegetable crops such as tomato tomatillo, potato, pepper, eggplant, sugar beet, carrot, cucumber, lettuce, pea and the like, horticultural plants such as aster, begonia, chrysanthemum, delphinium, petunia, zinnia, lawn and turfgrasses and the like.

Transgenic plants can be generated using standard plant transformation methods known to those skilled in the art. These include, but are not limited to, *Agrobacterium* vectors, polyethylene glycol treatment of protoplasts, biolistic DNA delivery, UV laser microbeam, gemini virus vectors or other plant viral vectors, calcium phosphate treatment of protoplasts, electroporation of isolated protoplasts, agitation of cell suspensions in solution with microbeads coated with the transforming DNA, agitation of cell suspension in solution with silicon fibers coated with transforming DNA, direct DNA uptake, liposome-mediated DNA uptake, and the like. Such methods have been published in the art. See, e.g., Methods for Plant Molecular Biology (Weissbach & Weissbach, eds., 1988); Methods in Plant Molecular Biology (Schuler & Zielinski, eds., 1989); Plant Molecular Biology Manual (Gelvin, Schilperoort, Verma, eds., 1993); and Methods in Plant Molecular Biology—A Laboratory Manual (Maliga, Klessig, Cashmore, Gruissem & Varner, eds., 1994).

The method of transformation depends upon the plant to be transformed. *Agrobacterium* vectors are often used to transform dicot species. *Agrobacterium* binary vectors include, but are not limited to, BIN19 and derivatives thereof, the pBI vector series, and binary vectors pGA482, pGA492, pLH7000 (GenBank Accession AY234330) and any suitable one of the pCAMBIA vectors (derived from the pPZP vectors constructed by Hajdukiewicz, Svab & Maliga, (1994) Plant Mol Biol 25: 989-994, available from CAMBIA, GPO Box 3200, Canberra ACT 2601, Australia or via the worldwide web at CAMBIA.org). For transformation of monocot species, biolistic bombardment with particles coated with transforming DNA and silicon fibers coated with transforming DNA are often useful for nuclear transformation. Alternatively, *Agrobacterium* "superbinary" vectors have been used successfully for the transformation of rice, maize and various other monocot species.

DNA constructs for transforming a selected plant comprise a coding sequence of interest operably linked to appropriate 5' regulatory sequences (e.g., promoters and translational regulatory sequences) and 3' regulatory sequences (e.g., terminators). In a preferred embodiment, a sucrose metabolizing enzyme-encoding sequence under control of its natural 5' and 3' regulatory elements is utilized. In other embodiments, sucrose metabolizing enzyme-encoding and regulatory sequences are swapped to alter the sugar profile of the transformed plant for a phenotypic improvement, e.g., in flavor, aroma or other feature.

In an alternative embodiment, the coding region of the gene is placed under a powerful constitutive promoter, such as the Cauliflower Mosaic Virus (CaMV) 35S promoter or the figwort mosaic virus 35S promoter. Other constitutive promoters contemplated for use in the present invention include, but are not limited to: T-DNA mannopine synthetase, nopaline synthase and octopine synthase promoters. In other embodiments, a strong monocot promoter is used, for example, the maize ubiquitin promoter, the rice actin promoter or the rice tubulin promoter (Jeon et al., Plant Physiology. 123: 1005-14, 2000).

Transgenic plants expressing sucrose metabolizing enzyme-coding sequences under an inducible promoter are also contemplated to be within the scope of the present invention. Inducible plant promoters include the tetracycline repressor/operator controlled promoter, the heat shock gene promoters, stress (e.g., wounding)-induced promoters, defense responsive gene promoters (e.g. phenylalanine ammonia lyase genes), wound induced gene promoters (e.g. hydroxyproline rich cell wall protein genes), chemically-inducible gene promoters (e.g., nitrate reductase genes, glucanase genes, chitinase genes, etc.) and dark-inducible gene promoters (e.g., asparagine synthetase gene) to name a few.

Tissue specific and development-specific promoters are also contemplated for use in the present invention. Non-limiting examples of seed-specific promoters include Cim1 (cytokinin-induced message), cZ19B1 (maize 19 kDa zein), milps (myo-inositol-1-phosphate synthase), and celA (cellulose synthase) (U.S. application Ser. No. 09/377,648), bean beta-phaseolin, napin, beta-conglycinin, soybean lectin, cruciferin, maize 15 kDa zein, 22 kDa zein, 27 kDa zein, g-zein, waxy, shrunken 1, shrunken 2, and globulin 1, soybean 11S legumin (Bäumlein et al., 1992), and C. canephora 11S seed storage protein (Marraccini et al., 1999, Plant Physiol. Biochem. 37:273-282). See also WO 00/12733, where seed-preferred promoters from end1 and end2 genes are disclosed. Other Coffea seed specific promoters may also be utilized, including but not limited to the oleosin gene promoter described in commonly-owned, co-pending Provisional Application No. 60/696,445 and the dehyrdin gene promoter described in commonly-owned, co-pending Provisional Application No. 60/696,890. Examples of other tissue-specific promoters include, but are not limited to: the ribulose bisphosphate carboxylase (RuBisCo) small subunit gene promoters (e.g., the coffee small subunit promoter as described by Marraccini et al., 2003) or chlorophyll a/b binding protein (CAB) gene promoters for expression in photosynthetic tissue; and the root-specific glutamine synthetase gene promoters where expression in roots is desired.

The coding region is also operably linked to an appropriate 3' regulatory sequence. In embodiments where the native 3' regulatory sequence is not use, the nopaline synthetase polyadenylation region may be used. Other useful 3' regulatory regions include, but are not limited to the octopine synthase polyadenylation region.

The selected coding region, under control of appropriate regulatory elements, is operably linked to a nuclear drug resistance marker, such as kanamycin resistance. Other useful selectable marker systems include genes that confer antibiotic or herbicide resistances (e.g., resistance to hygromycin, sulfonylurea, phosphinothricin, or glyphosate) or genes conferring selective growth (e.g., phosphomannose isomerase, enabling growth of plant cells on mannose). Selectable marker genes include, without limitation, genes encoding antibiotic resistance, such as those encoding neomycin phosphotransferase II (NEO), dihydrofolate reductase (DHFR) and hygromycin phosphotransferase (HPT), as well as genes that confer resistance to herbicidal compounds, such as glyphosate-resistant EPSPS and/or glyphosate oxidoreducatase (GOX), Bromoxynil nitrilase (BXN) for resistance to bromoxynil, AHAS genes for resistance to imidazolinones, sulfonylurea resistance genes, and 2,4-dichlorophenoxyacetate (2,4-D) resistance genes.

In certain embodiments, promoters and other expression regulatory sequences encompassed by the present invention are operably linked to reporter genes. Reporter genes contemplated for use in the invention include, but are not limited to, genes encoding green fluorescent protein (GFP), red fluorescent protein (DsRed), Cyan Fluorescent Protein (CFP), Yellow Fluorescent Protein (YFP), Cerianthus Orange Fluorescent Protein (cOFP), alkaline phosphatase (AP), β-lactamase, chloramphenicol acetyltransferase (CAT), adenosine deaminase (ADA), aminoglycoside phosphotransferase (neo$^r$, G418$^r$) dihydrofolate reductase (DHFR), hygromycin-B-phosphotransferase (HPH), thymidine kinase (TK), lacZ (encoding α-galactosidase), and xanthine guanine phosphoribosyltransferase (XGPRT), Beta-Glucuronidase (gus), Placental Alkaline Phosphatase (PLAP), Secreted Embryonic Alkaline Phosphatase (SEAP), or Firefly or Bacterial Luciferase (LUC). As with many of the standard procedures associated with the practice of the invention, skilled artisans will be aware of additional sequences that can serve the function of a marker or reporter.

Additional sequence modifications are known in the art to enhance gene expression in a cellular host. These modifications include elimination of sequences encoding superfluous polyadenylation signals, exon-intron splice site signals, transposon-like repeats, and other such well-characterized sequences that may be deleterious to gene expression. Alternatively, if necessary, the G/C content of the coding sequence may be adjusted to levels average for a given coffee plant cell host, as calculated by reference to known genes expressed in a coffee plant cell. Also, when possible, the coding sequence is modified to avoid predicted hairpin secondary mRNA structures. Another alternative to enhance gene expression is to use 5' leader sequences. Translation leader sequences are well known in the art, and include the cis-acting derivative (omega') of the 5' leader sequence (omega) of the tobacco mosaic virus, the 5' leader sequences from brome mosaic virus, alfalfa mosaic virus, and turnip yellow mosaic virus.

Plants are transformed and thereafter screened for one or more properties, including the presence of the transgene product, the transgene-encoding mRNA, or an altered phenotype associated with expression of the transgene. It should be recognized that the amount of expression, as well as the tissue- and temporal-specific pattern of expression of the transgenes in transformed plants can vary depending on the position of their insertion into the nuclear genome. Such positional effects are well known in the art. For this reason, several nuclear transformants should be regenerated and tested for expression of the transgene.

Methods:

The nucleic acids and polypeptides of the present invention can be used in any one of a number of methods whereby the protein products can be expressed in coffee plants in order that the proteins may play a role in the enhancement of the flavor and/or aroma of the coffee beverage or coffee products ultimately produced from the bean of the coffee plant expressing the protein.

There is a strong correlation between the sucrose concentration in green beans and high quality coffee (Russwurm, 1969; Holscher and Steinhart, 1995; Badoud, 2000; Illy and Viani, 1995; Leloup et al., 2003). Improvement of coffee grain sucrose content can be obtained by (1) classical breeding or (2) genetic engineering techniques, and by combining these two approaches. Both approaches have been considerably improved by the isolation and characterization of sucrose metabolism-related genes in coffee, in accordance with the present invention. For example, the sucrose metabolism enzyme-encoding genes may be genetically mapped and Quantitative Trait Loci (QTL) involved in coffee flavor can be identified. It would be then be possible to determine if such QTL correlate with the position of sucrose related genes. It is also possible to identify alleles (haplotypes), for genes affecting sucrose metabolism and examine if the presence of specific haplotypes are strongly correlated with high sucrose. These "high sucrose" markers can be used to advantage in marker assisted breeding programs. A third advantage of isolating polynucleotides involved in sucrose metabolism is described in detail in the Examples. It is to generate expression data for the genes during coffee bean maturation in varieties with high and low sucrose levels. This information is used to direct the choice of genes to use in genetic manipulation aimed at generating novel transgenic coffee plants that have increased sucrose levels in the mature bean, as described in detail below.

In one aspect, the present invention features methods to alter the sucrose metabolizing enzyme profile, or sugar profile, in a plant, preferably coffee, comprising increasing or decreasing an amount or activity of one or more sucrose metabolizing enzymes in the plant. For instance, in one embodiment of the invention, a sucrose metabolizing enzyme-encoding gene under control of its own expression-controlling sequences is used to transform a plant for the purpose of increasing production of that sucrose metabolizing enzyme in the plant. Alternatively, a sucrose metabolizing enzyme-encoding region is operably linked to heterologous expression controlling regions, such as constitutive or inducible promoters.

In view of the fact that it has been possible to increase the sucrose levels in the pericarp of tomato by the constitutive over-expression of SPS, one preferred embodiment of the present invention comprises transforming coffee plants with an SPS-encoding polynucleotide, such as SEQ ID NO:2, for the purpose of over-producing that coffee SPS in various tissues of coffee. In one embodiment, coffee plants are engineered for a general increase in SPS activity, e.g., through the use of a promoter such as the RuBisCo small subunit (SSU) promoter or the CaMV35S promoter. In another embodiment designed to limit the effects of over-expressing SPS only to the sink organ of interest, i.e., the grain, a grain-specific promoter may be utilized, particularly one of the *Coffea* grain-specific promoters described above.

The sucrose profile of a plant may be enhanced by modulating the production, or activity, of one or more sucrose metabolizing enzymes in the plant, such as coffee. Additionally, plants expressing enhance sucrose levels may be screened for naturally-occurring variants of the sucrose metabolizing enzymes. For instance, loss-of-function (null) mutant plants may be created or selected from populations of plant mutants currently available. It will also be appreciated by those of skill in the art that mutant plant populations may also be screened for mutants that over-express a particular sucrose metabolizing enzyme, utilizing one or more of the methods described herein. Mutant populations can be made by chemical mutagenesis, radiation mutagenesis, and transposon or T-DNA insertions, or targeting induced local lesions in genomes (TILLING, see, e.g., Henikoff et al., 2004, Plant Physiol. 135(2): 630-636; Gilchrist & Haughn, 2005, Curr. Opin. Plant Biol. 8(2): 211-215). The methods to make mutant populations are well known in the art.

Of particular interest are mutants of sucrose metabolizing enzymes that have select mutations that alter the post-translational modification of the enzyme, which may affect the enzymatic activity or substrate specificity of the enzyme. Post-translational modification is understood in the art to include a number of modifications to a protein that occurs in eukaryotic cells after translation of the protein and can include, among others, glycosylation, alkylation, and phosphorylation of the protein. In some examples, the sucrose metabolizing enzyme SPS, which has been found to have potential phosphorylation sites at Ser150, Ser221 and Ser415, may have phosphorylation sites removed by the introduction of point-mutations at any one or a combination of the potential phosphorylation sites. Through these point-mutations, the phosphorylation pattern of the enzyme can be modified, thus modifying the activity of the enzyme. Ser150 is thought to be a regulation site for the enzyme SPS; thus, by removing this phosphorylation site by site-directed mutagenesis, the activity of SPS may be enhanced. Additionally, Ser415 is thought to have an antagonizing relationship to the regulatory effect of phosphorylation of Ser150; therefore, removal of this phosphorylation site (Ser415) could further regulate the activity of SPS. Further, phosphorylation at Ser221 of SPS is thought to also inhibit the activity of SPS. Removal of this phosphorylation site (Ser221) could also enhance the activity of SPS.

The nucleic acids of the invention can be used to identify mutant forms of sucrose metabolizing enzymes in various plant species. In species such as maize or *Arabidopsis*, where transposon insertion lines are available, oligonucleotide primers can be designed to screen lines for insertions in the sucrose metabolizing enzyme genes. Through breeding, a plant line may then be developed that is heterozygous or homozygous for the interrupted gene.

A plant also may be engineered to display a phenotype similar to that seen in null mutants created by mutagenic techniques. A transgenic null mutant can be created by a expressing a mutant form of a selected sucrose metabolizing enzyme protein to create a "dominant negative effect." While not limiting the invention to any one mechanism, this mutant protein will compete with wild-type protein for interacting proteins or other cellular factors. Examples of this type of "dominant negative" effect are well known for both insect and vertebrate systems (Radke et al, 1997, Genetics 145: 163-171; Kolch et al., 1991, Nature 349: 426-428).

Another kind of transgenic null mutant can be created by inhibiting the translation of sucrose metabolizing enzyme-encoding mRNA by "post-transcriptional gene silencing." The sucrose metabolizing enzyme-encoding gene from the species targeted for down-regulation, or a fragment thereof, may be utilized to control the production of the encoded protein. Full-length antisense molecules can be used for this purpose. Alternatively, antisense oligonucleotides targeted to specific regions of the mRNA that are critical for translation may be utilized. The use of antisense molecules to decrease expression levels of a pre-determined gene is known in the art. Antisense molecules may be provided in situ by transforming plant cells with a DNA construct which, upon transcription, produces the antisense RNA sequences. Such constructs can be designed to produce full-length or partial antisense sequences. This gene silencing effect can be enhanced by transgenically over-producing both sense and antisense RNA of the gene coding sequence so that a high amount of dsRNA is produced (for example see Waterhouse et al., 1998, PNAS 95: 13959-13964). In this regard, dsRNA containing sequences that correspond to part or all of at least one intron have been found particularly effective. In one embodiment, part or all of the sucrose metabolizing enzyme-encoding sequence antisense strand is expressed by a transgene. In another embodiment, hybridizing sense and antisense strands of part or all of the sucrose metabolizing enzyme-encoding sequence are transgenically expressed.

In another embodiment, sucrose metabolizing enzyme-encoding genes may be silenced through the use of a variety of other post-transcriptional gene silencing (RNA silencing) techniques that are currently available for plant systems. RNA silencing involves the processing of double-stranded RNA (dsRNA) into small 21-28 nucleotide fragments by an RNase H-based enzyme ("Dicer" or "Dicer-like"). The cleavage products, which are siRNA (small interfering RNA) or miRNA (micro-RNA) are incorporated into protein effector complexes that regulate gene expression in a sequence-specific manner (for reviews of RNA silencing in plants, see Horiguchi, 2004, *Differentiation* 72: 65-73; Baulcombe, 2004, Nature 431: 356-363; Herr, 2004, *Biochem. Soc. Trans.* 32: 946-951).

Small interfering RNAs may be chemically synthesized or transcribed and amplified in vitro, and then delivered to the cells. Delivery may be through microinjection (Tuschl T et al., 2002), chemical transfection (Agrawal N et al., 2003), electroporation or cationic liposome-mediated transfection (Brummelkamp T R et al., 2002; Elbashir S M et al., 2002), or any other means available in the art, which will be appreciated by the skilled artisan. Alternatively, the siRNA may be expressed intracellularly by inserting DNA templates for siRNA into the cells of interest, for example, by means of a plasmid, (Tuschl T et al., 2002), and may be specifically targeted to select cells. Small interfering RNAs have been successfully introduced into plants. (Klahre U et al., 2002).

A preferred method of RNA silencing in the present invention is the use of short hairpin RNAs (shRNA). A vector containing a DNA sequence encoding for a particular desired siRNA sequence is delivered into a target cell by any common means. Once in the cell, the DNA sequence is continuously transcribed into RNA molecules that loop back on themselves and form hairpin structures through intramolecular base pairing. These hairpin structures, once processed by the cell, are equivalent to siRNA molecules and are used by the cell to mediate RNA silencing of the desired protein. Various constructs of particular utility for RNA silencing in plants are described by Horiguchi, 2004, supra. Typically, such a construct comprises a promoter, a sequence of the target gene to be silenced in the "sense" orientation, a spacer, the antisense of the target gene sequence, and a terminator.

Yet another type of synthetic null mutant can also be created by the technique of "co-suppression" (Vaucheret et al., 1998, Plant J. 16(6): 651-659). Plant cells are transformed with a copy of the endogenous gene targeted for repression. In many cases, this results in the complete repression of the native gene as well as the transgene. In one embodiment, a sucrose metabolizing enzyme-encoding gene from the plant species of interest is isolated and used to transform cells of that same species.

Mutant or transgenic plants produced by any of the foregoing methods are also featured in accordance with the present invention. Preferably, the plants are fertile, thereby being useful for breeding purposes. Thus, mutant or plants that exhibit one or more of the aforementioned desirable phenotypes can be used for plant breeding, or directly in agricultural or horticultural applications. They will also be of utility as research tools for the further elucidation of the participation of sucrose metabolizing enzymes and its affects on sucrose levels, thereby affecting the flavor, aroma and other features of coffee seeds. Plants containing one transgene or a specified mutation may also be crossed with plants containing a complementary transgene or genotype in order to produce plants with enhanced or combined phenotypes.

The following examples are provided to describe the invention in greater detail. The examples are for illustrative purposes, and are not intended to limit the invention.

EXAMPLE 1

Materials and Methods for Subsequent Examples

Plant Material. Tissues from either leaves, flowers, stem, roots, or cherries were harvested at different stages of development from *Coffea arabica* L. cv. Caturra T-2308 grown under greenhouse conditions (25° C., 70% RH) in Tours, France, and from *Coffea canephora* (robusta) BP-409 grown in the field at the Indonesian Coffee and Cacao Research Center (ICCRI), Indonesia. FRT05 (Robusta) and CCCA12 (Arabica) were obtained from trees cultivated in Centre Quito, Ecuador. The fruit was harvested at defined stages and frozen immediately in liquid nitrogen, and then packaged in dry ice for transport. Tissues were stored at −80° C. until use.

Genomic DNA preparation. Leaves from BP-409 were harvested from greenhouse-grown trees at Tours, France. Tissue was frozen immediately in liquid nitrogen and reduced in fine powder. Genomic DNA was prepared according to Crouzillat et al., 1996.

PCR amplification of partial coffee SPS Gene. Degenerated oligonucleotides SPS-3 (5'ggNcgNgaYtctgaYacNggtgg3') (SEQ ID NO.:20) and SPS-4 (5'tggacgacaYtcNccaaaNgcYttNac3') (SEQ ID NO.:21) were made from the conserved sequence of sucrose-phosphate synthase deduced from the alignment set forth in FIG. 4 and used as primers in PCR amplification. PCR reactions were performed in a 50 µl reaction volume with 100 ng genomic DNA, 0.5 µM of each primer, 200 µM of dNTPs, 1× Taq polymerase buffer and 1 U of TaqDNA polymerase (TAKARA). After a pre-denaturing step at 94° C. for 5 min, the amplification consisted of 30 cycles of 1 min at 94° C., 1 min at 12 different temperatures (from 45° C. to 56° C.) and 2 min at 72° C. The resulting PCR fragments were separated and purified by agarose gel electrophoresis. PCR fragment from the major bands was purified, cloned and sequenced.

Isolation of CcSPS1 and CcSPS2 partial cDNA sequences. In order to verify if CcSPS1 and CcSPS2 genes were expressed, specific primers were designed based on potential coding sequences identified on the partial genomic CcSPS1 and CcSPS2 sequences (SEQ ID NOS: 4 and 5, respectively). Two sets of primers, cDNAC1-1 (5' AACTTGCAAGGGCTTTAGGT3') (SEQ ID NO.:22), cDNAC1-2 (5' AAGGGCTAGTATCATAGGCT3') (SEQ ID NO.:23) and cDNAD1-1 (5' AGCTTGCTAAGGCACTTGCT3') (SEQ ID NO.:24), cDNAD1-2 (5' CAATGCTAGAATCATTGGCT3') (SEQ ID NO.:25) were used to amplify partial CcSPS1 and CcSPS2 cDNA sequences respectively by PCR using various cDNA samples prepared as described below.

Universal Genome Walker. Genomic DNA from BP409 was hydrolyzed with four different restriction enzymes (DraI, EcoRV, PvuI, StuI) and the resulting fragments were ligated blunt-end to the GenomeWalker Adaptor provided by the Universal GenomeWalker kit (BD Biosciences). Both reactions were carried out in accordance with the kit user manual. The four libraries were then employed as templates in PCR reactions using SPS-GSP (gene-specific primers) (Table 1) The reaction mixtures contained 1 µl of GenomeWalker library template, 10 nmol of each dNTP, 50 pmol of each primer and 2.5 units of DNA polymerase in a final volume of 50 µl with the appropriate buffer. The following conditions were used for the first PCR: after pre-denaturing at 95° C. for 2 min, the first seven cycles were performed at a denaturing temperature of 95° C. for 30 s, followed by an annealing and elongation step at 72° C. for 3 min. A further 35 cycles were carried out, changing the annealing/elongation temperature to 67° C. for 3 min. Products from the first amplification using the primer pair AP1/C1-GW (Genome Walker) served as template for the second PCR using AP2/C1-GWN (Genome Walker Nested primer), with AP2 and C1-GWN as primers. The second PCR used 2 µl of the first amplification reaction (undiluted and different dilutions up to 1:50), and was performed as described above for the first reaction, with the exception that the second reaction used only 25 cycles of amplification. The resulting PCR fragments were separated and purified by agarose gel electrophoresis. PCR fragment from the major bands was purified, cloned and sequenced.

Next, 4 µl of first strand buffer (5×, Invitrogen), 2 µl of DTT (0.1 M, Invitrogen) and 1 µl of dNTP mix (10 mM each, Invitrogen) were added. These reaction mixes were preincubated at 42° C. for 2 min before adding 1 µl-SuperScript III Rnase H-Reverse transcriptase (200 U/µl, Invitrogen). Subsequently, the tubes were incubated at 42° C. for 50 min, followed by enzyme inactivation by heating at 70° C. for 10 min. The cDNA samples generated were then diluted one hundred fold and 5 µl of the diluted cDNA were used for Q-PCR.

Full length SPS cDNA amplification. In order to amplify full length CcSPS1 cDNA, two primers:
cDNAC1-am3 (5' ATGGCGGGAAATGACTGGATAAA-CAGTTAC3') (SEQ ID NO.:36) and
cDNAC1-am4 (5' CTAGCTTTTGAGAAC-CCCTAGCTTTTCCAAC3') (SEQ ID NO.:37) have been designed based on the CcSPS1 genomic sequence. These two primers have been used to perform PCR reaction using methods as described above. The single fragment obtained has been purified from agarose gel, cloned and sequenced.

Quantitative-PCR. TaqMan-PCR was carried out as recommended by the manufacturer (Applied Biosystems, Per-

TABLE 1

List of rimers used for GenomeWalker experiments

| Primers | Sequences | Sequence Identifier |
|---|---|---|
| AP1 | 5'gtaatacgactcactatagggc3' | SEQ ID NO.: 26 |
| AP2 | 5'actatagggcacgcgtggt3' | SEQ ID NO.: 27 |
| C1-GW1 | 5'tacttccagtgatgatacctgcctcgta3' | SEQ ID NO.: 28 |
| C1-GWN1 | 5'tctaggaggcagcatctcagtgggt-tca 3' | SEQ ID NO.: 29 |
| C1-GW3 | 5'ccggatccacatatttggggagag-gtct 3' | SEQ ID NO.: 30 |
| C1-GWN3 | 5'tggtgtcatgcagataatgcgc-tacttc 3' | SEQ ID NO.: 31 |
| C1-GW6 | 5'gcaatcgacccctattgctctcac-catgt 3' | SEQ ID NO.: 32 |
| C1-GWN6 | 5'agtcttcagacatatcagcaact-gcttc 3' | SEQ ID NO.: 33 |
| C1-GW7 | 5'gtgagctctctgtggttgatgttgt-tga 3' | SEQ ID NO.: 34 |
| C1-GWN7 | 5'gtttcgaattctggctcaatgcaac-cact 3' | SEQ ID NO.: 35 |

DNA sequence analysis. For DNA sequencing, recombinant plasmid DNA was prepared and sequenced according to standard methods. Computer analysis was performed using DNA Star (Lasergene) software. Sequence homologies were verified against GenBank databases using BLAST programs (Altschul et al. 1990).

cDNA preparation. RNA was extracted from different tissues i.e. root, stem, leaves, flowers, pericarp and grain at four different maturation stages SG (small green), LG (large green), Y (yellow), R (red), as described previously (Benamor and Mc Carthy, 2003). cDNA was prepared from total RNA and oligo dT(18) (Sigma) as follows: 1 µg total RNA sample plus 50 ng oligo dT was made up to 12 µl final volume with DEPC-treated water. This mixture was subsequently incubated at 70° C. for 10 min and then rapidly cooled on ice.

kin-Elmer). All reactions contained 1× TaqMan buffer (Perkin-Elmer) and 5 mM MgCl2, 200 µM each of dATP, dCTP, dGTP and dTTP, and 0.625 units of AmpliTaq Gold polymerase. PCR was carried out using 800 nM of each gene specific primers, forward and reverse, and 200 nM TaqMan probe. Primers and probes were designed using PRIMER EXPRESS software (Applied Biosystems, Table 2). Reaction mixtures were incubated for 2 min at 50° C., 10 min at 95° C., followed by 40 amplification cycles of 15 sec at 95° C./1 min at 60° C. Samples were quantified in the GeneAmp 7500 Sequence Detection System (Applied Biosystems). Transcript levels were determined using rp139 as a basis of comparison.

TABLE 2

List of primers and probes used for Q-PCR

| Primers and Probes | Sequences | Sequence Identifier |
|---|---|---|
| rp139-F1 | 5'GAACAGGCCCATCCCTTATTG 3' | SEQ ID NO.: 38 |
| rp139-R1 | 5'CGGCGCTTGGCATTGTA 3' | SEQ ID NO.: 39 |
| rp139-MGB1 | 5'ATGCGCACTGACAACA3' | SEQ ID NO.: 40 |
| CcSPS1-R1 | 5'CGGAATGTTAGCTGTTATG 3' | SEQ ID NO.: 41 |
| CcSPS1-F1 | 5'GAAATTGCGGGCTAGGATCA 3' | SEQ ID NO.: 42 |
| CcSPS1-MGB1 | 5'GCCATTCGAGGCATGAATCT3' | SEQ ID NO.: 43 |
| CcSS2-F1 | 5'TTCTGCCAGTCTTGCCTTTCTT 3' | SEQ ID NO.: 44 |
| CcSS2-R1 | 5'CGTAATTGACACTTGAAGAGGGACTA 3' | SEQ ID NO.: 45 |
| CcSS2-MGB1 | 5'TTGTTGGTTGGTTGTGTCT3' | SEQ ID NO.: 46 |

Soluble Sugars quantification. Grain tissues were separated from pericarp and hulls. The grain were homogenized in cryogenic grinder with liquid nitrogen and the powder obtained was lyophilized for 48 hours (Lyolab bII, Secfroid). Each sample was weighed and suspended in 70 ml of double-distilled water previously pre-heated to 70° C., then shaken vigorously and incubated for 30 min at 70° C. After cooling to room temperature, the sample was brought to 100 ml by adding doubled-distilled water, and then paper filtered (Schleicher and Schuell filter paper 597.5). Sugars of extracted coffee grain tissues were separated by HPAE-PED according to Locher et al., 1998 using a Dionex PA 100 (4×250 mm) column. Sugar concentration was expressed in g per 100 g of DW (dry weight).

Enzymatic Activity analysis. Sucrose synthase activity was measured according to Lafta and Lorenzen (1995). Sucrose phosphate synthase activity was measured according to Trevanion et al. (2004).

EXAMPLE 2

Identification of cDNA Encoding Enzymes of Sucrose Metabolism

More than 47,000 EST sequences were identified from several coffee libraries made with RNA isolated from young leaves and from the grain and pericarp tissues of cherries harvested at different stages of development. Overlapping ESTs were subsequently "clustered" into "unigenes" (ie contigs) and the unigene sequences were annotated by doing a BLAST search of each individual sequence against the NCBI non-redundant protein database.

Enzymes directly involved in the synthesis and degradation of sucrose have been widely studied in plants, and especially during fruit, tuber, and seed development in plants such as tomato (*Lycopersicon esculentum*), potato (*Solanum tuberosum*) and corn (*Zea mays*). DNA sequences coding for all known key proteins involved in sucrose synthesis and degradation have been identified and characterized in several species and are available in GenBank. Accordingly, the known sequences of plant enzymes, especially sequences from organisms closely related to coffee (e.g., tomato and potato), were used to find similar sequences present in the above-described EST libraries and in other coffee cDNA libraries. To search the aforementioned EST collection, protein sequences of tomato and potato were used in a tBLASTn search of the "unigene" set 3 as described in Example 1. Those in-silico "unigenes" whose open reading frames showed the highest degree of identity with the "query" sequence were selected for further study. In some cases, the selected "unigenes" contained at least one EST sequence that potentially represented a full length cDNA clone, and that clone was then selected for re-sequencing to confirm both its identity and the "unigene" sequence.

A. Sucrose Synthase CcSS2 (SEQ ID NO:1)

Figure 2A:
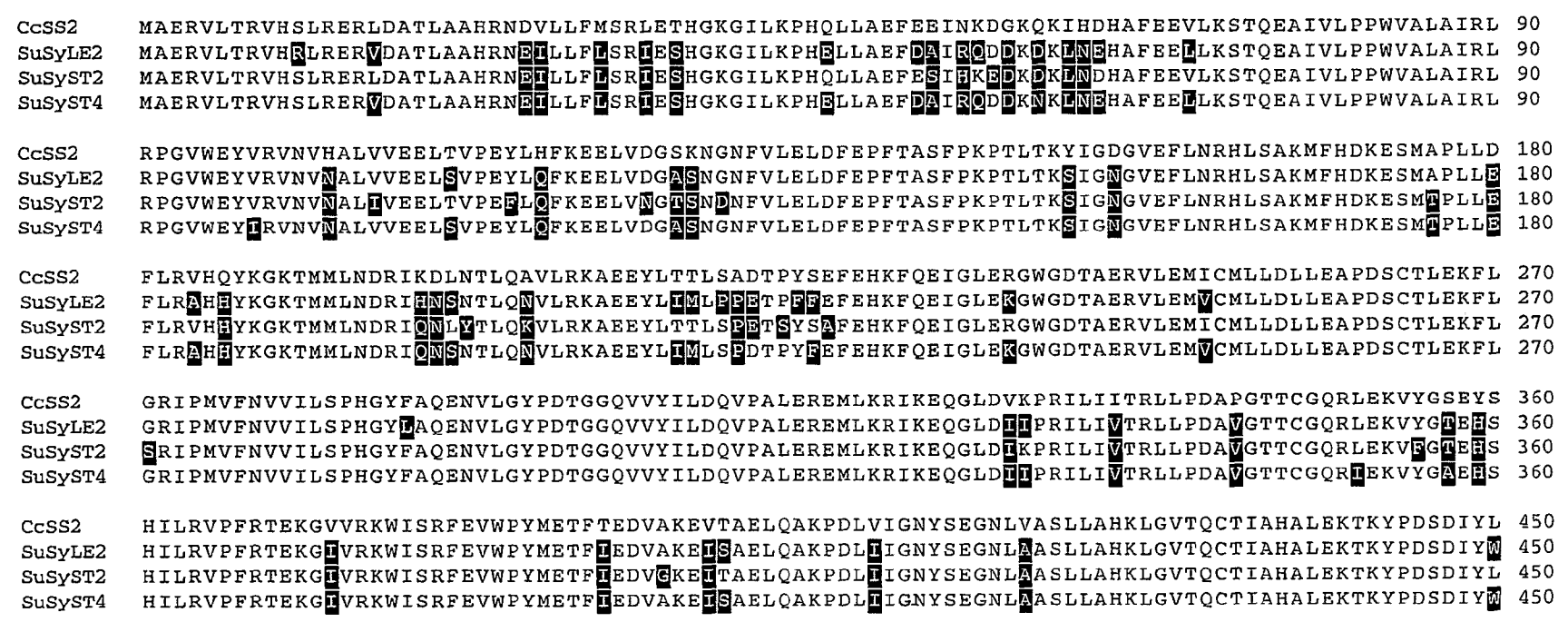

The clone A5-1540, which is highly related to sucrose synthase 2 (SS2) from tomato (*Lycopersicon esculentum*, NCBI Protein Identifier No. CAA09681), was found in a coffee cDNA collection (as opposed to the EST collection). The protein encoded by A5-1540 clone is 88.6% identical to SS2 from tomato and is apparently full length (FIG. 2). The cDNA insert is 3048 bp long, and is characterized by a 2427 bp ORF which starts at position 248 and finishes position 2668. This sequence is referred as SEQ ID NO 1. The deduced protein (SEQ ID NO:8) is 805 aa long, with a predicted molecular weight of 92.6 kDa. The protein sequence encoded by the clone A5-1540 was analyzed for similarity to all publicly available protein sequences contained in the NCBI non-redundant database. The resulting alignment of the most closely related sequences is presented in FIG. 2. As can be seen from the figure, residues 7-554 of SEQ ID NO:8 comprises a domain that characterizes members of the sucrose synthase family, and residues 565-727 is a domain that characterizes glycosyl transferase group 1.

As well as being closely related to SS2 of tomato, it is also closely related to potato SS2 (89% identity; NCBI Protein Identifier No. AA034668). Subsequently, unigene # 97089 was found in the EST database, and that sequence was determined to correspond to the same sequence as A5-1540. However, the longest clone in this unigene is over 1,400 nucleotides shorter than the clone A5-1540, and thus the EST database does not appear to contain a full length clone. In monocotyledons (maize and sorghum), SS is encoded by three differentially expressed nonallelic loci, sus1, sus2 and sus3 (Chourey et al., 1991, Huang et al., 1996, Carlson et al. 2002). Most dicotyledonous species contain two nonallelic SS genes, which are functional analogs of two classes of SS genes from monocotyledons (Fu et al., 1995). Homology results show that the coffee sequence is closest to the SS2 sequence of potato and the protein encoded by clone A5-1540 therefore was designated CcSS2, for *Coffea canephora* sucrose synthase 2, herein.

B. Sucrose Phosphate Synthase CcSPS1 (SEQ ID NO:2)

The protein sequence of sucrose phosphate synthase (SPSLE1, NCBI Protein Identifier No. AAC24872) from tomato (*Lycopersicon esculentum*) was used to perform a similarity search of the EST-based unigene set using the tBLASTn algorithm. No unigene was found that could potentially code for an SPS protein.

Due to lack of a match in the available database, a partial sequence from the *Coffea canephora* BP-409 genome was amplified using degenerate oligonucleotides. By alignment of different SPS protein sequences, it was possible to identify a highly conserved domain and to design degenerate primers corresponding to the protein sequence encoded at the end of exon 4 and at the beginning of exon 7 (Fragment C1 in FIG. 3).

Two different PCR fragments of 1500 and 2000 bp, respectively, were amplified using PCR and degenerate oligonucleotides. After sequencing of both genomic sequences, an alignment of putative encoded protein sequences with the tomato protein sequence SPSLE1 showed isolation of partial sequences from two different coffee SPS genes, CcSPS1 and CcSPS2. The fragments corresponding to CcSPS1 and CcSPS2 partial sequence were 1937 and 1564 bp long, respectively. The protein sequences encoded by partial clones of CcSPS1 and CcSPS2 were found to share a high degree of homology. Introns 4, 5 and 6 were shorter for CcSPS2, thus explaining the difference in size between the two amplified fragments (data not shown). Preliminary expression analysis indicated that CcSPS2 was not expressed, while CcSPS1 was expressed in various tissues, including grain. Therefore, the CcSPS1 gene was examined further.

Figure 3:
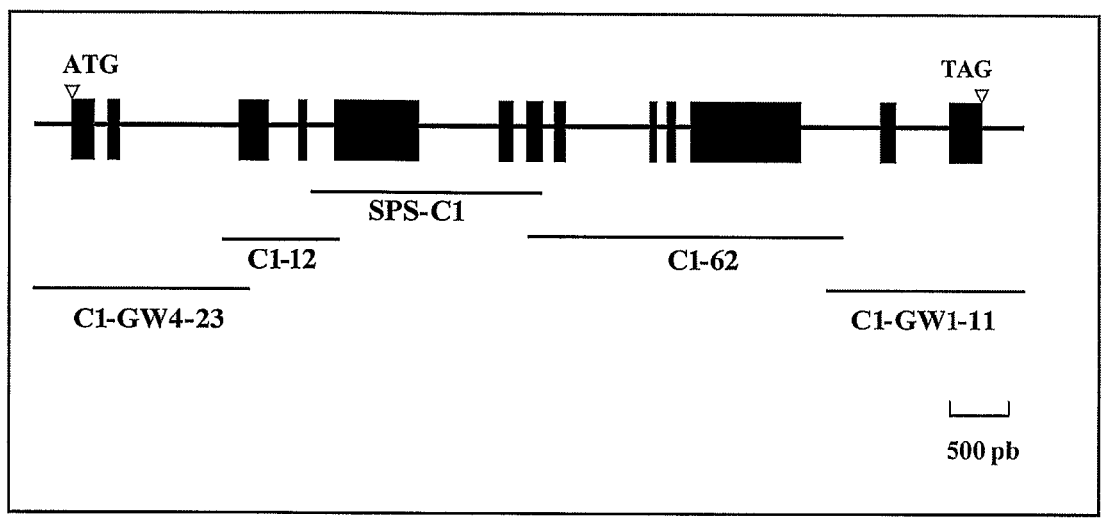
FIG. 3. Schematic representation of CcSPS1 gene from *C. canephora*. The SPS-C1 fragment has been amplified by PCR from BP-409 genomic DNA using the degenerate primers SPS-3 and SPS-4. Successive genome walking experiments subsequently permitted the amplification of the overlapping fragments for the 5' and 3' flanking regions of SPS-C1. Alignment of the resulting genomic clones (C1-12, C1-GW4-23, C1-62 and C1-GW1-11) has lead to the complete sequence of CcSPS1 gene. The putative protein coding region has been localized by alignment with the closely related sucrose phosphate synthase protein SPSLE1 (accession number No. AAC24872) (SEQ ID NO.:14) from tomato (*Lycopersicon esculentum*). The protein-coding regions are shown in black. Triangles indicate the position of the translation initiation start (ATG) and stop (TAG) codons.
Figure 4A:
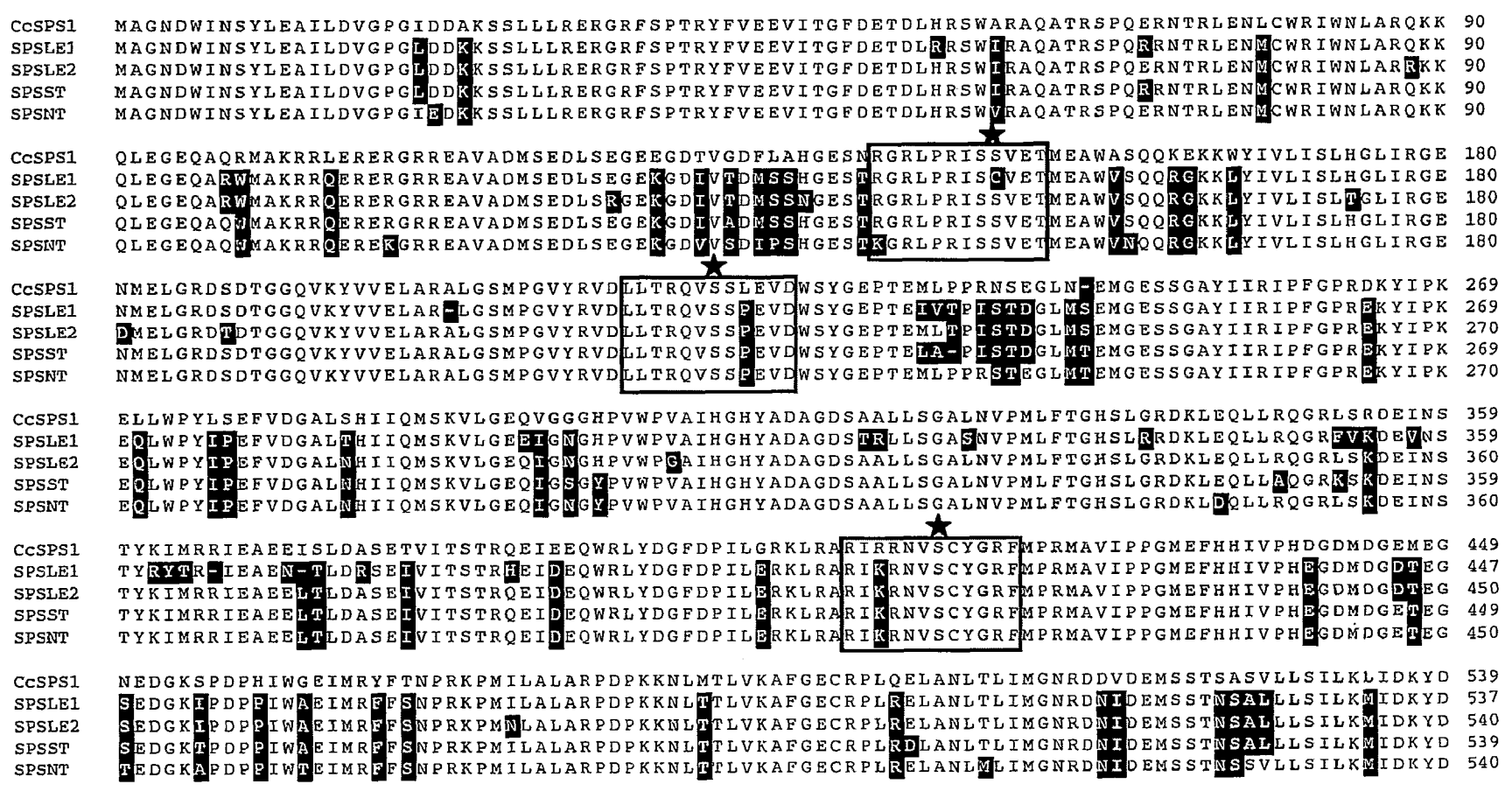
Figure 4B:
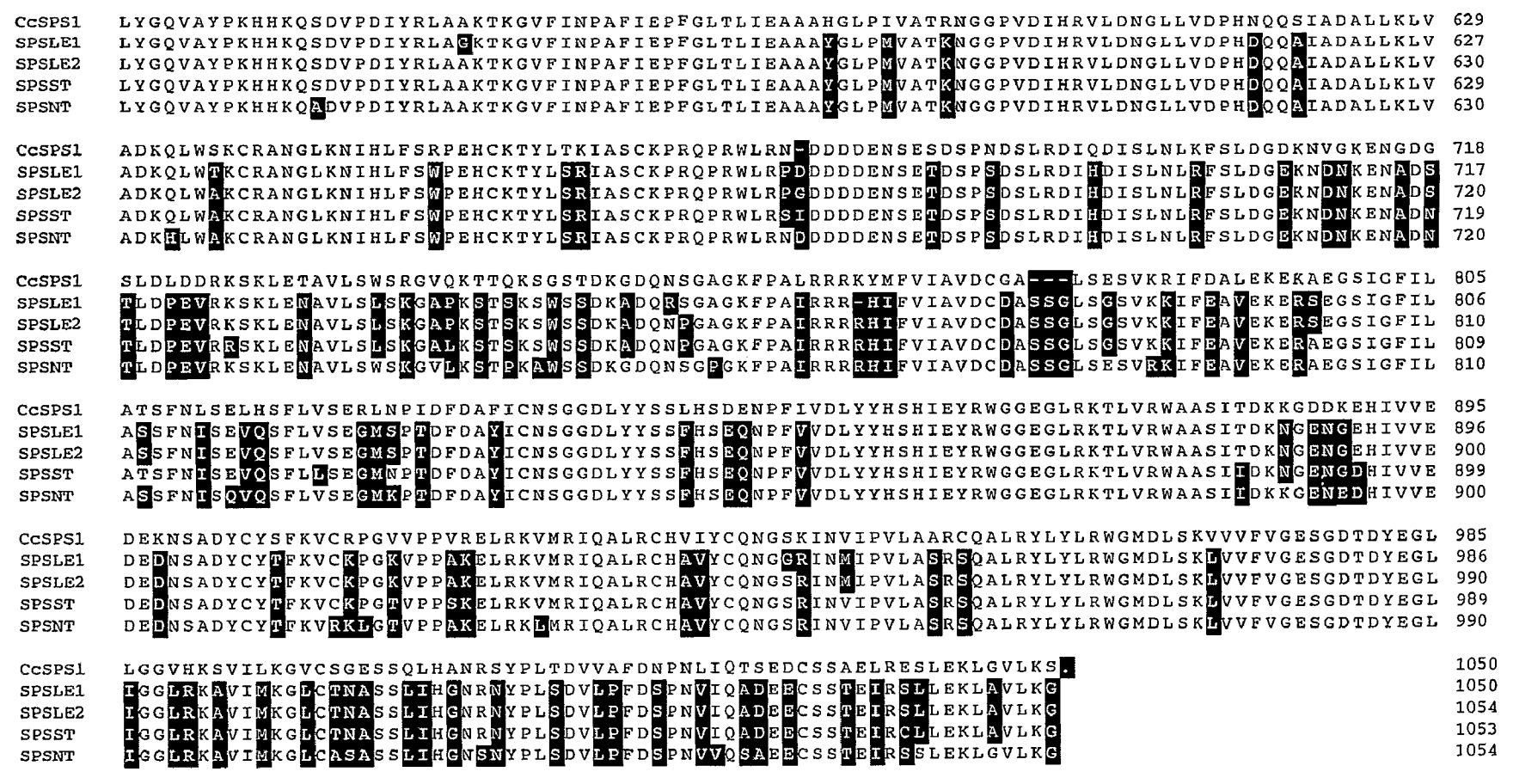

Using several rounds of primer directed genome walking using the Genome Walker™ technique, a full length genomic sequence for the CcSPS1 gene was amplified. A schematic representation of the CcSPS1 gene is shown in FIG. 3. The gene is characterized by 13 exons and 12 introns. The CcSPS1 gene is 7581 bp long (from initiation codon ATG to stop codon TAG) is referred to as SEQ ID NO:6. Using specific primers deduced from CcSPS1 genomic sequence, the CcSPS1 full length cDNA was amplified by RT-PCR. Several RNA samples were used, positive amplification corresponding to the full length cDNA sequence was only obtained using RNA extracted from pericarp at yellow stage from robusta. The CcSPS1 cDNA is 3150 bp long and this DNA sequence is referred as SEQ ID NO: 2. The deduced protein, SEQ ID NO: 9, is 1049 aa long, with a predicted molecular weight of 117.9 kDa. The protein sequence encoded by the CcSPS1 cDNA shows a very high level of homology (82.6%) with the tomato SPSLE1 protein sequence (FIG. 4). In addition, residues 168-439 of SEQ ID NO:9 characterize members of the sucrose phosphate synthase family, and residues 467-644 characterize glycosyl transferases group 1 family members.

C. Sucrose Phosphate Phosphatase CcSP1 (SEQ ID NO:3)

The protein sequence of sucrose phosphatase (SP, NCBI Protein Identifier No. AA033160) from tomato (*Lycopersicon esculentum*) was used to perform a similarity search of the EST-based unigene set using the tBLASTn algorithm. The ORF of unigene #102159 showed a high degree of homology to the tomato SP sequence and the single EST (cDNA) in this unigene, clone cccl19n15, was isolated and its insert was fully sequenced. The cDNA insert of cccl19n15 is apparently full length and was found to be 1721 bp long. This sequence is referred as SEQ ID NO 3. The complete ORF sequence of this clone was 1248 bp long, starting at position 135 and finishing at position 1409. The deduced protein (SEQ ID NO:10) was 415 aa long with a predicted molecular weight of 46.7 kDa. Residues 1-408 of SEQ ID NO:10 characterize members of the sucrose-6F-phosphate phosphohydrolase family. The ORF of cccl19n15 is 81% identical to the tomato SP protein. The protein encoded by cccl19n15 was also analyzed for similarity to all publicly available protein sequences contained in the NCBI nonredundant database. The alignment of sequences showing the highest homologies is presented in FIG. 5. Only one distinct unigene has been found in the coffee cDNA libraries. Several species (including maize, tomato, wheat and barley) are known to contain at least two SP genes; *Arabidopsis* has four and rice three (Lunn et MacRae, 2003). Based on homology results presented here, the cDNA clone cccl19n15 clone has been renamed CcSP1 for *C. canephora* sucrose phosphatase 1.

EXAMPLE 3

Control of SPS Activity by Reversible Protein Phosphorylation

A major regulatory site of spinach SPS has been identified as Ser 158 (McMichael et al., 1993). Phosphorylation of Ser158 is both necessary and sufficient for the inactivation of SPS in vitro. Similar results were shown for the phosphorylation of Ser162 of maize SPS in studies of maize leaves, as well as transgenic tobacco expressing the maize SPS gene (Huber et al., 1995). Although the regulatory phosphorylation sequence of spinach SPS is not conserved exactly, all sequences available to date were determined to contain a homologous seryl residue.

The CcSPS1 deduced protein sequence was aligned with other SPS protein sequences from different species. The serine residue of CcSPS1 most likely to be homologous to Ser 158 in spinach was identified as Ser 150 (FIG. 4). Most of the residues surrounding the putative phosphorylation site are consistently conserved among the five aligned proteins, e.g., there are basic residues at P-3 (R), P-6 (R) and P-8 (R or K) (numbering relative to Ser, which is position 0). Several, and possibly all, of these conserved residues may be important for recognition by a protein kinase (Huber and Huber, 1996; McMichael et al., 1993). The enzymatic activity of CcSPS1 could be modulated by phosphorylation/dephosphorylation of Ser150. In one example, the Ser150 could be replaced with another conservative replacement amino acid by site-directed mutagenesis; thereby, eliminating this phosphorylation site and enhancing SPS activity by eliminating regulation via phosphorylation.

Recent evidence suggests that there may be a second regulatory phosphorylation site at Ser 424 of spinach SPS, which is phosphorylated when leaf tissue is subjected to osmotic stress (Toroser and Huber, 1997). Phosphorylation of Ser 424 in spinach activates the enzyme, perhaps by antagonizing the inhibitory effect of Ser158 phosphorylation. This site was also determined to be widely conserved among species. The homologous site in CcSPS1 protein was determined to be Ser 415. The sucrose synthesis activity of SPS could be enhanced by placing coffee in a simulated high osmotic stress environment to facilitate the phosphorylation of Ser415.

A third potential phosphorylation site may also exist, inasmuch as recent results have demonstrated that 14-3-3 proteins can associate with spinach leaf SPS in the presence of $Mg^{2+}$. The effect of this specific 14-3-3 protein/SPS interaction was to partially inhibit the SPS activity. It has been proposed that the 14-3-3 protein may function as a scaffold protein to facilitate the interaction of SPS with other proteins. The suggested site of interaction in spinach SPS is Ser 229. The homologous region in CcSPS1 is Ser 221 and, notably, this region of the protein is strongly conserved (FIG. 4). In one example, the Ser221 could be replaced with another conservative replacement amino acid by site-directed mutagenesis; thereby, eliminating this phosphorylation site and enhancing SPS activity by eliminating regulation via phosphorylation.

In summary, SPS enzymatic activity can be regulated by reversible protein phosphorylation, and three sites have been shown to be involved in enzyme activity regulation of spinach or maize enzyme. By alignment of CcSPS1 with SPS from other species, these putative seryl residues have been localized in CcSPS1 to Ser 150, Ser 221 and Ser 415.

EXAMPLE 4

Sugar Accumulation and Enzymatic Activity during Coffee Seed Development

Figure 6A:
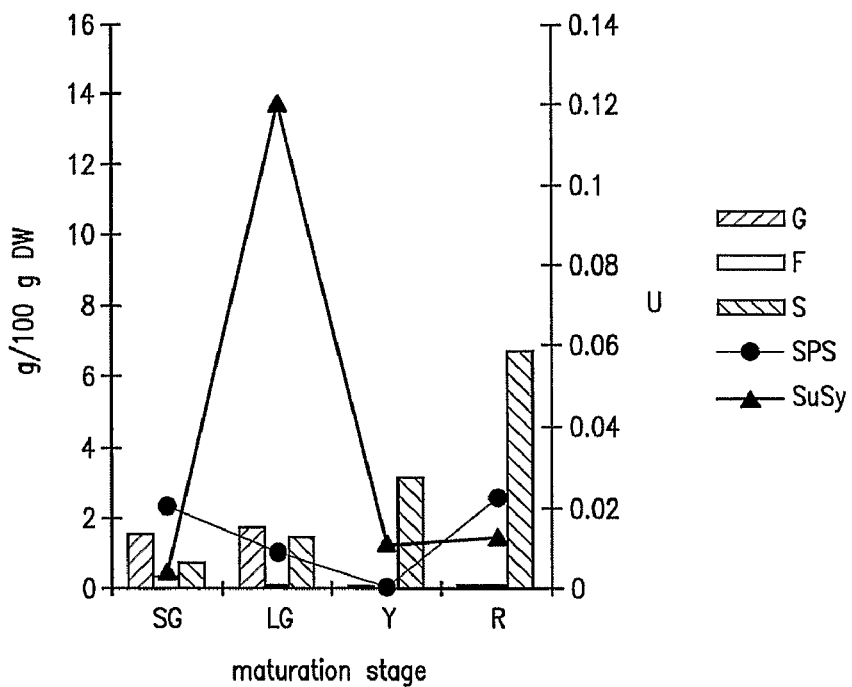
FIG. 6. Changes in activity of SPS and SuSy activity and concentrations of sucrose, glucose and fructose in whole grains (separated from pericarp and locules) during (A) FRT05 *C. canephora* and (B) CCCA12 *C. arabica* coffee grain maturation. Coffee cherries at four different maturation stages characterized by size and color were used, i.e., SG (small green), LG (large green), Y (yellow) and R (red). Concentrations of sucrose, glucose and fructose in the coffee grain were measured in samples harvested in parallel to those used for the assays of SPS and SuSy activity. Sugar concentration is expressed in g/100 g DW while enzymatic activities are expressed in μmoles/h/mg protein.
Figure 6B:
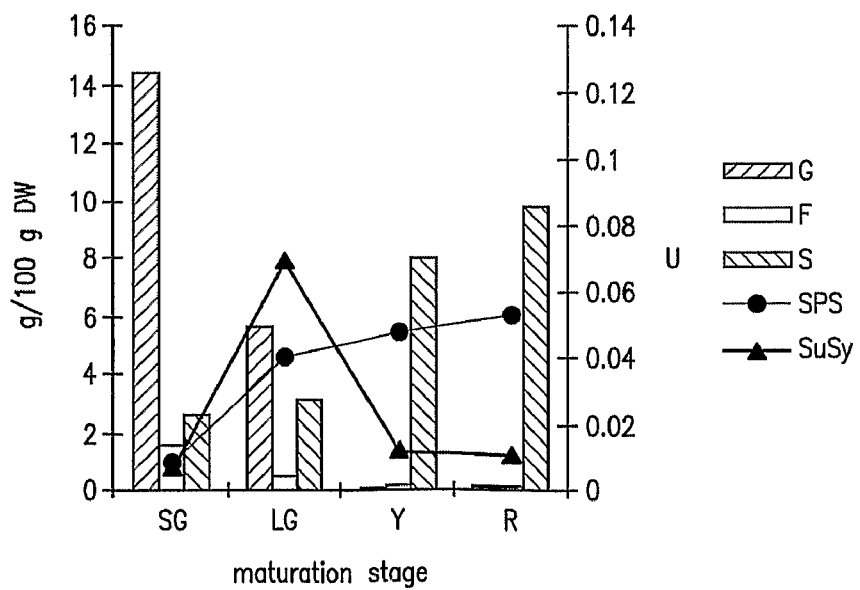
Figure 7:
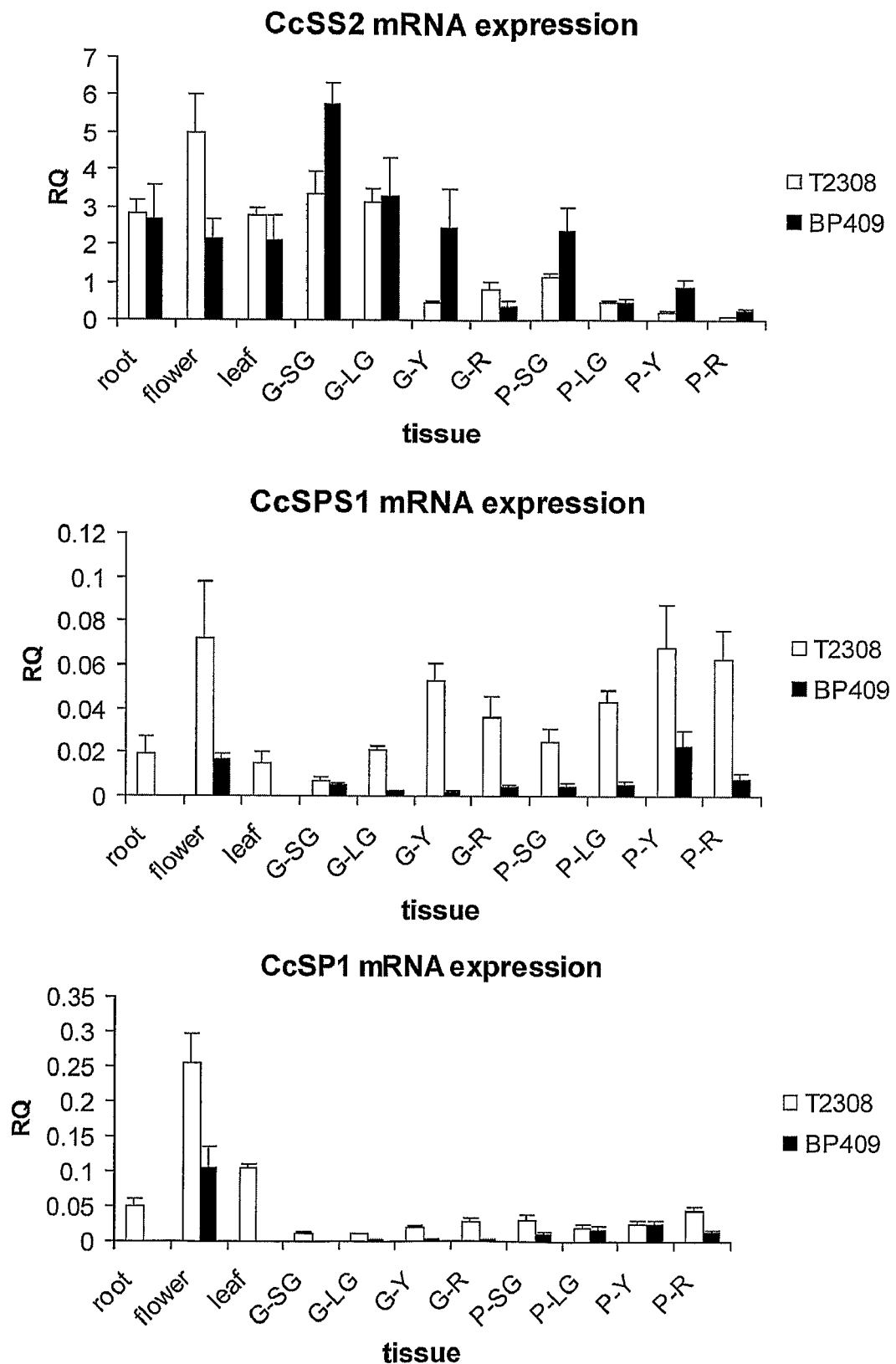
FIG. 7. Tissue-specific mRNA expression profiles of CcSS2, CcSPS1 and CcSP1 in *C. canephora* (Robusta, BP409) and *C. arabica* (Arabica, T2308) using real-time RT-PCR. Total RNA was isolated from root, flower, leaf and coffee beans harvested at four different maturation stages i.e. Small-Green (SG), Large-Green (LG), Yellow (Y) and Red (R). For each maturation stage, coffee cherries have been separated from pericarp (P) and grains (G). Total RNA was reverse transcribed and subjected to real-time PCR using TaqMan-MGB probes. Relative amounts were calculated and normalized with respect to rp139 transcript levels. Data shown represent mean values obtained from three amplification reactions and the error bars indicate the SD of the mean.

Sugar Quantification. Sugar levels during coffee grain maturation were examined in *C. canephora* variety FRT05 (robusta) and *C. Arabica* variety CCCA12 (arabica). These two genotypes were chosen because they have been found to possess significantly different levels of sucrose. The amounts of sucrose, glucose and fructose in the FRT05 and CCCA12 coffee grain during maturation were measured in samples harvested in parallel. The same samples were also used for the assays of SPS and SuSy activity described below. The results are shown in FIG. 6.

At the earliest stage of maturity (stage SG), the main free sugar was found to be glucose, but the concentration is 10 times higher in arabica (14%) than robusta (1.5%). At the same stage, fructose concentration was also higher in arabica (1.5%) than robusta (0.3%), but at a much lower level than glucose. By the end of grain development, concentrations of glucose and fructose were found to have decreased to very low levels for both species, with only trace levels being detected at the mature red stage (R). The decrease in fructose and glucose was accompanied by an increase in sucrose, which approached 100% of total free sugars in mature grains, with higher levels found in arabica (9.82%) than robusta (6.71%). These results represent only free sugar accumulation and do not include their modified form, e.g., UDP-G, F6-P and S6-P, which are also known to play a role in sucrose metabolism (FIG. 1).

SuSy and SPS Enzyme Activity. In parallel to the sugar quantification, sucrose synthase (SuSy) and sucrose phosphate synthase (SPS) enzyme activities were studied in order to determine if there might be a strong correlation between free sugar accumulation and these particular enzyme activities and to elucidate the reason CCCA12 (Arabica) accumulates 30% more sucrose than FRT05 (robusta).

The enzymatic activities of SuSy and SPS were determined similarly for each of the same development stages. SuSy (EC 2.4.1.13) catalyzes the reversible cleavage of sucrose in the presence of UDP to form UDP-glucose and fructose, while SPS (EC 2.3.1.14) catalyzes the synthesis of sucrose phosphate and UDP starting from fructose 6-phosphate and UDP-Glucose (FIG. 1).

Low SuSy activity was observed in early stage of development (stage SG), with the activity being almost two times higher in arabica (0.007 U) than robusta (0.004) (FIG. 6). SuSy activity rose drastically between SG and LG stage and reached a peak of 0.069 U for arabica and 0.12 U for robusta. Again, SuSy activity was twice as high for robusta as compared with arabica at the LG stage. In the later stage of development, the SuSy activity declined dramatically for both species to reach approximately similar low levels of activity at the Y stage. Between Y and R stages, SuSy activity remained constant but weak for arabica as well as for robusta.

Overall, the SuSy activity was clearly higher at all stages in robusta than in arabica. The profiles of SuSy activity during both arabica and robusta grain development were similar to those seen in various other plants, such as tomato and maize. For those species, it has been shown that SuSy activity is highly correlated with sucrose unloading capacity from the phloem (phenomenon also called sink strength; Sun, et al., 1992; Zrenner et al., 1995). If this correlation exists in coffee grain, this implies that the sink strength of robusta should be higher at the large green stage of robusta versus the same stage of arabica. Interestingly, although the peak of SuSy activity reached its highest point between SG and LG stage in both species, the sucrose concentrations of both were not drastically increased. This suggests either that sucrose is not re-synthesised immediately after import, or that sucrose is being rapidly funneled into another pathway.

The activity pattern observed for SPS activity during coffee seed maturation was found to be completely different for arabica and robusta (FIG. 6). At the earliest stage (SG), SPS activity in robusta (0.02 U) was 2.5-fold higher than that observed for arabica (0.008 U). In robusta, SPS activity was seen to decrease to undetectable levels at the Y stage then rise again to the levels seen in the SG stage at R stage. In contrast, for arabica, SPS activity rose sharply between SG and LG stages, reaching an activity of 0.04 U, and then continued to rise slowly during the final maturation process, reaching 0.052 U at stage R. The fluctuation of SPS activity appeared to be quite high for robusta, while, in contrast, the SPS activity rose gradually during grain maturation to reach a relatively high level at the R stage in arabica. The difference in the SPS activity levels during grain maturation is likely to be an important contributing factor that leads to sucrose accumulation that is 30% higher in arabica than robusta.

EXAMPLE 5

CcSS2, CcSPS1 and CcSP1 mRNA Expression at Different Stages of Coffee Grain Maturation To determine if any correlation existed between the enzymatic activity fluctuations seen for SuSy and SPS and the expression of these genes during coffee bean maturation, the expression of the three genes CcSS2, CcSPS1 and CcSP1 during T2308 (*C. arabica*, arabica) and BP-409 (*C. canephora*, robusta) grain development was characterized. For comparative purposes, the expression of these genes in different coffee tissues, such as leaf, flower and root, was also examined. It is noted that gene expression analysis was not carried out on the same genotypes as those used for enzymatic activities, but comparisons were still made between arabica and robusta.

RNA was extracted from BP-409 and T2308 coffee cherries at four different maturation stages characterized by size and color, i.e. SG (small green), LG (large green), Y (yellow) and R (red or mature). For each stage, pericarp and grain were separated before total RNA was extracted as described in Example 1. Total RNA was also extracted from other tissues (leaf, root and flower). Gene expression was analyzed by performing real time RT-PCR (TaqMan, Applied Biosystems). Relative transcript levels were quantified against an endogenous constitutive transcript rp139. The gene specific primers and the TaqMan probes used are listed in Example 1.

The CcSS2 transcript was highly expressed in robusta grain at the earliest stage of development (6 U of RQ). The level of CcSS2 mRNA then decreased gradually during coffee grain maturation until being equivalent to a value of 0.3 U of RQ at the mature stage (R). A relatively similar expression pattern was seen for arabica grain, although the absolute levels were different. The relative amount of expression for CcSS2 was higher in robusta than arabica grain at the SG stage, equivalent at LG stage for both species, and lower in robusta than arabica at the Y stage. Transcript accumulation was slightly greater in arabica than robusta at the mature stage (R). Except in the small green stage, low levels of CcSS2 accumulate in the pericarp of robusta and arabica cherries. Similar results (Wang et al, 1994; Carlson et al., 2002) were obtained previously in tomato and maize, in both cases there was an early accumulation of SuSy mRNA, followed by decreasing levels of transcripts being detected as fruit and grain maturation progressed. Significant levels of CcSS2 transcripts were also detected in other coffee tissues such as root, flower and leaf for both species.

The CcSPS1 transcript is expressed at very low levels compared to CcSS2 mRNA, with the highest RQ observed being 0.07 U in arabica (FIG. 6). CcSPS1 transcripts were almost undetectable during all stages of robusta grain maturation examined, and the highest expression detected in robusta was in yellow pericarp and flower (0.02 U). The level of CcSPS1 transcripts in the robusta root and leaf tissues were below detection. Interestingly, CcSPS1 transcripts were detected in all the tissues examined for arabica, especially in the flower, grain and pericarp. In arabica, the transcript level increased 10-fold between SG (0.005) and Y stage (0.05 U). In mature grain stage, the level was slightly lower (0.04 U). Overall, the results obtained indicate that CcSPS1 mRNA expression is significantly higher in arabica than robusta. This main result correlates well with the differences in SPS activity, presented earlier, with the detectable SPS activity being significantly higher in arabica than in robusta.

CcSP1 transcript accumulation was very low in grain and pericarp at all the maturation stages examined for both species, although expression was slightly higher in arabica than robusta (FIG. 6).

Generally, arabica grains accumulate more sucrose than do robusta grains. To summarize the results set forth above, chemical analysis showed that CCCA12 (Arabica) accumulated 30% more sucrose in the mature grain than FRT05 (robusta). The activity of SuSy and SPS was also determined for both species during coffee bean maturation. Notably, SuSy activity was found to be higher in robusta than arabica. The peak of activity was found at the LG stage for both species. The rapid growth phase of coffee fruit development is between SG and LG stage, a phase that correlates well with the highest level of SuSy activity. Results in other systems have shown that SuSy activity is highly correlated with sucrose unloading capacity from the phloem at the earliest stages of tomato fruit development (Sun, et al., 1992; Zrenner et al., 1995; N'tchobo, 1999; Wang et al., 1993). The postulate that the level of SuSy activity indicates the level of sink strength may suggest that the sink strength is higher in robusta than arabica. SPS activity has also been determined at the same stages of grain maturation. However, SPS activity did not follow the same schema in robusta and arabica during coffee grain maturation. While SPS activity fluctuated during robusta grain development, the activity rose steadily during early arabica grain development and stayed at relatively high levels until the end of maturation. Without intending to be limited by any explanation of mechanism, these observations suggest a mechanism in which the steady increase in SPS activity seen during arabica grain maturation may account for at least part of the difference in sucrose concentration found in mature arabica versus robusta grain. CcSS2 and CcSPS1 mRNA accumulation in the developing grain was also consistent with the activity levels detected for the respective enzymes. For SuSy, the level of CcSS2 transcript accumulation was seen to increase up to the large green stage then fall as the grain maturity continued. The level of CcSPS-C1 transcripts rose consistently, albeit slightly, as arabica grain maturation progressed, while the level of transcripts was much lower in the grain of robusta at all stages examined. Again, the expression data obtained for CcSS2 and CcSPS1 supports the notion that SPS activity could be the limiting step for re-synthesis of sucrose during final steps of coffee grain maturation, especially in robusta grain.

In the perspective of genetically improving robusta coffee quality, the SPS enzyme therefore may be a key factor for generating higher final sucrose concentrations in the mature grain. Alterations in carbon partitioning in plants, and most particularly improvement of sucrose levels in sink organs, have been accomplished in other plant species. For instance, tomato plants were transformed with a construct comprising a maize SPS cDNA under the control of the SSU promoter (Rubisco small subunit promoter) (Worrell, et al., 1991; Galtier et al. 1993; Foyer and Ferrario, 1994; Micallef, et al., 1995; Van Assche et al., 1999; Nguyen-Quoc et al., 1999). The total SPS activity in the leaves of the transformed plants was six times greater than that of the controls and the total SPS activity in the mature fruit from the transformed plants was twice than that of untransformed controls. The combination of overexpression, combined with possible de-regulation of enzyme activity in the transgenic tissue were thought to contribute to the overall increase in SPS activity. The increase in SPS activity was also accompanied by a significant increase (25%) in total overall SuSy activity in 20 day old tomato fruit. In this case, SuSy activity was measured with an assay in the direction of sucrose breakdown (Nguyen-Quoc et al.; 1999). Fruit from these transgenic tomato lines also showed higher sugar content (36% increase) compared to untransformed plants (Van Assche et al., 1999). Biochemical studies have also shown that the high levels of the corn SPS activity in the plants caused a modification of carbohydrate portioning in the tomato leaves with an increase of sucrose/starch ratios and also a strong improvement in the photosynthetic capacity. The tomato plants appeared to tolerate the elevated levels of SPS as there were no apparent detrimental growing effects. In studies by others, plants transformed with the construct 35SCaMV-SPS (35 S Cauliflower Mosaïc Virus) were found to have three to five times more total SPS activity in leaves than in wild-type plants, but tomato fruit obtained from those particular transformants did not show any increase in SPS activity (Laporte et al. 1997; Nguyen-Quoc et al. 1999). Thus, it appears that the choice of promoter can influence the ultimate effect of transformation of plants with a heterologous SPS gene.

REFERENCES

Altschul S. F., Madden T. L., Schaffer A. A., Zhang J., Zhang Z., Miller W. and Lipman D. 1990. Gapped BLAST and PSI-Blast: a new generation of protein database search. *Nucleic Acids Res.* 25: 3389-3402.

Badoud R., 2000. "What do we know about coffee chemistry, flavour formation and stability? Internal Note, 23 Oct. 2000.

Bäumlein H, Nagy I, Villarroel R, Inzé D, Wobus U. 1992. Cis-analysis of a seed protein gene promoter: the conservative RY repeat CATGCATG within the legumin box is essential for tissue-specific expression of a legumin gene. *Plant J.* 2: 233-239.

BenAmor M. and Mc Carthy J. 2003. Modulation of coffee flavour precursor levels in green coffee grains. European patent Application No. 03394056.0 NESTEC S.A.

Carlson S. J., Chourey P. S., Helentjaris T. and Datta R. 2002. Gene expression studies on developing kernels of maize sucrose synthase (SuSy) mutants show evidence for a third SuSy Gene. Plant Mol. Biol. 49: 15-29.

Chahan Y., Jordon A., Badoud R. and Lindinger W. 2002. From the green bean to the cup of coffee:investing coffee roasting by on-line monitoring of volatiles. *Eur Food Res Technol.* 214:92-104.

Chourey P. S., Taliercio E. W. and Kane E. J. 1991. Tissue specific expression and anaerobically induced posttranscriptional modulation of sucrose synthase genes in *Sorghum bicolour* M. *Plant Physiol.* 96:485-490.

Crouzillat D., Lerceteau E., Petiard V., Morera J., Rodriguez H., Walker D., Philips W. R. R., Schnell J., Osei J. and Fritz P. 1996. *Theobroma cacao* L.: a genetic linkage map and quantitative trait loci analysis. *Theor Appl Genet.* 93: 205-214.

Echeverria E., Salvucci, M. E., Gonzalez, P., Paris G. and Salerno G. 1997. Physical and kinetic evidence for an association between sucrose-phosphate synthase and sucrose-phosphate phosphatase. *Plant Physiol.* 115:223-227.

Foyer C. H. and Ferrario S. 1994. Modulation of carbon and nitrogen metabolism in transgenic plants with a view to improved biomass production. In: Lea P J, ed. Transgenic plants and plant biochemistry. University of Lancaster: Society/Host colloqium, 909-915.

Fu, H. and Park, W. D. 1995. Sink- and vascular associated sucrose synthase functions are encoded by different gene classes in potato. *Plant Cell.* 7: 1369-1385.

Galtier N., Foyer C. H., Huber J., Voelker T. A. and Huber, S. C. 1993. Effects of Elevated Sucrose-Phosphate Synthase Activity on Photosynthesis, Assimilate Partitioning, and Growth in Tomato (*Lycopersicon esculentum* var UC82B). *Plant Physiol.* 101:535-543.

Holscher W. and Steinhart H. 1995. Development in Food Science V37A Food Flavors: Generation, Analysis and Process Influence. Elsevier, 785-803.

Huang J. W., Chen J. T., Yu W. P., Shyur L. G., Wang A. Y., Sung H. Y., Lee P. D., and Su J. C. 1996. Complete structures of three rice sucrose synthase isogenes and differential regulation of their expressions. *Biosci. Biotechnol. Biochem.* 60: 233-239.

Huber S. C. and Huber J. L. 1996. Role and regulation of sucrose-phosphate synthase in higher plants. *Annu. Rev. Plant Physiol. Plant Mol. Biol.* 47: 431-444.

Huber S. C., McMichael R. W. Jr, Huber J. L., Bachmann M., Yamamoto Y. T. and Conkling M. A. 1995 Light regulation of sucrose synthsesis: role of protein phosphorylation and possible involvement of cytosolic $Ca^{2+}$. Carbon Partitioning and Source-Sink Interactions in Plants, ed. M A Madore, W Lucas, pp. 35-44. Rockville, Md.: *Am. Soc. Plant Physiol.*

Illy, A. and Viani, R. 1995. Espresso Coffee: The Chemistry of Quality. Academic Press. London Academic Press Ltd.

Jones T. L. and Ort D. R. 1997. Circadian regulation of sucrose phosphate synthase activity in tomato by protein phosphatase activity. *Plant Physiol.* 113:1167-1175.

Lafta A. M. and Lorenzen J. H. 1995. Effect of High Temperature on Plant Growth and Carbohydrate metabolism in potato. *Plant Physiol.* 109:637-643.

Laporte M. M., Galagan J. A., Shapiro J. A., Boersig M. R., Shewmaker C. K., Sharkey T. D. 1997. Sucrose-phosphate synthase activity and yield analysis of tomato plants transformed with maize sucrose-phosphate synthase. *Planta.* 203: 253-259.

Leloup V., Gancel C., Rytz, A. and Pithon, A. 2003. Precursors of Arabica character in green coffee, chemical and sensory studies. R&D Report RDOR-RD030009.

Locher R., Bucheli P. 1998. Comparison of soluble sugar degradation in soybean seed under simulated tropical storage conditions. *Crop Sci.* 38. 1229-1235.

Lunn J. E. and MacRae E. 2003. New complexities in the synthesis of sucrose. *Curr Opin Plant Biol.* 6: 208-214.

Marraccini P., Deshayes A., Pétiard V. and Rogers W. J. 1999. Molecular cloning of the complete 11S seed storage protein gene of *Coffea arabica* and promoter analysis in the transgenic tobacco plants. *Plant Physiol. Biochem.* 37:273-282.

Marraccini P, Courjault C, Caillet V, Lausanne F, LePage B, Rogers W, Tessereau S, and Deshayes A. (2003). Rubisco small subunit of *Coffea arabica*: cDNA sequence, gene cloning and promoter analysis in transgenic tobacco plants. *Plant Physiol. Biochem.* 41:17-25.

McMichael R. W. Jr, Klein R. R., Salvucci M. E. and Huber S. C. 1993. Identification of the major regulatory phosphorylation site in sucrose phosphate synthase. *Arch. Biochem. Biophys.* 321:71-75.

Micallef, B. J., Haskins, K. A., Vanderveer, P. J., Roh, K.-S., Shewmaker, C. K., and Sharkey, T. D. 1995. Altered photosynthesis, flowering and fruiting in transgenic tomato plants that have an increased capacity for sucrose synthesis. *Planta.* 196:327-334.

N'tchobo H., Dali N., Nguyen-Quoc B., Foyer C. H. and Yelle S. 1999. Starch synthesis in tomato remains constant throughout fruit development and is dependent on sucrose supply and sucrose activity. *J. Exp. Bot.* 50. 1457-1463.

Nguyen-Quoc B., N'Tchobo H., Foyer C. H. and Yelle S. 1999. Overexpression of sucrose-phosphate synthase increases sucrose unloading in transformed tomato fruit. *J. Exp. Bot.* 50: 785-791.

Nguyen-Quoc, B. and C. H. Foyer. 2001. A role for 'futile cycles' involving invertase and sucrose synthase in sucrose metabolism of tomato fruit. *J. Exp. Bot.* 52:881-889.

Robinson N. L., Hewitt J. D. and Bennett A. B. 1998. Sink metabolism in tomato fruit. *Plant Physiol.* 87:732-730.

Rogers W. J., Michaux S., Bastin M. and P. Bucheli. 1999. Changes to the content of sugars, sugar alcohols, myo-inositol, carboxylic acids and inorganic anions in developing grains from different varieties of Robusta (*Coffea canephora*) and Arabica (*C. arabica*) coffees. *Plant Sc.* 149: 115-123.

Russwurm, H. 1969. Fractionation and analysis of aroma precursors in green coffee, ASIC 4: 103-107.

Sugden C., Donaghy P. G., Halford N. G., and Hardie D. G. 1999. Two SNF1-related protein kinases from spinach leaf phosphorylate and inactivate 3-hydroxy-3-methylglutaryl-coenzyme A reductase, nitrate reductase, and sucrose phosphate synthase in vitro. *Plant Physiol* 120:257-274.

Sun J., Loboda T., Sung S. J. S. and Black, C. C. J. 1992. Sucrose synthase in wild tomato, *Lycopersicon chmielewskii*, and tomato fruit sink strength. *Plant Physiol.* 98: 1163-1169.

Toroser D. and Huber S. C. 1997. Protein phosphorylation as a mechanism for osmotic-stress activation of sucrose-phosphate synthase in spinach leaves. *Plant Physiol.* 114: 947-955.

Trevanion S. J., Castleden C. K., Foyer C. H., Furbank R. T., Quick W. P. and Lunn J. E. 2004. Regulation of sucrose-phosphate synthase in wheat (*Triticum aestivum*) leaves. *Functional Plant Biology.* 31:685-695.

Van Assehe, C. Lando, D., Bruneau, J. M., Voelker, T. A., Gervais, M. 1999. Modification of sucrose phosphate synthase in plants. U.S. Pat. No. 5,981,852.

Wang F., Smith A. G. and Brenner M. L. 1993. Sucrose synthase starch accumulation and tomato fruit sink strength. *Plant Physiol* 101:321-327.

Wang, F., Smith A. G. and Brenner M. L. 1994. Temporal and Spatial Expression Pattern of Sucrose Synthase during Tomato Fruit Development. *Plant Physiol* 104:535-540.

Worrell, A. C., Bruneau J-M, Summerfelt K., Boersig M. and Voelker T. A. 1991. Expression of a maize sucrose phosphate synthase in tomato alters leaf carbohydrate partitioning. *Plant Cell* 3:1121-1130.

Zrenner, R., Salanoubat, M., Willmitzer, L., and Sonnewald, U. 1995. Evidence of crucial role of sucrose synthase for sink strength using transgenic potato plants (*Solanum tuberosum* L.). *Plant J.* 7:97-107.

The present invention is not limited to the embodiments described and exemplified above, but is capable of variation and modification within the scope of the appended claims.

What is claimed:

1. A nucleic acid molecule isolated from coffee (*Coffea spp.*) comprising a coding sequence that encodes a sucrose phosphate synthase, wherein the sucrose phosphate synthase has an amino acid sequence that either (1) comprises residues 168-439 or 467-644 of SEQ ID NO:9, or (2) is greater than 95% identical to SEQ ID NO:9.

2. The nucleic acid molecule of claim 1, wherein the sucrose phosphate synthase has an amino acid sequence comprising residues 168-439 and 467-644 of SEQ ID NO:9.

3. The nucleic acid molecule of claim 1, wherein the sucrose phosphate synthase has an amino acid sequence greater than 95% identical to SEQ ID NO:9.

4. The nucleic acid molecule of claim 3, wherein the sucrose phosphate synthase has an amino acid sequence of SEQ ID NO:9.

5. The nucleic acid molecule of claim 1, wherein the coding sequence is greater than 95% identical to either the coding sequence set forth in SEQ ID NO: 2 or the coding sequence of the open reading frame of SEQ ID NO:6.

6. The nucleic acid molecule of claim 5, wherein the coding sequence comprises SEQ ID NO: 2 or the open reading frame of SEQ ID NO:6.

7. The coding sequence of the nucleic acid molecule of claim 1, contained within a vector.

8. The vector of claim 7, which is an expression vector selected from the group of vectors consisting of plasmid, phagemid, cosmid, baculovirus, bacmid, bacterial, yeast and viral vectors.

9. The vector of claim 7, wherein the coding sequence of the nucleic acid molecule is operably linked to a constitutive promoter, or an inducible promoter, or a tissue-specific promoter.

10. The vector of claim 9, wherein the tissue specific promoter is a seed specific promoter.

11. The vector of claim 10, wherein the seed specific promoter is a coffee seed specific promoter.

12. A host cell transformed with the vector of claim 7.

13. The host cell of claim 12, which is a plant cell selected from the group of plants consisting of coffee, tobacco, *Arabidopsis*, maize, wheat, rice, soybean barley, rye, oats, sorghum, alfalfa, clover, canola, safflower, sunflower, peanut, cacao, tomatillo, potato, pepper, eggplant, sugar beet, carrot, cucumber, lettuce, pea, aster, begonia, chrysanthemum, delphinium, zinnia, and turfgrasses.

14. A fertile plant produced from the plant cell of claim 13, wherein the fertile plant comprises in its genome the nucleic acid molecule of claim 1.

* * * * *